(12) United States Patent
Siciliano et al.

(10) Patent No.: US 10,705,084 B2
(45) Date of Patent: Jul. 7, 2020

(54) ANALYTE DETECTION DEVICES, MULTIPLEX AND TABLETOP DEVICES FOR DETECTION OF ANALYTES, AND USES THEREOF

(71) Applicant: Invisible Sentinel, Inc., Philadelphia, PA (US)

(72) Inventors: Nicholas A. Siciliano, Cherry Hill, NJ (US); Martin Joseph Bouliane, Carlsbad, CA (US); Louis Leong, Philadelphia, PA (US)

(73) Assignee: INVISIBLE SENTINEL, INC., Philadelphia, PA (US)

( * ) Notice: Subject to any disclaimer, the term of this patent is extended or adjusted under 35 U.S.C. 154(b) by 399 days.

(21) Appl. No.: 15/290,965

(22) Filed: Oct. 11, 2016

(65) Prior Publication Data
US 2017/0227510 A1    Aug. 10, 2017

Related U.S. Application Data

(63) Continuation of application No. 13/360,528, filed on Jan. 27, 2012, now Pat. No. 9,475,049.
(Continued)

(51) Int. Cl.
*G01N 33/558* (2006.01)
*B01L 3/00* (2006.01)
(Continued)

(52) U.S. Cl.
CPC .......... *G01N 33/558* (2013.01); *B01L 3/5023* (2013.01); *B01L 3/502738* (2013.01); *G01N 33/02* (2013.01); *G01N 33/56916* (2013.01); *G01N 33/56922* (2013.01); *B01L 2300/0816* (2013.01); *B01L 2300/0832* (2013.01); *B01L 2300/0864* (2013.01); *B01L 2300/0874* (2013.01); *B01L 2300/123* (2013.01); *B01L 2400/0406* (2013.01); *B01L 2400/0487* (2013.01); *B01L 2400/0633* (2013.01); *B01L 2400/0694* (2013.01); *G01N 2333/205* (2013.01); *G01N 2333/245* (2013.01); *G01N 2333/255* (2013.01)

(58) Field of Classification Search
USPC ..... 422/400, 401, 420, 425, 430; 435/287.7, 435/287.9, 970, 805, 810; 436/169, 514, 436/518, 530, 810
See application file for complete search history.

(56) References Cited

U.S. PATENT DOCUMENTS

| 3,581,227 A | 5/1971 | Podgorski |
| 4,246,339 A | 1/1981 | Cole et al. |

(Continued)

FOREIGN PATENT DOCUMENTS

| AU | 200025390 B2 | 7/2000 |
| CA | 2024458 A1 | 3/1991 |

(Continued)

OTHER PUBLICATIONS

Notice of Allowance dated Jul. 25, 2017 in U.S. Appl. No. 15/161,753.
(Continued)

*Primary Examiner* — Christopher L Chin
(74) *Attorney, Agent, or Firm* — Pepper Hamilton LLP

(57) ABSTRACT

Devices and methods for the detection of analytes are disclosed. Devices and methods for detecting food-borne pathogens are disclosed.

18 Claims, 39 Drawing Sheets

Related U.S. Application Data

(60) Provisional application No. 61/436,733, filed on Jan. 27, 2011.

(51) Int. Cl.
*G01N 33/02* (2006.01)
*G01N 33/569* (2006.01)

(56) References Cited

U.S. PATENT DOCUMENTS

| | | |
|---|---|---|
| 4,254,084 A | 3/1981 | Blum |
| 4,444,879 A | 4/1984 | Foster et al. |
| 4,446,232 A | 5/1984 | Liotta |
| 4,727,019 A | 2/1988 | Valkirs et al. |
| 4,797,260 A | 1/1989 | Parker |
| 4,828,801 A | 5/1989 | Lombardy wife Alric et al. |
| 4,920,046 A | 4/1990 | McFarland et al. |
| 4,976,926 A | 12/1990 | Matkovich |
| 4,994,240 A | 2/1991 | Hayashi |
| 5,003,988 A | 4/1991 | Guirguis |
| 5,133,363 A | 7/1992 | Guirguis |
| 5,137,691 A | 8/1992 | Parker |
| 5,141,850 A | 8/1992 | Cole et al. |
| 5,149,622 A | 9/1992 | Brown et al. |
| 5,155,022 A | 10/1992 | Naqui et al. |
| 5,155,049 A | 10/1992 | Kauvar et al. |
| 5,160,701 A | 11/1992 | Brown, III et al. |
| 5,166,054 A | 11/1992 | Naqui |
| 5,167,924 A | 12/1992 | Clark |
| 5,175,270 A | 12/1992 | Nilsen et al. |
| 5,185,127 A | 2/1993 | Vonk |
| 5,215,102 A | 6/1993 | Guirguis |
| 5,252,496 A | 10/1993 | Kang et al. |
| 5,296,347 A | 3/1994 | LaMotte, III |
| 5,358,690 A | 10/1994 | Guirguis |
| 5,451,504 A | 9/1995 | Fitzpatrick et al. |
| 5,474,902 A | 12/1995 | Uylen et al. |
| 5,541,069 A | 7/1996 | Mortensen et al. |
| 5,559,041 A | 9/1996 | Kang et al. |
| 5,620,657 A | 4/1997 | Sizto et al. |
| 5,622,871 A | 4/1997 | May et al. |
| 5,741,662 A | 4/1998 | Madsen et al. |
| 5,922,615 A | 7/1999 | Nowakowski et al. |
| 5,948,695 A | 9/1999 | Douglas et al. |
| 5,962,250 A | 10/1999 | Gavin et al. |
| 6,555,390 B2 | 4/2003 | Chandler |
| 6,716,641 B1 | 4/2004 | Sundrehagen |
| 6,766,817 B2 | 7/2004 | da Silva |
| 6,770,447 B2 | 8/2004 | Maynard et al. |
| 7,052,831 B2 | 5/2006 | Fletcher et al. |
| 7,205,159 B2 | 4/2007 | Cole et al. |
| RE39,664 E | 5/2007 | Gordon et al. |
| 7,285,255 B2 | 10/2007 | Kadlec et al. |
| 7,300,750 B2 | 11/2007 | Smart et al. |
| 7,377,904 B2 | 5/2008 | Conway et al. |
| 7,393,697 B2 | 7/2008 | Charlton |
| 7,435,577 B2 | 10/2008 | Lawrence et al. |
| 7,488,606 B2 | 2/2009 | Fleming et al. |
| 7,497,997 B2 | 3/2009 | Glezer et al. |
| 7,531,362 B2 | 5/2009 | Chan |
| 7,582,258 B2 | 9/2009 | Ruhl et al. |
| 7,638,093 B2 | 12/2009 | Wang et al. |
| 7,803,319 B2 | 9/2010 | Yang et al. |
| 7,815,854 B2 | 10/2010 | Cohen |
| 7,819,822 B2 | 10/2010 | Calasso et al. |
| 8,012,770 B2 | 9/2011 | Siciliano et al. |
| 8,183,059 B2 | 5/2012 | Siciliano et al. |
| 8,476,082 B2 | 7/2013 | Siciliano et al. |
| 9,341,624 B2 | 5/2016 | Siciliano et al. |
| 9,347,938 B2 | 5/2016 | Siciliano et al. |
| 9,475,049 B2 | 10/2016 | Siciliano et al. |
| 9,557,330 B2 | 1/2017 | Siciliano et al. |
| 9,816,984 B2 | 11/2017 | Siciliano et al. |
| 9,823,240 B2 | 11/2017 | Siciliano et al. |
| 10,018,626 B2 | 7/2018 | Siciliano et al. |
| 10,495,638 B2 | 12/2019 | Siciliano et al. |
| 2002/0115198 A1 | 8/2002 | Nerenberg et al. |
| 2002/0146346 A1 | 10/2002 | Konecke |
| 2002/0172937 A1 | 11/2002 | Dave et al. |
| 2002/0187561 A1 | 12/2002 | Wong et al. |
| 2003/0021727 A1 | 1/2003 | Weyker et al. |
| 2003/0073248 A1 | 4/2003 | Roth et al. |
| 2003/0207442 A1 | 11/2003 | Markovsky et al. |
| 2003/0207466 A1 | 11/2003 | Po Lee |
| 2004/0002063 A1 | 1/2004 | Chan et al. |
| 2004/0018576 A1 | 1/2004 | DeMatteo et al. |
| 2004/0214253 A1 | 10/2004 | Paek et al. |
| 2004/0256230 A1 | 12/2004 | Yager et al. |
| 2005/0069962 A1 | 3/2005 | Archer et al. |
| 2005/0124077 A1 | 6/2005 | Cole et al. |
| 2005/0130294 A1 | 6/2005 | Randall et al. |
| 2005/0163658 A1 | 7/2005 | Wang et al. |
| 2005/0191620 A1 | 9/2005 | McDevitt et al. |
| 2005/0277202 A1 | 12/2005 | Fleming et al. |
| 2006/0246435 A1 | 11/2006 | Kempin et al. |
| 2006/0257941 A1 | 11/2006 | McDevitt et al. |
| 2006/0275851 A1 | 12/2006 | Emmert-Buck et al. |
| 2007/0004003 A1 | 1/2007 | Kitamoto et al. |
| 2007/0009911 A1 | 1/2007 | Joo et al. |
| 2007/0020768 A1 | 1/2007 | Rundstrom et al. |
| 2007/0098601 A1 | 5/2007 | Mabuchi et al. |
| 2007/0166199 A1 | 7/2007 | Zhou et al. |
| 2007/0190667 A1 | 8/2007 | Cole et al. |
| 2007/0202542 A1 | 8/2007 | Babu et al. |
| 2007/0218500 A1 | 9/2007 | Mikoshiba et al. |
| 2007/0224701 A1 | 9/2007 | Rosenstein |
| 2007/0292941 A1 | 12/2007 | Handique et al. |
| 2008/0013949 A1 | 1/2008 | Yoshikane et al. |
| 2008/0019866 A1 | 1/2008 | Paek et al. |
| 2008/0199851 A1 | 8/2008 | Egan et al. |
| 2008/0318342 A1 | 12/2008 | Durack et al. |
| 2009/0104715 A1 | 4/2009 | Katada et al. |
| 2009/0108013 A1 | 4/2009 | Van Der Velde et al. |
| 2009/0140471 A1 | 6/2009 | Fletcher et al. |
| 2009/0148933 A1 | 6/2009 | Battrell et al. |
| 2009/0272974 A1 | 11/2009 | Park et al. |
| 2009/0311668 A1 | 12/2009 | Cheng |
| 2010/0009387 A1 | 1/2010 | Cheng |
| 2010/0034699 A1 | 2/2010 | Chan |
| 2010/0233028 A1 | 9/2010 | Iwasaki et al. |
| 2010/0261206 A1 | 10/2010 | Choi et al. |
| 2010/0322823 A1 | 12/2010 | Surapaneni et al. |
| 2010/0323369 A1 | 12/2010 | Marlborough et al. |
| 2011/0027908 A1 | 2/2011 | Siciliano et al. |
| 2011/0117673 A1 | 5/2011 | Johnson et al. |

FOREIGN PATENT DOCUMENTS

| | | |
|---|---|---|
| CA | 2037521 A1 | 11/1991 |
| CA | 2060216 A1 | 9/1992 |
| CA | 2353920 A1 | 7/2000 |
| CN | 1979164 A | 6/2007 |
| CN | 1989413 A | 6/2007 |
| CN | 101339190 A | 1/2009 |
| CN | 101655494 A | 2/2010 |
| CN | 101726594 A | 6/2010 |
| DE | 19859912 A1 | 7/2000 |
| EP | 0067921 A1 | 12/1982 |
| EP | 0246900 A1 | 11/1987 |
| EP | 0284232 A1 | 9/1988 |
| EP | 0310406 A2 | 4/1989 |
| EP | 0414513 A2 | 2/1991 |
| EP | 0456303 A2 | 11/1991 |
| EP | 0473065 A2 | 3/1992 |
| EP | 0505636 A1 | 9/1992 |
| EP | 1045248 A2 | 10/2000 |
| EP | 1901067 A2 | 3/2008 |
| EP | 2031393 A1 | 3/2009 |
| EP | 2072135 A1 | 6/2009 |
| GB | 1244321 A | 8/1971 |
| KR | 20020097364 A | 12/2002 |
| WO | 8204263 A1 | 12/1982 |
| WO | 8808534 A1 | 11/1988 |
| WO | 9112366 A1 | 8/1991 |

(56) References Cited

FOREIGN PATENT DOCUMENTS

| WO | 9813519 | A1 | 4/1998 |
|---|---|---|---|
| WO | 9836821 | A1 | 8/1998 |
| WO | 0039581 | A2 | 7/2000 |
| WO | 02059299 | A2 | 8/2002 |
| WO | 02077013 | A2 | 10/2002 |
| WO | 03016902 | A1 | 2/2003 |
| WO | 2004097419 | A1 | 11/2004 |
| WO | 2005091878 | A2 | 10/2005 |
| WO | 2005119253 | A1 | 12/2005 |
| WO | 2007097917 | A1 | 8/2007 |
| WO | 2008154267 | A2 | 12/2008 |
| WO | 2009034563 | A2 | 3/2009 |
| WO | 2011014763 | A1 | 2/2011 |
| WO | 2011044574 | A1 | 4/2011 |

OTHER PUBLICATIONS

Notice of Allowance dated Jul. 27, 2017 in U.S. Appl. No. 15/141,141.
Office Action dated Apr. 4, 2017 in U.S. Appl. No. 15/161,753.
Office Action dated Apr. 12, 2017 in U.S. Appl. No. 15/141,141.
Notice of Allowance dated Mar. 14, 2018 in U.S. Appl. No. 15/161,690.
Notice of Allowance dated Jul. 15, 2019 in U.S. Appl. No. 15/383,330.
Fundamental Immunology, 3rd ed. (1993), ed. Paul, Raven Press, New York, N.Y.
Harlow et al., Antibodies: A Laboratory Manual, 1988, Cold Spring Harbor Laboratory Press, Cold Spring Harbor.
Jonio et al., Immunoglobulin Genes, 2nd Ed., 1995, Academic Press, San Diego.
Non-Final Office Action dated Jul. 6, 2015 from related U.S. Appl. No. 13/930,628.
Non-Final Office Action dated Nov. 3, 2015 from related U.S. Appl. No. 13/360,528.
Non-final Office Action dated Mar. 4, 2016 in U.S. Appl. No. 13/500,997.
Notice of Allowance dated Jan. 12, 2016 in related U.S. Appl. No. 13/930,628.
Notice of Allowance dated Mar. 16, 2016 for U.S. Appl. No. 13/789,002.
Notice of Allowance dated Jun. 10, 2016 in U.S. Appl. No. 13/360,528.
Non-Final Office Action dated Oct. 9, 2019 from related U.S. Appl. No. 15/800,300.

FIG.5
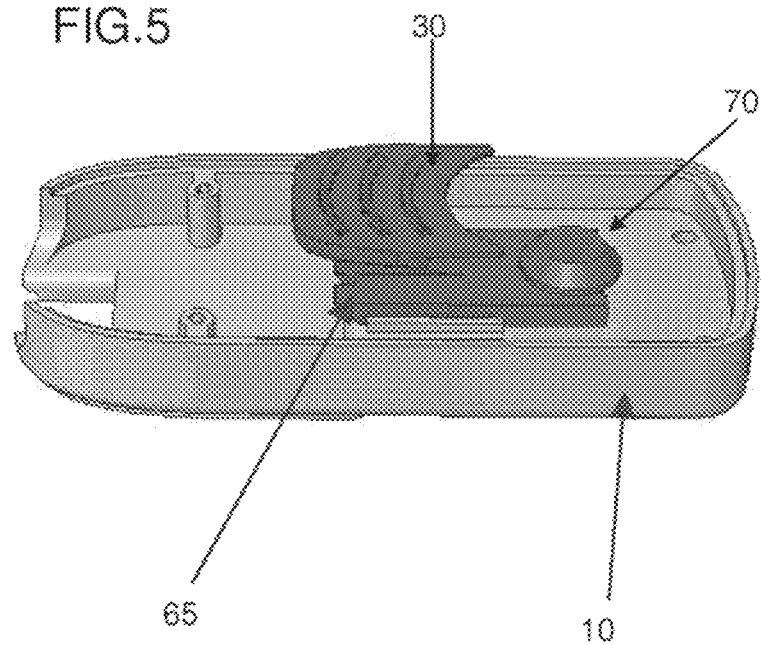
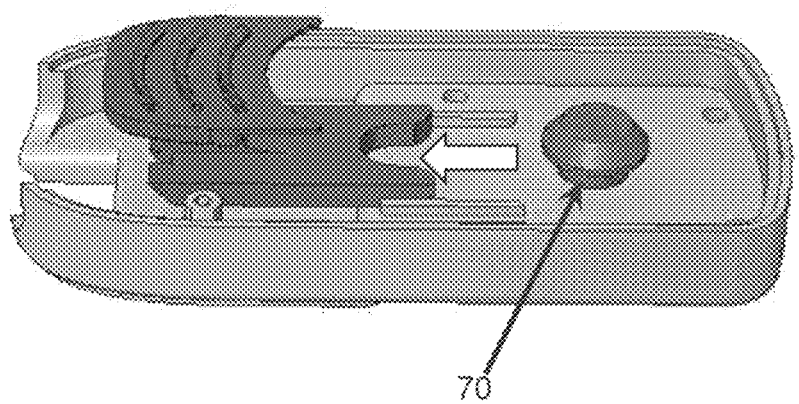
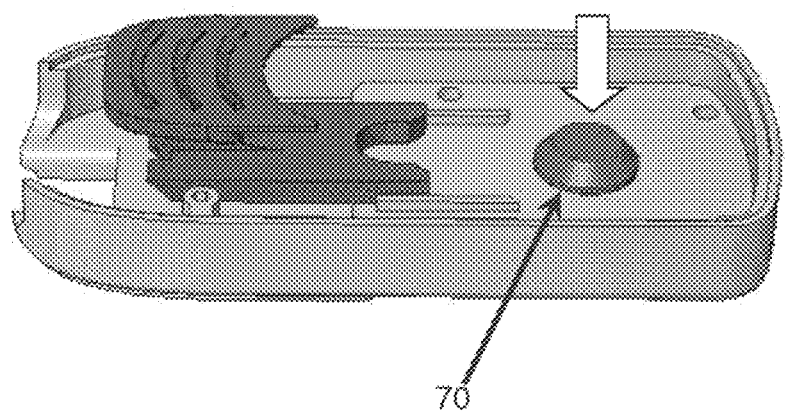

FIG. 27
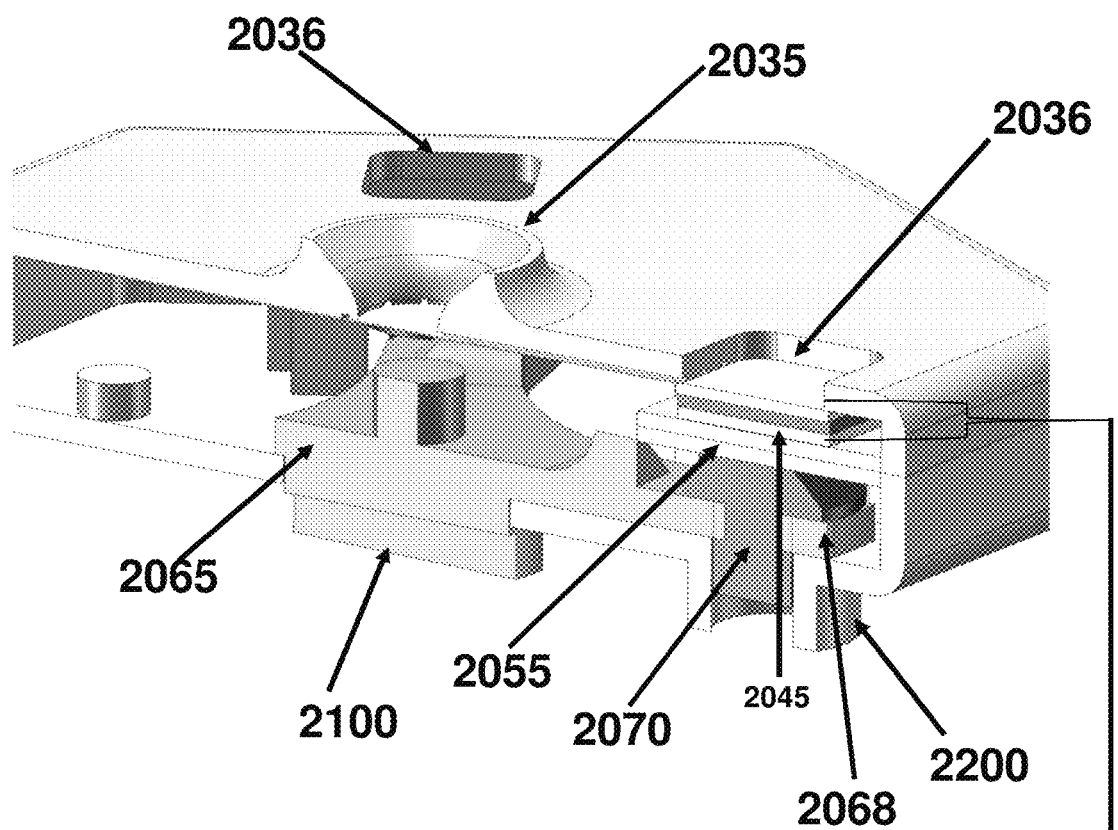
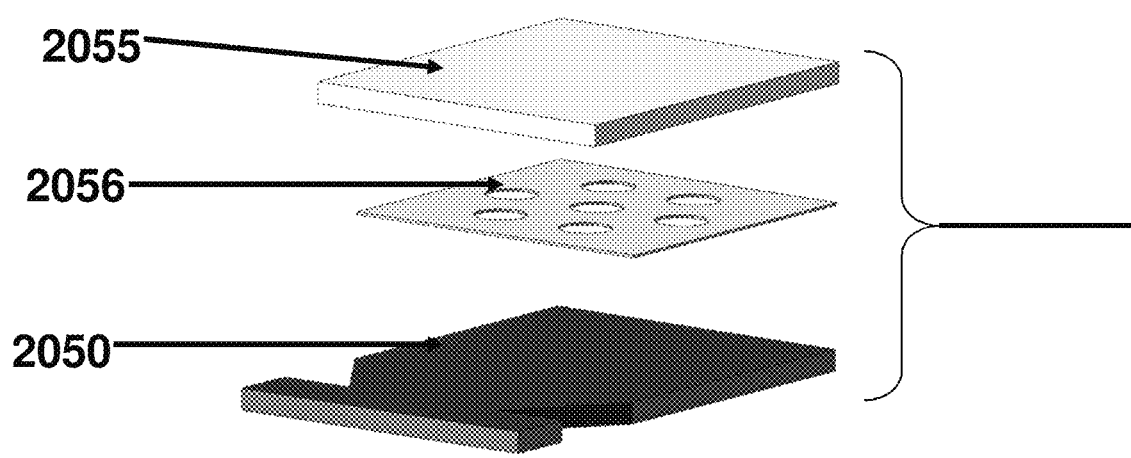

ANALYTE DETECTION DEVICES, MULTIPLEX AND TABLETOP DEVICES FOR DETECTION OF ANALYTES, AND USES THEREOF

CROSS-REFERENCE TO RELATED APPLICATIONS

This application is a continuation of U.S. patent application Ser. No. 13/360,528, filed Jan. 27, 2012, now U.S. Pat. No. 9,475,049, which claims priority to U.S. Provisional Application No. 61/436,733, filed Jan. 27, 2011, each of which are hereby incorporated by reference in its entirety. This application is also related to U.S. application Ser. No. 12/533,721, filed Jul. 31, 2009, now U.S. Pat. No. 8,012,770, U.S. application Ser. No. 13/221,116, filed Aug. 30, 2011, and PCT Application No. PCT/US10/52287, filed Oct. 12, 2010, each of which is hereby incorporated by reference in its entirety.

FIELD OF THE INVENTION

The present invention is directed, in part, to devices and assays for detecting one or more analytes and methods of using the same.

BACKGROUND OF THE INVENTION

Detection of analytes is important for many areas of scientific research, diagnostic use and therapeutic uses. There are several ways in which analytes can be detected. Various methods are described in U.S. Pat. Nos. 5,160,701, 5,141,850, PCT Publication WO 91/12336, U.S. Pat. Nos. 5,451,504, 5,559,041, European Patent Application No.: 0505636A1, PCT Publication No. WO 88/08534, European Patent Application No. 0284 232A1, U.S. Patent Application Publication No. 20070020768 and U.S. Pat. No. RE39664, each of which is hereby incorporated by reference in its entirety. The methods and devices available prior to the present invention may still require improvements in sensitivity or speed at which results can be obtained. These factors can be important where time is of the essence when attempting to determine the presence or absence of an analyte.

One such area is the area of detecting food borne pathogenic contaminants. Approximately, seventy-six million people in the United States become afflicted with a food borne illness. Of those seventy-six million, approximately, 325,000 will become violently ill, requiring hospitalization, and approximately 5,000 will die. The majority of food-borne illnesses are causes by *Salmonella, E. coli,* and *Campylobacter* costing approximately $35 billion dollars.

Current measures at ensuring a safe food supply involve a combination of local, state and federal authorities as well as an elaborate system of inspectors and surveillance networks. Food manufacturers are held to certain United States Department of Agriculture, United States Food and Drug Administration, and the National Marine Fisheries Service regulations that are enforceable by law. The USDA has created a system of health inspectors that is charged with performing daily meat, produce, and other consumable products inspections made or processed in manufacturing and processing facilities. These inspections have been created to involve a detailed statistical analysis to best ensure safety and sterility of food before it reaches the consumer. Moreover, the majority of the meat industry has adopted irradiation techniques to further demonstrate sterility of products. At a lower level, local and municipal health departments work to ensure that local distributors, restaurants, and retailers follow strict guidelines to ensure a safe food supply. However, despite this elaborate network, food-borne infections are still common.

Once an outbreak is strongly suspected, an investigation begins. A search is made for more cases among persons who may have been exposed. The symptoms and time of onset and location of possible cases are determined, and a "case definition" is developed that describes these typical cases. The outbreak is systematically described by time, place, and person. A graph is drawn of the number of people who fell ill on each successive day to show pictorially when it occurred. Calculating the distribution of cases by age and sex shows whom is affected.

Often the causative microbe is not known, so samples of stool or blood must be collected from ill people and sent to the public health laboratory to make a diagnosis. Each collection and sampling can cost upwards of $500 per test and often takes 2-4 days for analysis (CDC "Food-borne Infections").

Prior to the present invention, to identify the food or other source of the outbreak, the investigators first interview a few persons with the most typical cases about exposures they may have had in the few days before they got sick. In this way, certain potential exposures may be excluded while others that are mentioned repeatedly emerge as source possibilities. Combined with other information, such as likely sources for the specific microbe involved, hypotheses are then tested in a formal epidemiologic investigation. The investigators conduct systematic interviews about a list of possible exposures with the ill persons, and with a comparable group of people who are not ill. By comparing how often an exposure is reported by ill people and by well people, investigators can measure the association of the exposure with illness. Using probability statistics, the probability of no association is directly calculated.

As new food-borne problems emerge there is a need for novel devices and methods for detecting food borne pathogens. The present invention provides devices for the detection of analytes, such as analytes from food-borne bacteria, and fulfills the needs of having a device and assay with increased sensitivity and/or speed of detection. The present invention fulfills other needs as well as will be discussed herein.

SUMMARY OF THE INVENTION

The present invention provides devices for detecting analytes. In some embodiments, the present invention provides devices for detecting analyte(s) comprising: a housing comprising a first housing member and a second housing member, wherein the housing further comprises: an inlet; a first force member in contact with a force actuator outlet; a second force member contact with a force actuator outlet; a movable locking member contacting the first force member and the second force member; a first and second analyte detection membrane system comprising in the following order: a conjugate pad; an optional permeable membrane; a test membrane; and an absorbent member or series of absorbent members that are spaced apart or can be spaced apart in the absence of compression or force being applied to the analyte detection membrane system; and a first flexible or fixed attachment member attached to the movable locking member and the conjugate pad of the first analyte detection membrane system; a second flexible or fixed attachment member attached to the movable locking member and the conjugate pad of the second analyte detection membrane system; and a channel system or membrane that transports fluid from the inlet to the first and second analyte detection membrane systems; wherein at least a portion of each of the conjugate pad, permeable membrane, test membrane, and absorbent member are substantially parallel to each other; wherein the first and second analyte detection systems are capable of being compressed; wherein the first force member contacts the absorbent member of the first analyte detection membrane system and when the first force member is engaged applies pressure substantially perpendicular to the first analyte detection membrane system; and wherein the second force member contacts the absorbent member of the second analyte detection membrane system and when the second force member is engaged applies pressure substantially perpendicular to the second analyte detection membrane system. In some embodiments, the movable locking member comprises one or more movable locking member extensions that contacts the force member(s). In some embodiments, the extension that contacts the force member partially encircles the force member. In some embodiments, the channel system comprises a capillary channel system or absorbent material that transports fluid. In some embodiments, the channel system comprises two or more branches.

In some embodiments the present invention provides systems comprising a device described herein and a buffer container or a sample collector.

In some embodiments, the present invention provides kits comprising a device described herein and one or more of a positive control, a negative control, an instruction booklet, a buffer container, and a sample collector, or any combination thereof.

In some embodiments, the present invention provides methods of method of detecting an analyte using a device described herein. In some embodiments, the method comprises contacting a sample with the channel system of the device, wherein a portion of the sample flows to the conjugate pad of the first and second analyte detection membrane systems; and detecting a positive or negative reaction for the analyte, wherein a positive reaction indicates that the presence of the analyte. In some embodiments, the sample flows vertically through the membrane system.

In some embodiments, the present invention provides devices for detecting an analyte comprising: a sample inlet; an analyte detection cartridge receptacle; an analyte detection cartridge receptacle inlet; an optional conjugate pad remover; a pressure actuator controlled manually or by software; an optical reader; a display unit; a signal processing unit; an analyte detection cartridge receptacle positioning member; and optionally one or more of the following: a waste receptacle; and a motor or a lever connected to analyte detection cartridge receptacle positioning member. In some embodiments, the devices comprise at least one analyte detection membrane system.

In some embodiments of the devices described herein the analyte detection membrane system modulates the flow rate of a sample passing through the analyte detection membrane system.

In some embodiments, the present invention provides method of detecting an analyte using a device described herein comprising contacting a sample with the analyte detection membrane system, wherein the sample vertically flows through the analyte detection membrane system; and detecting the presence or absence of the analyte. In some embodiments, detecting the analyte comprises: a) detecting an optical signal from the analyte membrane system by the spectrometer; b) communicating the optical signal from the spectrometer to the signal processing unit; c) analyzing the optical signal by using the signal processing unit to determine the presence or absence of the analyte; and d) displaying a result on the display unit. In some embodiments, the optical signal is a signal in a spectrum chosen from infrared spectrum; near infrared spectrum; visible spectrum, x-ray spectrum, ultra-violet spectrum, gamma rays, or electromagnetic spectrum. In some embodiments, the optical signal is in the near-infrared spectrum.

In some embodiments of the present invention, the pressure actuator applies pressure to the analyte detection membrane system. In some embodiments, the flow rate of the sample through the analyte membrane system is regulated by the pressure actuator. In some embodiments, the signal processing unit controls the flow rate regulated by the pressure actuator. In some embodiments, the sample flows through the analyte detection membrane system at a constant rate. In some embodiments, the sample flows through the analyte detection membrane system at a variable rate. In some embodiments, the variable rate comprises at least one period of time where the flow rate is zero or substantially zero.

In some embodiments, the present invention provides devices for detecting an analyte comprising a force actuator; a force release; an analyte detection membrane system; an analyte detection membrane system receptacle; and an outlet.

In some embodiments of the present invention, the conjugate pad partially or completely dissolves after being contacted with a sample or a liquid. In some embodiments, the conjugate pad partially or completely dissolves to expose the test membrane. In some embodiments absorbent materials below the detection membrane may dissolve to modulate flow rate.

In some embodiments, the present invention provides uses of any device described herein for the detection of at least one analyte and/or a plurality of analytes.

BRIEF DESCRIPTION OF DRAWINGS

FIG. 5: Depicts some components of a representative device in various positions according to some embodiments of the present invention.

FIG. 27 depicts a cross-sectional view of a representative device according to some embodiments of the present invention.

DESCRIPTION OF EMBODIMENTS

Figure 1:
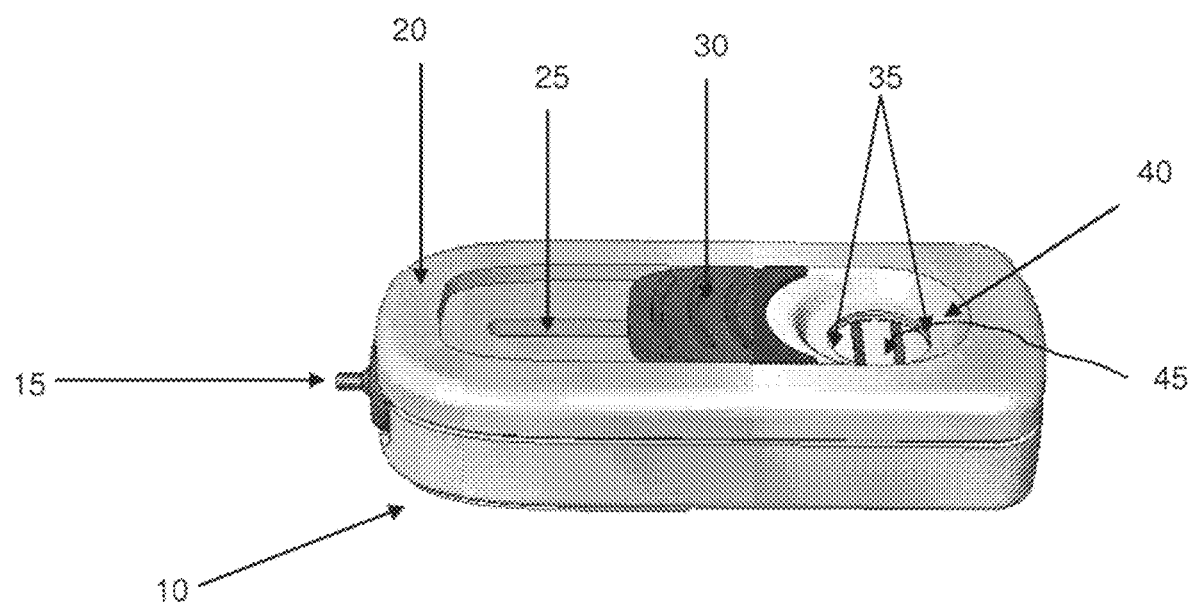
FIG. 1: Depicts a perspective view of a representative device according to some embodiments of the present invention.

The methods described herein can be used with any of the devices and systems described herein. The components of the devices can also be combined with any of the devices or systems described herein. For example, any of the devices described herein can be used in conjunction with a spectrometer and in the methods of using the spectrometer.

As used herein and unless otherwise indicated, the term "about" is intended to mean±5% of the value it modifies. Thus, about 100 means 95 to 105.

The present invention provides devices and methods for detecting analytes or other molecules. In some embodiments, the analyte can be an antigen that is recognized by an antibody. The analyte can also be other types of molecules including, but not limited to, those described herein and below. In some embodiments, devices in use chromatographic assays. In some embodiments, the assays use specifying binding assays to indicate the presence or absence of an analyte.

The term "sample" refers to as it is used herein and is meant any fluid medium or liquid. In some embodiments, samples may be used which are high in dissolved solids without further processing and samples containing high solids (non-dissolved) may be introduced, in some embodiments, through a filter or used in conjunction with additional manual steps. Samples may also be non-filtered or purified prior to being used in a device described herein. Samples may be a liquid, a suspension, extracted or dissolved sample, or a supercritical fluid. Some flow properties must exist in the sample or extract to allow flow through the devices and systems described herein. Examples of samples include, but are not limited to, blood, food swabs, food extracts, food suspensions, saliva, biological fluid, PCR reactions and the like. A "food suspension" refers to raw or cooked food that has been placed or suspended in a solution. The food solution may be mixed, vortexed or blended.

The devices can be used to detect analytes such as, but not limited to, antigens, nucleic acid molecules encoded by a cell, virus, bacteria or other type of microorganism. Nucleic acid molecules can be detected as described herein by using the devices described herein in combination with other known methods, such as amplification methods. The amplification methods can be used to amplify the amount of nucleic acid molecules present in a sample to facilitate the detection of the analyte. Other types of analytes that can be detected using the devices and methods described herein include but are not limited to antigens, antibodies, receptors, ligands, chelates, proteins, enzymes, nucleic acids, DNA, RNA, pesticides, herbicides, inorganic or organic compounds or any material for which a specific binding reagent may be found. The surfaces can be used with multiple analytes and the designation of specific interaction can be made clear with the use of surface patterning to resolve differing analytes. The antigen can be anything recognized by an antibody or capture reagent, or labeled to be recognized by an antibody or capture reagent. The membrane detection systems described herein can be used to detect analytes, such as amplicons or products of PCR reactions. As used herein, the term "amplicon" refers to an amplification product such as a nucleic acid that is amplified by a PCR reaction or other amplification reaction or method. The amplification product can be detected indirectly through the use of antibodies or other capture reagent systems as they are described herein.

For example, in some embodiments, the amplicon is referred to as a PCR product. The PCR reactions can be labeled such that they are detectable either by another antibody or antibody like system, such as but not limited to Biotin-Avidin/Streptavidin system, digoxigenin systems, hapten systems, BRDU labeling of DNA, intercalating agents that label DNA, labeled dNTPS, and the like can also be used where the PCR products are labeled. Where used herein, the term antigen membrane detection system or the like can be substituted with an analyte detection system. Likewise, where the term antigen is used herein, the term analyte can also be used and is encompassed by the embodiments disclosed herein. The analyte can also be referred to as a target molecule. This target molecule, which can, for example, but not limited to, be a nucleic acid (single stranded or double stranded) can be recognized or detected with an antibody or other capture reagent system, such as those described herein. The nucleic acid molecule can be labeled with a biotin label or other type of label that can be detected using methods known to one of skill in the art.

For example, in some embodiments, a PCR reaction is performed with hapten and/or biotin labeled DNA or RNA primers with homology to an analyte nucleic acid sequence, such as but not limited to, a toxin gene and/or a toxin molecule (e.g. Shiga toxin) from a meat sample. The sample, however, can be any sample, and the analyte can be any other type of analyte described herein. Following amplification with the primers, the PCR sample can be added directly to a device, such as those described herein. In some embodiments, the conjugate pad will comprise a capture reagent that is attached or coated onto a detectable label, such as a nanoparticle. For example, the conjugate pad can comprise streptavidin coated nanoparticles and the detection membrane can comprise of anti-hapten antibodies so that a positive test result is only possible if the specific labeled amplicon is present in the PCR reaction. This test can be used to detect Shiga toxin expressing *E. coli* present in a food matrix. That is one strand end of the PCR product is labeled with biotin and the strand of the PCR product is labeled with hapten such that a positive result is only obtained if both strands are present.

Accordingly, embodiments are provided that disclose methods of detecting an analyte, such as a virus, bacteria, or other type of microorganism nucleic acid molecule present in a sample. The method can also be used to confirm the absence of a nucleic acid molecule present in a sample. In some embodiments, the method comprises releasing the nucleic acid molecules from the organism, virus, bacteria. The nucleic acid molecule, which can be DNA or RNA or fragment thereof, can be released by heating or otherwise denaturing the cell or virus or the cell containing the viral genome. The nucleic acid molecules can be further purified.

In some embodiments, the nucleic acid molecule, which is target analyte is not further extracted or purified from the crude extract. For example, in some embodiments, a meat sample is processed with a solution that allows the nucleic acid molecule to be detected. In some embodiments, the nucleic acid molecule is not further purified away from other cellular components, such as but not limited to, proteins, nuclear membrane, cell membrane, and the like.

In some embodiments, the method comprises amplifying the target nucleotide sequence. The nucleotide sequence can be amplified using any known method. The amplification method can be done using, but not limited to, DNA primed DNA or RNA primed RNA, or a combination of both an RNA/DNA duplex. In some embodiments, the nucleic acid, target sequence is unique or otherwise a specific characteristic of said the cell, virus/bacteria/micro-organism/nucleic acid analyte. In some embodiments, the method of amplification comprises the use of a pair of first and second primer sequences defining the 5' and 3' ends of the target sequence. In some embodiments, the first primer sequence is labeled with a first label and the second primer sequence is labeled with a second label such that any amplification of the target sequence generates an amplicon (e.g. PCR product) labeled with both first and second labels. In some embodiments, the method comprises transferring or diluting an amount of the amplification product in a suitable buffer solution comprising, for example, particles (e.g. microparticles, nanoparticles, metal sols, and the like) labeled with a first agent that specifically binds to the first label and allowing the first agent to bind to the first label present. In some embodiments, the undiluted or diluted amplicon is placed directly onto a vertical flow device or flow through assay described herein. In some embodiments, at least a portion of the buffered, undiluted, or diluted amplicon product is applied to a vertical flow device or flow through assay that allows the constituents of the amplicon flow vertically through a device, such as those described herein, wherein on the detection membrane, a test region and a control region are present. In some embodiments, the test region comprises a second agent that specifically binds to the second label and the control region comprises a control agent. In some embodiments, the method comprises detecting any binding of constituents of the amplicon at the test region and at the control region.

In some embodiments, a method as above is provided that comprises treating the sample so as to cause release of nucleic acid from any of said cell, virus/bacteria/micro-organism/nucleic acid analyte present in the sample. In some embodiments, the method comprises amplifying more than one target nucleotide sequences (including, but not limited to, DNA primed DNA or RNA primed RNA, or a combination of both an RNA/DNA duplex) present within the nucleic acid molecules, the target sequence(s) being unique or otherwise characteristic of the cell, virus/bacteria/micro-organism/nucleic acid analyte. In some embodiments, the method comprises the use of a pair of first and second primer sequences defining the 5' ends of the different target sequences labeled with first and second distinct labels and the 3' primers labeled with a third label such as biotin that each amplicon of the different target sequence has a unique 5' label and share the same 3' label generates amplicons labeled with either first and third labels or second and third labels. The labels can be, for example, biotin. The different target sequences may share homology or identity but are not 100% identical in length and/or sequence.

In some embodiments, the method comprises transferring or diluting an amount of the amplification product of step in a suitable solution (e.g. buffer solution) with streptavidin or avidin to and then transferring amplicon reaction onto vertical flow device or flow through assay described herein. In some embodiments, the method comprises applying at least a portion of the product to a vertical flow device or flow through assay that allows constituents of the product flow vertically through the device. In some embodiments, as described herein the device comprises particles that bind the first label, for example on the conjugate pad, and wherein on the detection membrane, a test region and a control region exist, wherein the test region comprises a second agent which specifically binds to the second label and the control region being provided with a control agent thereby leading to positive detection only in the presence of both target amplicons. In some embodiments, the method comprises detecting any binding of constituents of the amplicon reaction step (ii & iii) at the test region and at said control region. In some embodiments, the strands of the PCR or amplification product are labeled with the nucleotides that are incorporated into the amplification product. For example, one strand may have one label and the other strand may have a different strand. Therefore, the analyte is only detected if both labels are present. As with all embodiments described herein, the labels can be radioactive or non-radioactive. Examples of labels include, but are not limited to, biotin, hapten (DNP), digoxigenin (DIG), fluorescein (FITC), Rhodamine (Rho), Bromodexoyuridine (BRDU), and the like. Other intercalating agents that intercalate with nucleic acid molecules can also be used. Other examples of labels are described herein or are known to one of skill in the art and can be used in the methods and devices described herein.

Various embodiments disclosed herein describe the amplification of a nucleic acid analyte. The analyte can be amplified using any method including, but not limited to, PCR, nested PCR, or PCR sewing. In some embodiments, the nucleic acid analyte is amplified with at least one primer that is a degenerate primer sequence. In some embodiments, both of the primers are target specific. In some embodiments, one and/or both of the primers are specific to a target or toxin specific genes selected from *E. Coli*, Listeriaceae, Enterobacteriaceae, Staphylococcaceae, Legionellaceae, Pseudomonadaceae, and Campylobacteraceae. In some embodiments, the primers are genus-specific. The genus can be the genus described herein. In some embodiments, the sequences of the primers are specific to *Listeria monocytogenes*.

Analyte nucleic acid targets can be from any type of bacteria, virus, or other type of microorganism. Examples include, but are not limited to, *E. Coli*, Listeriaceae, Enterobacteriaceae, Staphylococcaceae, Legionellaceae, Pseudomonadaceae, Campylobacteraceae, and the like In some embodiments of the methods, the sequences of the first and second primer sequences are specific to a species, and wherein the amplifying step further comprises amplification of a further target nucleotide sequence through the use of a pair of third and fourth primer sequences defining the 5' and 3' ends of said further target sequence, said third and fourth primer sequences being specific for the genus to which the said species belongs and labeled with, respectively, third and fourth labels, such that any amplification of the target sequence and further target sequence generates a species specific amplicon labeled with both first and second labels and/or a genus-specific amplicon labeled with both the third and fourth labels, wherein said third and fourth labels either both differ from the first and second labels or, alternatively said third label is the same or functionally equivalent to the first label and said fourth label differs from the first and second labels. Examples of these methods are also disclosed in US Patent Application Publication 2010/0136531 A1, which is hereby incorporated by reference in its entirety.

In some embodiments, the sequences of the first and second primer sequences are specific to a first genus, and wherein the amplifying step further comprises amplification of a further target nucleotide sequence through the use of a pair of third and fourth primer sequences defining the 5' and 3' ends of the further target sequence, the third and fourth primer sequences being specific for a second genus and labeled with, respectively, third and fourth labels, such that any amplification of the target sequence and further target sequence generates an amplicon labeled with both first and second labels and/or an amplicon labeled with both the third and fourth labels, wherein said third and fourth labels either both differ from the first and second labels or, alternatively, said third label is the same or functionally equivalent to the first label and said fourth label differs from the first and second labels. The genus can be the same or a different genus than the first primer pair is detecting. For example, one genus can be *E. coli* and the other genus can be *salmonella*.

In some embodiments, methods for the detection of a nucleic acid in a sample is provided, the method comprising heating said sample at a temperature in the range of 85 to 100° C. or boiling in the presence or absence of detergents such as SDS or Tween so as to cause release of nucleic acid from any cell or other nucleic acid-containing structure present in the sample; amplifying a target nucleotide sequence present on said nucleic acid, comprising the use of a pair of first and second primer sequences defining the 5' and 3' ends of said target sequence, said first primer sequence being labeled with a first label and said second primer sequence being labeled with a second label such that any amplification of the target sequence generates an amplicon labeled with both first and second labels; diluting an amount of the amplification product in a suitable buffer solution comprising particles labeled with a first agent which specifically binds to the first label and allowing said first agent to bind to said first label present; applying at least a portion of the buffered or untreated product of step (iii) to a vertical flow device as described herein or vertical flow through assay that allows constituents of the buffered product to flow vertically through the device, wherein on the detection (e.g. test) membrane, a test region and a control region, the test region comprising a second agent that specifically binds to the second label and the control region comprising a control agent; and detecting any binding of constituents of the amplification product at the test region and at the control region. The presently described method can also be modified in accordance with the other embodiments disclosed herein.

The present invention provides analysis of analytes by using vertical flow. Vertical flow allows the analyte and/or the sample to flow through the layers/membranes of the analyte detection membrane system. By "through layers" or "through membranes" is meant to refer to the sample flowing through the layers and vertically across the layers. In some embodiments, the sample does not flow, or substantially flow, horizontally or laterally across the different layers/membranes.

The term "pressure actuator" and "force actuator" can be used interchangeably and refer to a component that can exert, for example, pressure through the application of force. A force actuator can also be referred to as a force member. Examples of include, but are not limited to, various force members that are described herein. Other examples include, but are not limited to, pistons or other solid support structures. The force actuator's position relative to another component can be raised, lowered, or moved laterally. The position of the force actuator can be controlled manually or through a signal processing unit (e.g. computer). The ability to control the position of the force actuator can be used to regulate the force (e.g. pressure) being applied to another component, such as, but not limited to, an analyte detection membrane system. By regulating the force applied to the membrane system the flow rate of the sample can be regulated. The force can be used to keep the flow rate of the sample through the membrane system constant or the flow rate can be variable. The flow rate can also be stopped and allow the sample to dwell on different layers of the membrane system. For example, the sample's flow rate can be zero or near zero when the sample contacts the conjugate pad. After resting on the conjugate pad the flow rate can be increased by modulating the pressure being applied by the force actuator. The sample can then through the entire membrane system, or the force being applied can be modulated to allow the sample to dwell (rest) on another layer of the membrane system. Because the force can be precisely regulated, either manually or by using a signal processing unit (e.g. computer) the flow rate can be modified at any point as the sample vertically flows through the membrane system. The flow rate can also be regulated based upon the absorbency of the membranes in the membrane system and/or the number of the membranes of the system, or hydrophobic membranes, or dissolving materials. Based upon the absorbency the flow rate can be modulated (e.g. increased or decreased). Additional forces can also be employed to move sample through the system including, but not limited to vacuum force and centrifugal force. Membranes or layers may dissolve as the sample flows through the system. The dissolving of one or more layers can be used to modulate the flow rate of the sample.

The flow rate can be measured in any units including but not limited to μl/min or μl/sec, and the like. The flow rate during a dwell can be, for example, 0 μl/sec, or less than 1, 0.9, 0.8, 0.7, 0.6, 0.5, 0.4, 0.3, 0.2, or 0.1 μl/sec or μl/min. In some embodiments, the flow rate is limited by capillary action and/or is not being enhanced by pressure or vacuum force. The flow rate can be monitored manually or by a signal processing unit (e.g. computer) and regulated by the same. The flow rate can be regulated and monitored by well known and routine methods known to one of skill in the art in addition to those described herein. In some embodiments, the flow rate is about 0 to 1 ml/min, about 0-10 ml/min, about 1-9 ml/min, about 1-8 ml/min, about 1-7 ml/min, about 1-6 ml/min, about 1-5 ml/min, about 1-4 ml/min, about 1-3 ml/min, about 1-2 ml/min, about 0.5-1.5 ml/min, about 1-1.5 ml/min, or about 0.5-1 ml/min. In some embodiments, the flow rate is about 1, 2, 3, 4, 5, 6, 7, 8, 9, or 10 ml/min. In some embodiments, the flow rate is at least 1, 2, 3, 4, 5, 6, 7, 8, 9, or 10 ml/min. In some embodiments, the flow rate is 1, 2, 3, 4, 5, 6, 7, 8, 9, or 10 ml/min. As discussed herein, the flow rate can be modulated or tuned to a specific flow rate. In some embodiments, The tuning of the flow rate allows for an increase in sensitivity The term "capture reagent" refers to a reagent, for example an antibody or antigen binding protein, capable of binding a target molecule or analyte to be detected in a biological sample. A capture reagent may also be, for example, an oligonucleotide or a peptoid. The capture reagent can also be a small molecule or protein, such as biotin, avidin, streptavidin, hapten, digoxigenin, BRDU, single and double strand nucleic acid binding proteins or other intercalating agents, and the like, or molecules that recognize and capture the same. These non-limiting examples of systems can be used as capture reagents and to detect the presence or absence of an analyte.

The term "detecting" or "detection" is used in the broadest sense to include qualitative and/or quantitative measurements of a target analyte.

The terms "attached" or "attachment" can include both direct attachment or indirect attachment. Two components that are directly attached to one another are also in physical contact with each other. Two components that are indirectly attached to one another are attached through an intermediate component. For example, Component A can be indirectly attached to Component B if Component A is directly attached to Component C and Component C is directly attached to Component B. Therefore, in such an example, Component A would be said to be indirectly attached to Component B.

The term "isolated" refers to a molecule that is substantially separated from its natural environment. For instance, an isolated protein is one that is substantially separated from the cell or tissue source from which it is derived.

The term "purified" refers to a molecule that is substantially free of other material that associates with the molecule in its natural environment. For instance, a purified protein is substantially free of the cellular material or other proteins from the cell or tissue from which it is derived. The term refers to preparations where the isolated protein is sufficiently pure to be analyzed, or at least 70% to 80% (w/w) pure, at least 80%-90% (w/w) pure, 90-95% pure; and, at least 95%, 96%, 97%, 98%, 99%, or 100% (w/w) pure.

The terms "specific binding," "specifically binds," and the like, mean that two or more molecules form a complex that is measurable under physiologic or assay conditions and is selective. An antibody or antigen binding protein or other molecule is said to "specifically bind" to a protein, antigen, or epitope if, under appropriately selected conditions, such binding is not substantially inhibited, while at the same time non-specific binding is inhibited. Specific binding is characterized by a high affinity and is selective for the compound, protein, epitope, or antigen. Nonspecific binding usually has a low affinity. Binding in IgG antibodies for example is generally characterized by an affinity of at least about $10^{-7}$ M or higher, such as at least about $10^{-8}$ M or higher, or at least about $10^{-9}$ M or higher, or at least about $10^{-10}$ or higher, or at least about $10^{-11}$ M or higher, or at least about $10^{-12}$ M or higher. The term is also applicable where, e.g., an antigen-binding domain is specific for a particular epitope that is not carried by numerous antigens, in which case the antibody or antigen binding protein carrying the antigen-binding domain will generally not bind other antigens. In some embodiments, the capture reagent has a Kd equal or less than $10^{-9}$M, $10^{-10}$ M, or $10^{-11}$ M for its binding partner (e.g. antigen). In some embodiments, the capture reagent has a Ka greater than or equal to $10^9 M^{-1}$ for its binding partner.

Capture reagent can also refer to, for example, antibodies. Intact antibodies, also known as immunoglobulins, are typically tetrameric glycosylated proteins composed of two light (L) chains of approximately 25 kDa each, and two heavy (H) chains of approximately 50 kDa each. Two types of light chain, termed lambda and kappa, exist in antibodies. Depending on the amino acid sequence of the constant domain of heavy chains, immunoglobulins are assigned to five major classes: A, D, E, G, and M, and several of these may be further divided into subclasses (isotypes), e.g., IgG1, IgG2, IgG3, IgG4, IgA1, and IgA2. Each light chain is composed of an N-terminal variable (V) domain (VL) and a constant (C) domain (CL). Each heavy chain is composed of an N-terminal V domain (VH), three or four C domains (CHs), and a hinge region. The CH domain most proximal to VH is designated CH1. The VH and VL domains consist of four regions of relatively conserved sequences named framework regions (FR1, FR2, FR3, and FR4), which form a scaffold for three regions of hypervariable sequences (complementarity determining regions, CDRs). The CDRs contain most of the residues responsible for specific interactions of the antibody or antigen binding protein with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3. CDR3 is the greatest source of molecular diversity within the antibody or antigen binding protein-binding site. H3, for example, can be as short as two amino acid residues or greater than 26 amino acids. The subunit structures and three-dimensional configurations of different classes of immunoglobulins are well known in the art. For a review of the antibody structure, see Antibodies: A Laboratory Manual, Cold Spring Harbor Laboratory, Eds. Harlow et al., 1988. One of skill in the art will recognize that each subunit structure, e.g., a CH, VH, CL, VL, CDR, and/or FR structure, comprises active fragments. For example, active fragments may consist of the portion of the VH, VL, or CDR subunit that binds the antigen, i.e., the antigen-binding fragment, or the portion of the CH subunit that binds to and/or activates an Fc receptor and/or complement.

Non-limiting examples of binding fragments encompassed within the term "antigen-specific antibody" used herein include: (i) an Fab fragment, a monovalent fragment consisting of the VL, VH, CL and CH1 domains; (ii) an F(ab')2 fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which consists of a VH domain; and (vi) an isolated CDR. Furthermore, although the two domains of the Fv fragment, VL and VH, are coded for by separate genes, they may be recombinantly joined by a synthetic linker, creating a single protein chain in which the VL and VH domains pair to form monovalent molecules (known as single chain Fv (scFv)). The most commonly used linker is a 15-residue $(Gly4Ser)_3$ peptide, but other linkers are also known in the art. Single chain antibodies are also intended to be encompassed within the terms "antibody or antigen binding protein," or "antigen-binding fragment" of an antibody. The antibody can also be a polyclonal antibody, monoclonal antibody, chimeric antibody, antigen-binding fragment, Fc fragment, single chain antibodies, or any derivatives thereof. The capture reagent or antibody can also be a VHH region, a bi-specific antibody, a peptide fragment comprising an antigen binding site, or a compound that binds to an antigen of interest.

These antibodies are obtained using conventional techniques known to those skilled in the art, and the fragments are screened for utility in the same manner as intact antibodies. Antibody diversity is created by multiple germline genes encoding variable domains and a variety of somatic events. The somatic events include recombination of variable gene segments with diversity (D) and joining (J) gene segments to make a complete VH domain, and the recombination of variable and joining gene segments to make a complete VL domain. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation. Based on the estimated number of germline gene segments, the random recombination of these segments, and random VH-VL pairing, up to $1.6 \times 10^7$ different antibodies may be produced (Fundamental Immunology, 3rd ed. (1993), ed. Paul, Raven Press, New York, N.Y.). When other processes that contribute to antibody diversity (such as somatic mutation) are taken into account, it is thought that upwards of $1 \times 10^{10}$ different antibodies may be generated (Immunoglobulin Genes, 2nd ed. (1995), eds. Jonio et al., Academic Press, San Diego, Calif.). Because of the many processes involved in generating antibody diversity, it is unlikely that independently derived monoclonal antibodies with the same antigen specificity will have identical amino acid sequences.

Antibody or antigen binding protein molecules capable of specifically interacting with the antigens, epitopes, or other molecules described herein may be produced by methods well known to those skilled in the art. For example, monoclonal antibodies can be produced by generation of hybridomas in accordance with known methods. Hybridomas formed in this manner can then be screened using standard methods, such as enzyme-linked immunosorbent assay (ELISA) and Biacore analysis, to identify one or more hybridomas that produce an antibody that specifically interacts with a molecule or compound of interest.

As an alternative to preparing monoclonal antibody-secreting hybridomas, a monoclonal antibody to a polypeptide of the present invention may be identified and isolated by screening a recombinant combinatorial immunoglobulin library (e.g., an antibody phage display library) with a polypeptide of the present invention to thereby isolate immunoglobulin library members that bind to the polypeptide. Techniques and commercially available kits for generating and screening phage display libraries are well known to those skilled in the art. Additionally, examples of methods and reagents particularly amenable for use in generating and screening antibody or antigen binding protein display libraries can be found in the literature.

The term "capture reagent" also includes chimeric antibodies, such as humanized antibodies, as well as fully humanized antibodies. In some embodiments the capture reagent is a Goat anti-*E. coli* 0157:H7 antibody Cat #: 70-XG13 (Fitzgerald Industries); *E. coli* 0157:H7 mono Cat #: 10-E13A (Fitzgerald Industries); *E. coli* 0157:H7 Cat #: 10C-CR1295M3 (Fitzgerald Industries); *E. coli* 0157:H7 mono Cat #: 10-E12A (Fitzgerald Industries); or Goat anti-mouse IgG Cat #: ABSE-020 (DCN).

In some embodiments, the devices of the present invention comprise a housing comprising a first housing member and a second housing member. In some embodiments, the first and second housing members can be constructed as a single unit. The housing can comprise an inlet opening. The inlet opening allows the introduction of a sample onto the chromatographic assay. In some embodiments, the first housing member comprises the inlet opening. The inlet opening can be of sufficient size to handle an appropriate amount of volume of a solution that is added to the device. In some embodiments, the size of the opening is large enough to handle about 0.1 to 3 ml, about 0.1 to 2.5 ml, about 0.5 to 2.0 ml, about 0.1 to 1.0 ml, about 0.5 to 1.5 ml, 0.5 to 1.0 ml, and 1.0 to 2.0 nil.

In some embodiments, the housing comprises a conjugate pad, a permeable membrane, a test membrane, and/or an absorbent member. In some embodiments, the housing comprises an analyte detection membrane system. In some embodiments, the analyte detection membrane system comprises a conjugate pad, a permeable membrane, a test membrane, and an absorbent member. In some embodiments, the analyte detection membrane system is free of a permeable membrane. In some embodiments, the analyte detection membrane system comprises in the following order: a conjugate pad, a permeable membrane, a test membrane, and an absorbent member.

As used herein, the term "conjugate pad" refers to a membrane or other type of material that can comprise a capture reagent. The conjugate pad can be a cellulose acetate, cellulose nitrate, polyamide, polycarbonate, glass fiber, membrane, polyethersulfone, regenerated cellulose (RC), polytetra-fluorethylene, (PTFE), Polyester (e.g. Polyethylene Terephthalate), Polycarbonate (e.g., 4,4-hydroxy-diphenyl-2,2'-propane), Aluminum Oxide, Mixed Cellulose Ester (e.g., mixture of cellulose acetate and cellulose nitrate), Nylon (e.g., Polyamide, Hexamethylene-diamine, and Nylon 66), Polypropylene, PVDF, High Density Polyethylene (HDPE)+nucleating agent "aluminum dibenzoate" (DBS) (e.g. 80 u 0.024 HDPE DBS (Porex)), and HDPE. Examples of conjugate pads also include, Cyclopore® (Polyethylene terephthalate), Nucleopore® (Polyethylene terephthalate), Membra-Fil® (Cellulose Acetate and Nitrate), Whatman® (Cellulose Acetate and Nitrate), Whatman #12-S (rayon)), Anopore® (Aluminum Oxide), Anodisc® (Aluminum Oxide), Sartorius (cellulose acetate, e.g. 5 μm), and Whatman Standard 17 (bound glass). The conjugate pad can also be made of a material that dissolves after coming into contact with a sample or other liquid. The dissolving of the conjugate pad can be performed so that other layers of the systems described herein can be revealed or exposed for either visual inspection (e.g. detection of an analyte) or for spectrometer inspection (e.g. detection of an analyte by a spectrometer).

In some embodiments, the conjugate pad or test membrane comprises a capture reagent. In some embodiments, the conjugate pad or test membrane is contacted with the capture reagent and then allowed to dry. The conjugate pad or test membrane can also comprise other compositions to preserve the capture reagent such that it can be stably stored at room temperature or under refrigeration or freezing temperatures. In some embodiments, the conjugate pad or test membrane is soaked with a buffer prior to the capture reagent being applied. In some embodiments, the buffer is a blocking buffer that is used to prevent non-specific binding. In some embodiments, the buffer comprises Borate, BSA, PVP40 and/or Tween-100, or any mixture thereof. In some embodiments, the buffer is 10 mM Borate, 3% BSA, 1% PVP40, and 0.25% Tween-100. In some embodiments the capture reagent is applied to the pad or membrane in a solution comprising trehalose and sucrose. In some embodiments, the capture reagent is applied to the pad, membrane, or both, in a solution comprising trehalose, sucrose and phosphate and/or BSA. In some embodiments, the capture reagent is applied in a solution that is 5% trehalose, 20% sucrose, 10 mM phosphate, and 1% BSA.

In some embodiments, the pad or membrane (e.g. conjugate pad or test membrane) comprises about 0.5 to about 5.0 μg of a capture reagent, about 1 to about 3 μg of a capture reagent, about 1 to about 2 μg of a capture reagent, about to 2 to about 3 μg of a capture reagent, about 1.5 μg of a capture reagent, 2.5 μg of a capture reagent, or about 2.7 μg of a capture reagent.

In some embodiments, the removable member contacts a first surface of the conjugate pad and the adhesive member contacts a second surface of the conjugate pad.

In some embodiments, the device comprises an adhesive member. The adhesive member can comprises an adhesive member inlet that allows the sample to flow through the conjugate pad and contact the test membrane. In some embodiments, the adhesive member inlet is the same size or shape as the removable member inlet. In some embodiments, the adhesive member inlet is a different size or shape as the removable member inlet. In some embodiments, the inlets in the adhesive member are the same shape but have different areas. Inlets with different areas would be considered to have different sizes. The adhesive member can be made up of any substance suitable for adhering one member or membrane to another member or membrane. In some embodiments, the adhesive member is impermeable to liquid. In some embodiments, the adhesive member contacts the removable member.

In some embodiments, the permeable membrane is attached to or adhered to a test membrane. In some embodiments, the permeable membrane is laminated onto the test membrane. The permeable membrane can be a membrane of any material that allows a sample, such as a fluid sample, to flow through to the test membrane. Examples of test membrane include, but are not limited to, nitrocellulose, cellulose, glass fiber, polyester, polypropylene, nylon, and the like. In some embodiments, the permeable membrane comprises an opening. The opening can be present to allow visualization or detection of the test membrane. In some embodiments, the opening in the permeable membrane is substantially the same size as the inlet opening in the housing. Examples of permeable membranes include, but are not limited to, Protran BA83, Whatman, and the like.

As used herein, the "test membrane" refers to a membrane where detection of a binding partner to a capture reagent occurs. The "test membrane" may also be referred to as a "detection membrane." Test membranes include, but are not limited to a nitrocellulose membrane, a nylon membrane, a polyvinylidene fluoride membrane, a polyethersulfone membrane, and the like. The test membrane can be any material that can be used by one of skill in the art to detect the presence of a capture reagent's binding partner (e.g. analyte or epitope). The test membrane can also comprise a capture reagent. In some embodiments, the test membrane is contacted with a capture reagent and the capture reagent is allowed to dry and adhere to the test membrane. Examples of test membranes include, but are not limited to Protran BA83, Whatman, Opitran BA-SA83, and 0.22 μm white plain (Millipore Product No. SA3J036107). Test membranes may also be comprised of nanoparticle matrices to which capture reagents are bound. Nanocrystals can be arranged into 2D sheets and 3D matrices with materials such as, but not limited to, carbon based particles, gold or metal alloy particles, co-polymer matrices, as well as monodisperse semiconducting, magnetic, metallic and ferroelectric nanocrystals. The test membrane can comprise a plurality of capture reagents. In some embodiments, the test membrane comprises 1, 2, 3, 4, 5, 6, 7, 8, 9, or 10 capture reagents. In some embodiments, the test membrane comprises a plurality of areas each with a different capture reagent. In some embodiments, the plurality of areas do not completely overlap or coincide with one another. By using a plurality of capture reagents, multiple binding partners (e.g. epitopes or analytes) can be detected.

In some embodiments, the device or housing also comprises an absorbent member. The absorbent member can also be referred to as a "wick pad" or "wicking pad." The absorbent member absorbs the fluid that flows through the device when the sample is applied to the device and provides for the wicking force that aids in the flow of the sample when it is applied to the device. By "absorbent member" is meant to refer to a material that has a capacity to draw (wick) and retain solution away from a surface that the material is in contact with. Use of a combination of material of increasing or decreasing absorbance can allow for control of sample movement.

The absorbent member can be any material that can facilitate the flow of the sample through the conjugate pad and to the test membrane. Examples of absorbent members include, but are not limited to cellulose, super absorbent polymers, glass fiber pads (e.g. C083 (Millipore)), and the like. In some embodiments, the housing comprises a plurality (e.g. 2 or more) of absorbent members. In some embodiments, the housing comprises 2, 3, 4, or 5 absorbent members. In some embodiments, the device comprises one absorbent member. In some embodiments, the absorbent member comprises one or more membranes up to 10 individual membranes, and each membrane may be the same material or a different material. In some embodiments, the device consists of only 1 membrane that is an absorbent member. The absorbent member(s) can be separated from the other members in the analyte membrane detection system. They can be separated by spacers. These spacers can be either between the members or along the edges of the members so that each membrane or layer of the system is not in contact with one another until the layers are compressed.

Figure 16:
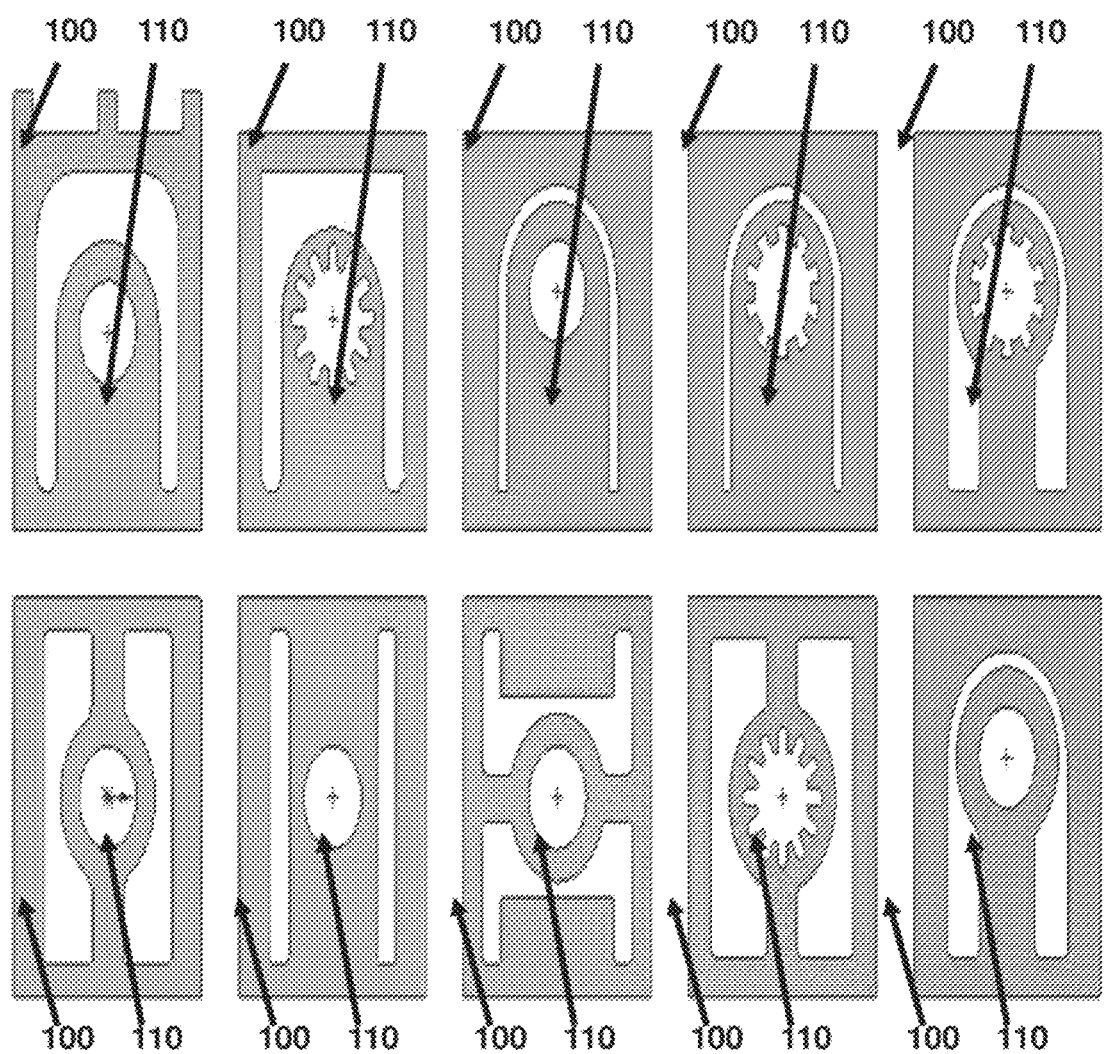
FIG. 16 depicts representative force members for a representative device according to some embodiments of the present invention.

In some embodiments, the device comprises a force member. FIG. 16 depicts some embodiments, but non-limiting examples, of force members. The force member can, in some embodiments, be used to apply pressure or to compress the other components of the analyte detection membrane system against one another. The force member can be made out of any material including, but not limited to stainless steel. The stainless steel can be laser cut such that it can act as a clip. The force member acts to apply pressure to the membrane system. The force member is not limited to a clip, but rather can be any shape (see, Figures for non-limiting examples) that can apply pressure to the membrane system (e.g. nanoparticle matrices) and piston like structures strategically placed within the assembly. In some embodiments, the force member is a piston. The force member can be used to apply pressure or to compress the other components of the analyte detection membrane system against one another. In some embodiments, the force member can comprise a shaft and a head. The force member can have a mushroom type shape where the head is wider than the shaft. In some embodiments, the head is narrower than the shaft. The force member comprising a head and a shaft can be a single unit or can be made up of multiple parts that contact one another to form the force member. For example, the head could be one unit that can be separated from the shaft. Upon assembly the head and shaft are contacted with one another to make the force member. In another example, the head and shaft are one cohesive unit and are manufactured together and not as separate parts that are later assembled to form the force member. The force member allows the device to work with vertical flow as opposed to relying upon lateral flow.

In some embodiments, the force member contacts a surface of the absorbent member. In some embodiments, the force member contacts a surface of the absorbent member and a surface of the removable layer. In some embodiments, the force member compresses the membrane detection system from above and below the membrane detection system. For example, in some embodiments, the force member can sandwich all the layers of the membrane detection system. In some embodiments the force member is attached to a support member. See, for example, FIG. 17C showing a component (110) attached to component (100).

In some embodiments, the device comprises, in the following order, a removable member, a conjugate pad, and an adhesive member.

The device can also comprise a support member. The support member, in some embodiments, contacts a surface of the absorbent member. The support member can also have a support member inlet. The inlet can be the same size and/or shape as the inlet in the removable member and/or the adhesive member. In some embodiments, the support member comprises an inlet that is a different size and/or shape as the inlet in the removable member and/or the adhesive member. The support member can be made from any material including, but not limited to, plastic. In some embodiments, the second housing member serves as the support member.

The devices described herein can be used in assays to detect the presence of a capture reagent's binding partner. For example, an analyte can be detected by an antibody using the devices of the present invention. The devices of the present invention employ vertical flow. "Vertical flow" refers to the direction that the sample flows across the different membranes and members present in the device. Vertical flow refers to a sample flowing through the membrane (e.g. top to bottom) as opposed to lateral flow, which refers to a sample flowing across (e.g. side to side) a membrane, pad or absorbent member. In a lateral flow device the membranes and pads sit horizontally adjacent to one another substantially on the same plane. In a vertical flow device each membrane or pad is substantially parallel or completely parallel to each other and occupy substantially different spatial planes in the device. The membranes and pads may occupy similar planes when they are compressed or put under pressure. In some embodiments, at least a portion of each member, membrane, or pad is layered on top of each other. In some embodiments, at least a portion of each layer of member, membrane, or pad is substantially parallel to each other. In some embodiments, at least a portion of each layer is in a different spatial plane than each other layer.

To allow vertical flow to occur efficiently, in some embodiments and when present, the conjugate pad, permeable membrane, test membrane and the absorbent member are substantially parallel to each other. In some embodiments, the conjugate pad, permeable membrane, test membrane and the absorbent member are present in different spatial planes. In some embodiments, the housing also comprises a hydrophobic membrane that can slow or stop the vertical flow of the sample. The hydrophobic membrane can be in contact with the test membrane, which would allow the sample to dwell or rest upon the test membrane. The dwell can allow for increased sensitivity and detection. The vertical flow is modulated by the pressure that is applied to the membranes, pads, and/or members. In some embodiments, the pressure is applied perpendicular to the test membrane and/or the conjugate pad. The pressure can be applied so that the conjugate pad is compressed against the housing. The compression against the housing can be such that the conjugate is in direct contact with the housing, O-ring, or collar, or through an intermediate so that the conjugate pad and the test membrane are compressed against one another.

The force member can apply pressure that is substantially perpendicular to the test membrane. The pressure facilitates the vertical flow. The pressure allows each layer of the membrane stack to be in contact with another layer. The pressure can also be relieved to stop the flow so that the test sample can dwell or rest upon the test membrane, which can allow for greater sensitivity. The pressure can then be reapplied to allow the vertical flow to continue by allowing the sample to flow into the absorbent member(s). The force member can apply pressure such that the conjugate pad contacts a portion of the housing (e.g., first or second housing members or removable layer). In some embodiments, the conjugate pad contacts the housing when it is not under the pressure being exerted by the force member but upon the force member exerting pressure the conjugate pad is compressed against a portion of the housing.

In some embodiments, the conjugate pad contacts the perimeter of the inlet opening. The inlet opening can also comprise a collar or other similar feature, such as an O-ring. In some embodiments, the conjugate pad contacts the perimeter of a collar and/or an O-ring. In some embodiments, the conjugate pad is capable of being compressed against the perimeter of the inlet opening, which can include, in some embodiments, a collar and/or an O-ring.

"Capable of being compressed against the perimeter of the inlet opening" refers to a membrane or pad (e.g. conjugate pad) being compressed either directly in contact with the perimeter of the inlet opening or being compressed against another layer or material (e.g. membrane) that is in contact with the perimeter of the inlet opening.

In some embodiments, the conjugate pad is not in direct physical contact with the housing but is in fluid contact with the housing. "Fluid Contact" means that if a sample is applied to the device through the inlet opening or other opening the fluid will contact the conjugate pad. In some embodiments, the conjugate pad can be separated from the housing by another membrane, such as a permeable membrane, where the other membrane is in direct physical contact with the housing or in direct physical contact with the collar or O-ring. When the sample is applied to the device the fluid can contact the other membrane first and then contact the conjugate pad. This is just one example of the conjugate pad being in fluid contact with the housing. There are numerous other embodiments where the conjugate pad is not in direct physical contact with the housing, the collar, or the O-ring, but is in fluid contact with the housing.

The force member can apply any pressure that is sufficient to facilitate vertical flow across the different membrane layers. In some embodiments, the layers of the device (e.g. conjugate pad, permeable membrane, test membrane, and absorbent member) are compressed under a force chosen from about 5 lbf to 100 lbf, about 5 lbf to 50 lbf, about 10 lbf to 40 lbf, about 15 lbf to 40 lbf, about 15 lbf to 25 lbf, or about 30 lbf to 40 lbf. In some embodiments, the layers of the device (e.g. conjugate pad, permeable membrane, test membrane, and absorbent member) are compressed under a force chosen from about 1 lbf to 100 lbf, about 1 lbf to 50 lbf, about 1 lbf to 5 lbf, about 1 lbf to 10 lbf, about 1 lbf to 15 lbf, about 1 lbf to 20 lbf, about 1 lbf to 30 lbf, or about 1 lbf to 25 lbf. The force can also compress a hydrophobic or impermeable membrane as well if one is present in the device.

In some embodiments, the force member contacts a first surface of an absorbent member. In some embodiments, a conjugate pad contacts a test membrane. In some embodiments, a first surface of a test membrane contacts a permeable membrane. In some embodiments, a second surface of the test membrane contacts a second surface of the absorbent pad. In some embodiments, the device comprises a hydrophobic membrane, and, for example, the hydrophobic membrane contact a second surface of the test membrane. In some embodiments, the hydrophobic membrane contacts a first surface of the absorbent pad. In some embodiments, a conjugate pad contacts an adhesive member. In some embodiments, a test membrane contacts an adhesive member.

In some embodiments, a first surface of the conjugate pad contacts the housing and a second surface of the conjugate pad contacts a first surface of the permeable membrane, wherein the second surface of the permeable membrane contacts a first surface of the test membrane, wherein a second surface of the test membrane contacts a first surface of the absorbent pad, wherein a second surface of the absorbent pad contacts the force member. In some embodiments, the first surface of the conjugate pad contacts a perimeter of the inlet opening of said housing. In some embodiments, the first surface of the conjugate pad contacts a perimeter of a collar or an O-ring.

In some embodiments, a first surface of the conjugate pad contacts the housing and a second surface of the conjugate pad contacts a first surface of the adhesive member, wherein the second surface of the adhesive member contacts a first surface of the test membrane, wherein a second surface of the test membrane contacts a first surface of the absorbent pad, wherein a second surface of the absorbent pad contacts the support member. In some embodiments, the first surface of the conjugate pad contacts a perimeter of the inlet. In some embodiments, the first surface of the conjugate pad contacts a perimeter of a collar or an O-ring.

The device can also comprise an attachment member. In some embodiments, the attachment member is flexible or made from a flexible material. In some embodiments, the attachment member is fixed or made from a non-flexible material. Depictions shown in the figures as having flexible attachment members can easily be adapted to be used with a fixed attachment member or one that is made from a non-flexible material. The fixed attachment member can be, for example, a hinge and the like that can, for example, contact the conjugate pad or another layer or membrane of the system and can mediate its displacement. The fixed attachment member, such as, but not limited to, a fixed hinge or other compressible material that acts like a hinge and can return to a shape or dimension upon compression release. The attachment member can be capable of displacing the conjugate pad.

The flexible material can be, for example, an elastic or elastomer material. An attachment member can be, for example, attached to a conjugate pad and/or a hydrophobic membrane. The attachment member can also be attached to any membrane or member of the device. Examples of attachment members include, but are not limited to, elastomer band, rubber band, spring, and the like. In some embodiments, the attachment member can be made of a shape memory material. The attachment member makes it possible to create a delay between moving the locking member and moving the conjugate pad or any other type of membrane or pad that the attachment member is attached to. In some embodiments, the movement of the pad or membrane does not happen at the same time as the sliding button or locking member is moved. Not being bound to any particular theory, as the sliding button or locking member is moved energy is accumulated in the attachment member and this energy is used to pull on a pad or membrane that it is attached to the attachment member after the pressure has been released. In some embodiments, the locking member is moved away from the force member (i.e., the force member no longer contacts the locking member) before the conjugate pad is moved or removed. The conjugate pad, in some embodiments, is moved once the compression or pressure being exerted by the force member is completely removed.

The attachment member can also be attached to either a sliding button or locking member. The attachment member can be attached through any means such as, adhesives, staples, tying, and the like to the other components. In some embodiments, the membrane or pad has notches in the membrane or pad that allow the attachment member to attach to the membrane or pad. A non-limiting example can be seen in FIG. 9. FIG. 8B shows a non-flexible attachment member (60) from a side view that is part of a sliding member. The non-flexible attachment member shows one layer of the membrane detection system (e.g. conjugate pad (50)) inserted into it. When the attachment member is moved by the sliding member the conjugate pad is moved, which would expose the test (i.e. detection) membrane so that a positive or negative result could be visualized or detected as described herein.

In some embodiments, the housing comprises a locking member. The locking member can be a slidable locking member that can move within the device. The locking member can be used to lock the force member in a position such that the force created by the force member upon the different layers is maintained. The locking member is, for example, locking the force member in place so that the pressure cannot be relieved unless the locking member is moved to allow the force member to change positions (i.e. lowered). The locking member, can for example, fit under the head of the force member, which would keep the force member in the raised position. The locking member can also be situated so that it keeps the force member in a particular position (e.g. raised or lowered). The locking member can be made of any material including, but not limited to, plastic and the like. The locking member can, for example, contact the force member either directly or indirectly through another component that prevents the force member from releasing the pressure. In some embodiments, the locking member contacts the force member to compress the conjugate pad.

The locking member can also contact the attachment member such that movement of the locking member will move the attachment member, any other membrane (e.g. conjugate pad, hydrophobic membrane, test membrane, or absorbent member) or other component that is attached to the attachment member. For example, if the locking member is moved to relieve the pressure of the force member thereby allowing the force member to change positions (e.g. from raised to a lower position), the movement of the locking member will also deform/accumulate energy into the attachment member so it can move the membrane or pad once the pressure has been sufficiently reduced. When the conjugate pad is attached to the attachment member and the locking member is moved this will also move the conjugate pad once the pressure has been sufficiently reduced. In some embodiments, the pressure is completely removed. The conjugate pad can be, for example, moved such that it is removed from the device. In some embodiments, the conjugate pad is moved to reveal the test membrane through the inlet opening. The amount of the test membrane that is revealed will depend upon the type of detection that is used. For a visual detection more of the test membrane may need to be revealed in the inlet opening. For a non-visual, e.g. fluorescent, near-infrared, infrared, radioactive or chemiluminescent detection, less or none of the test membrane may need to be revealed. In some embodiments, the conjugate pad is moved so that it no longer can be seen or detected through the inlet opening. In some embodiments, the movement of the conjugate pad can create another opening other than the inlet opening to visualize or detect the test membrane. In some embodiments, the conjugate pad is dissolved to visualize or detect the test membrane (e.g. detection of the analyte). The conjugate pad can be made of a dissolvable material such that when the conjugate pad comes into contact with the sample or another solution the conjugate pad partially or completely dissolves.

In some embodiments, the attachment member is also attached to the impermeable or hydrophobic membrane. When the attachment member is moved the movement will also move or remove the impermeable or hydrophobic membrane. As discussed herein, the presence of the impermeable or hydrophobic membrane can allow the test sample to dwell or rest upon the test membrane by slowing or stopping the vertical flow. When the impermeable or hydrophobic membrane is moved or removed, either by its attachment to the attachment member or through other means, the vertical flow is no longer impeded or inhibited.

In some embodiments, the housing comprises a sliding button. A sliding button can also be referred to as a sliding member. The sliding button can cross the inner and outer surfaces of the housing. In some embodiments, the sliding button or sliding member protrudes to an outer surface of the housing. In some embodiments, the sliding button is attached either directly or indirectly to the locking member. When the sliding button is attached (directly or indirectly) to the locking member the movement of the sliding button also moves the locking member. The attachment member in some embodiments can be attached to the sliding button. In some embodiments, the attachment member is attached to both the sliding button and the locking member. The sliding button and the locking member can also be constructed as a single unit.

In some embodiments, any one or more of the inlets comprise an opening chosen from a range of about 0.2 to about 20 $cm^2$. In some embodiments, any one or more of the inlets is about 1 to about 2 cm in diameter. In some embodiments, any one or more of the inlets is about 1 or about 1.5 cm in diameter. In some embodiments, any one or more of the inlets is about 1, about 2, about 3, about 4, or about 5 cm in diameter. In some embodiments, where there is more than one inlet, the inlets can be different sizes or the same sizes. The size of each inlet is independent of one another. In some embodiments of the devices and systems described herein, the devices or systems comprises 1, 2, 3, 4, or 5 inlets. In some embodiments of the devices and systems described herein, the devices or systems comprises at least 1, 2, 3, 4, or 5 inlets.

In some embodiments, the inlet opening comprise an opening chosen from a range of about 0.2-20 $cm^2$. In some embodiments, the inlet opening is about 1 to about 2 cm in diameter. In some embodiments, the inlet opening is about 1 or about 1.5 cm in diameter. In some embodiments, the inlet opening is about 1, about 2, about 3, about 4, or about 5 cm in diameter.

In some embodiments, a device for detecting an analyte comprises a first member and a second member. In some embodiments, the first member and second member are in contact with each other. In some embodiments, the first member comprises one or more inlets. In some embodiments, between the first and second member is an analyte detection membrane system. In some embodiments, the analyte detection membrane system between the first and second member comprises a conjugate pad, an adhesive member, a test membrane and an absorbent member. In some embodiments, the analyte detection membrane system comprises in the following order: a conjugate pad; an adhesive member; a test membrane; and an absorbent member. As discussed herein, in some embodiments, at least a portion of each of the conjugate pad, test membrane, and absorbent member are substantially parallel to each other. In some embodiments, at least a portion of each of the conjugate pad, test membrane, and absorbent member are in a different spatial plane.

In some embodiments, the analyte detection membrane system is compressed between the first and second member (e.g. of the force member). In some embodiments, the analyte detection membrane system is compressed between a plane formed by the first member and a plane formed by the second member wherein the planes formed by the first and second members are substantially parallel to each other and the analyte detection membrane system. In some embodiments, the planes are parallel to each other and the analyte detection membrane system. In some embodiments, the first and second members that compress the analyte detection membrane system is a force member. For example, the force member can be referred to as comprising a first and second member to create the force that compresses the analyte detection membrane system.

In some embodiments, the first and second member are attached to one another along an edge of the first member that is parallel to an edge of the second member. In some embodiments, the first and second member are attached by a spring, hinge, and the like. The manner by which the first and second member are attached is not limited and can be by any structure that enables the analyte membrane system to be compressed between the first and second member. In some embodiments, the first and second member are contiguous with one another and form a clip. Examples of clips (e.g. force members) are shown throughout the present application (e.g. FIG. 16). The clip, can be for example cut from metal or other type of material that allows the first member to be flexible such that the analyte detection membrane system can be inserted between the first and second members. In some embodiments, the first member is removable.

In some embodiments, the first member is attached or in contact with the conjugate pad, wherein the movement or removal of the first member moves the conjugate pad or removes the conjugate pad from the device. In some embodiments, the conjugate pad is removable.

In some embodiments, the conjugate pad is removed from the device comprising the first and second member by removing only the conjugate pad.

In some embodiments, the conjugate pad comprises a tab. The tab can be used to remove or to facilitate the removal of the conjugate pad.

Figure 18A:
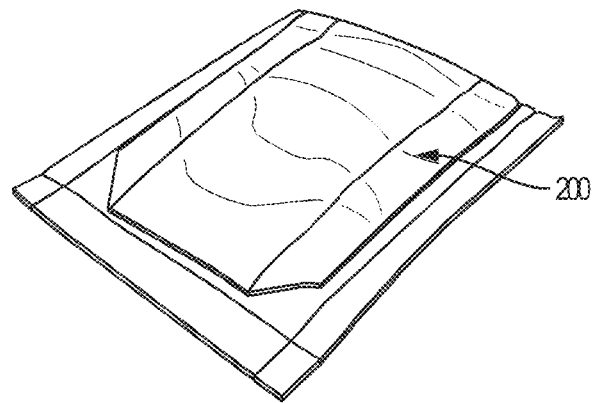
FIGS. 18A-18C depict a representative device according to some embodiments of the present invention.
Figure 18B:
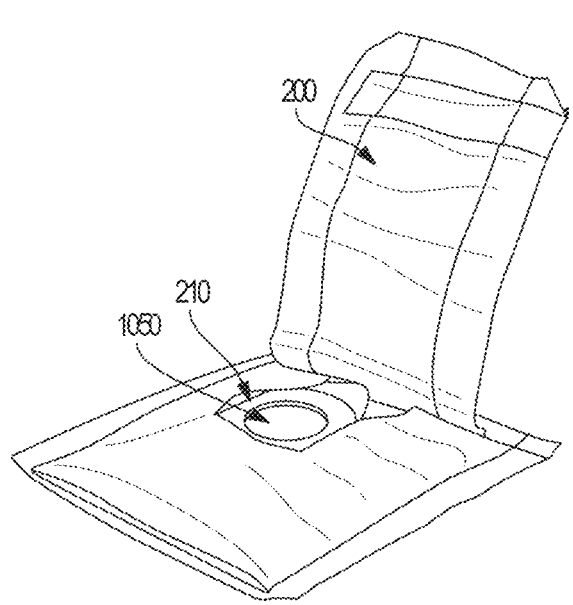
Figure 18C:
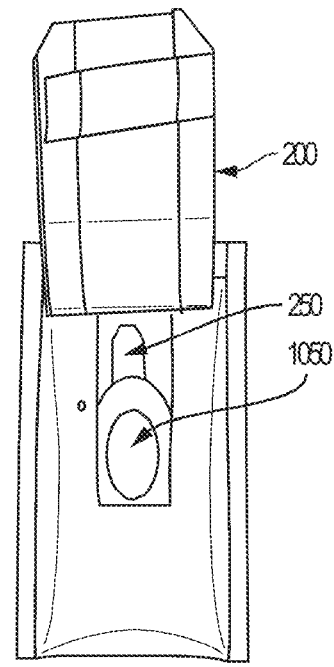
Figure 19A:
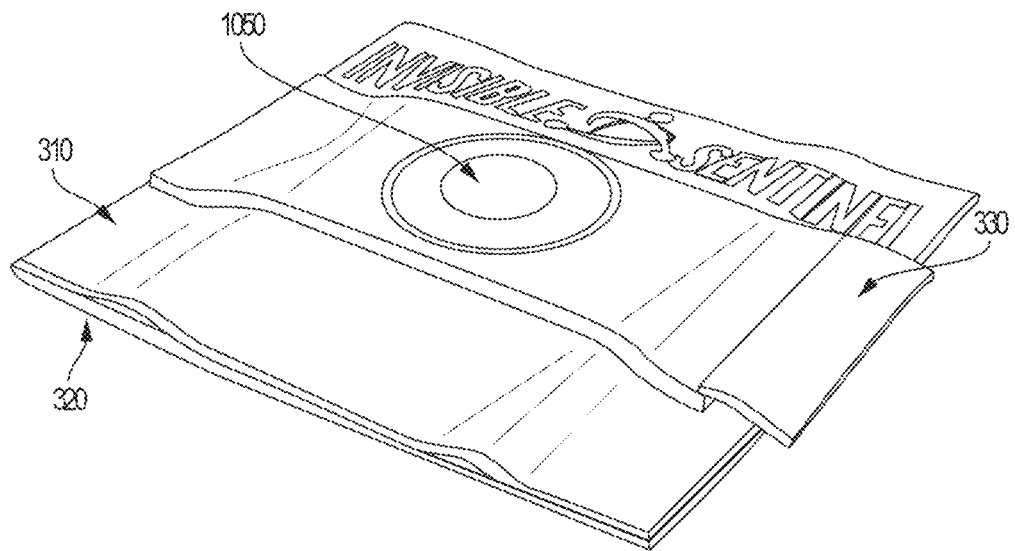
FIGS. 19A-19B depict a representative device according to some embodiments of the present invention.
Figure 19B:
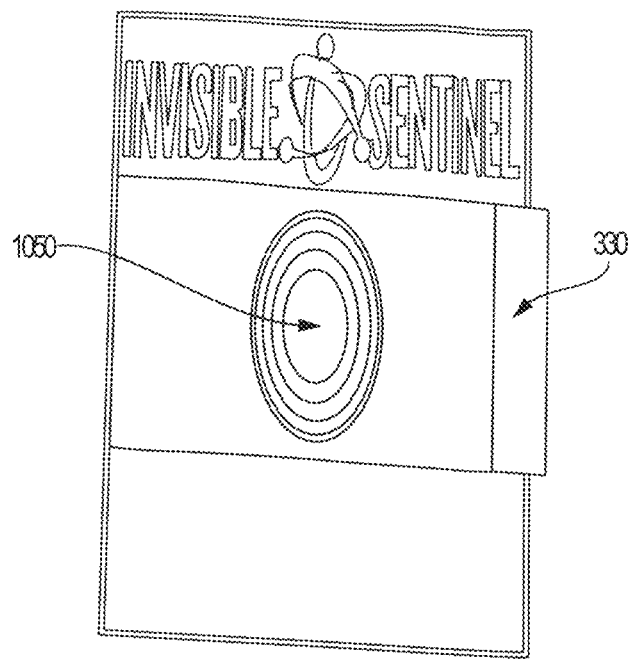

In some embodiments, the devices described herein are placed in a container. In some embodiments, the container is a pouch or a bag. In some embodiments, the container comprises an inlet. In some embodiments, the container comprises a removable or movable member or layer that when moved or removed exposes the inlet allowing the sample to be applied to the analyte detection membrane system. Examples of a removable or movable member or layer includes, but is not limited to, a flap or tab. A flap or tab, for example, is shown in FIGS. 18 and 19. In some embodiments, the removable layer or movable layer can also act as a seal for the container. The seal can protect the conjugate pad and/or the analyte detection membrane system.

In some embodiments of the devices and systems described herein, the removable or movable layer is in contact with or attached to the conjugate pad.

In some embodiments, a device for detecting an analyte comprises a first outer member and a second outer member comprising a first inner member and a second inner member, wherein the first inner member and second inner member are in contact with each other. In some embodiments, the first outer member comprises an inlet. In some embodiments, the first inner member comprises an inlet. In some embodiments, the first outer member and the first inner member comprise an inlet. In some embodiments, between the first and second inner members is an analyte detection membrane system. In some embodiments, the device comprises a conjugate pad. In some embodiments, the device lacks a conjugate pad. In some embodiments, the analyte detection membrane system comprises a test membrane and an absorbent member and optionally a conjugate pad. In some embodiments, the analyte detection membrane system comprises in the following order a test membrane and an absorbent member. In some embodiments, at least a portion of each of the optional conjugate pad, test membrane, and absorbent member are substantially parallel to each other. In some embodiments, as discussed above, the analyte detection membrane system is compressed between the first inner member and second inner member. In some embodiments, the device and/or system comprises an adhesive member as described herein. In some embodiments, the device comprises a filtration membrane. In some embodiments, the filtration membrane can be within the analyte detection membrane system. In some embodiments, the a first surface of the filtration membrane contacts a surface of the first inner member and a second surface of the filtration membrane contacts another membrane or member of the analyte detection membrane system. In some embodiments, a second surface of a filtration membrane contacts a surface of a test membrane. The filtration membrane can be any material as described herein. For example, the filtration membrane, in some embodiments, can be the same materials that can be a conjugate pad, test, membrane, absorbent member, and the like. In some embodiments, the filtration membrane is a glass fiber pad.

In some embodiments, where the conjugate pad is not present within the device or the system, the conjugate is supplied as a liquid or as a material that can be dissolved in a liquid (e.g. water, buffered solution, saline, and the like). The conjugate can be supplied in a separate container (e.g. tube) and be provided with a device or system described herein. Where the conjugate is supplied in a container the conjugate is incubated with the sample before the sample is applied to the analyte detection membrane system. The sample can be produced by any method and/or as described herein. For example, a piece of meat can be swabbed or wiped and to produce a test sample. The test sample can then be incubated or contacted with the conjugate to produce a test sample-conjugate mixture. This mixture can then be applied to the analyte detection membrane system as described herein using a device and/or system as described herein. In some embodiments, the test sample-conjugate mixture is applied directly to the test membrane. In some embodiments, the test sample-conjugate mixture is filtered or passes through another membrane prior to contacting the test membrane.

In some embodiments, the analyte detection membrane system is compressed between the first and second inner members. In some embodiments, the analyte detection membrane system is compressed between a plane formed by the first inner member and a plane formed by the second inner member wherein the planes formed by the first inner member and the second inner member are substantially parallel to each other and the analyte detection membrane system. In some embodiments, the planes are parallel to each other and the analyte detection membrane system. In some embodiments, the planes are substantially parallel to the first and second outer members.

In some embodiments of the devices described herein and throughout, the conjugate pad is not compressed by the first and second inner members or by the force members described herein.

In some embodiments, the first outer member comprises a removable or movable tab. In some embodiments, the conjugate pad is attached to said first outer member. In some embodiments, the conjugate pad is attached to the removable or movable tab. In some embodiments, the first outer member and second outer member form a container and the container encapsulates the first and inner second member. In some embodiments, the container is a pouch, bag (e.g. sealable (e.g. zipper, adhesive, and the like) or any other type of container that can encompass the analyte detection membrane system and that is compressed between the first and second inner members.

In some embodiments, the container comprises a removable or movable tab. The removable or movable tab can be any shape and can be completely removable or removed to an extent that exposes the inlet. In some embodiments, the tab when moved or removed removes or moves the conjugate pad. The conjugate pad can be moved, for example, a sufficient distance so that the results of the test membrane can be analyzed (e.g. visualized).

In some embodiments, a first surface of the conjugate pad is in contact with the first outer member and a second surface of the conjugate pad is in contact with the first inner member.

In some embodiments, the first and second inner members are attached to one another along an edge of the first inner member that is parallel to an edge of the second inner member. In some embodiments, the first and second inner members are attached by a spring, hinge, and the like. The manner by which the first and second inner members are attached is not limited and can be by any structure that enables the analyte membrane system to be compressed between the first and second member. In some embodiments, the first and second inner members are contiguous with one another and form, for example, a clip. Examples of clips are shown throughout the present application. The clip, can be for example, cut from metal or other type of material that allows the first inner member to be flexible such that the analyte detection membrane system can be inserted between the first and second members. In some embodiments, the first inner member is removable.

As discussed herein, the devices and systems can comprise a removable or movable layer (e.g. tab). The removable or movable layer can be removed or moved by manual force, such as, but not limited to, pealing or tearing. The removable or movable layer can also be removed or moved by mechanical force. The manner by which the removable or movable layer is moved can by any means. Examples of a removable or movable layer includes but is not limited to, tabs, flaps, and the like. As discussed herein, this flap or tab can act as a seal and the like.

As discussed herein, the conjugate pad can comprise an analyte specific capture reagent. In some embodiments, the conjugate pad comprises a plurality of analyte specific capture reagents. In some embodiments, the conjugate pad comprises 1, 2, 3, 4, or 5 analyte specific capture reagents. The analyte can be any molecule that can be specifically recognized by a capture reagent. Examples of analytes include a polynucleotide molecule (e.g. DNA, RNA, siRNA, antisense oligonucleotide, amplicon) a peptide, a protein, a saccharide, a polysaccharide, a carbohydrate, and the like. The analyte can also refer to different epitopes present on the same protein or polypeptide. The analyte can refer to analytes from pathogenic or non-pathogenic organisms.

The capture reagent can also be, for example, protein A, protein G, and the like.

In some embodiments, the protein is a pathogen protein. A pathogen protein refers to a protein that is from a pathogen. Examples of pathogens include, but are not limited to, viruses, prokaryote and, for example, pathogenic eukaryotic organisms such as unicellular pathogenic organisms and multicellular parasites. Pathogens also can include protozoan pathogens which include a stage in the life cycle where they are intracellular pathogens. As used herein, the term "intracellular pathogen" is meant to refer to a virus or pathogenic organism that, at least part of its reproductive or life cycle, exists within a host cell and therein produces or causes to be produced, pathogen proteins.

Bacterial pathogens include, but are not limited to, such as bacterial pathogenic gram-positive cocci, which include but are not limited to: pneumococcal; staphylococcal; and streptococcal. Pathogenic gram-negative cocci include, but are not limited to: meningococcal; and gonococcal. Pathogenic enteric gram-negative bacilli include, but are not limited to: enterobacteriaceae; *pseudomonas*, acinetobacteria and eikenella; melioidosis; *salmonella*; shigellosis; hemophilus; chancroid; brucellosis; tularemia; *yersinia (pasteurella)*; *streptobacillus moniliformis* and spirilum; *Listeria monocytogenes*; erysipelothrix rhusiopathiae; diphtheria; cholera; anthrax; donovanosis (granuloma inguinale); and bartonellosis. Pathogenic anaerobic bacteria include, but are not limited to: tetanus; botulism; other clostridia; tuberculosis; leprosy; and other mycobacteria. Pathogenic spirochetal diseases include, but are not limited to: syphilis; treponematoses: yaws, pinta and endemic syphilis; and leptospirosis. Other infections caused by higher pathogen bacteria and pathogenic fungi include, but are not limited to: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include, but are not limited to, rickettsial and rickettsioses. Examples of *mycoplasma* and chlamydial infections include, but are not limited to: *Mycoplasma pneumoniae*; lymphogranuloma venereum; psittacosis; and perinatal chlamydial infections. Pathogenic protozoans and helminths and infectious eukaryotes thereby include, but are not limited to: amebiasis; malaria; leishmaniasis; trypanosomiasis; toxoplasmosis; *Pneumocystis carinii*; babesiosis; giardiasis; trichinosis; filariasis; schistosomiasis; nematodes; trematodes or flukes; and cestode (tapeworm) infections. Bacteria also include, but are not limited to, *Listeria, E. coli*, an *Campylobacter*, and a *Salmonella*.

In some embodiments, *E. Coli* is *E. coli* 0157.

Examples of viruses include, but are not limited to, HIV, Hepatitis A, B, and C, FIV, lentiviruses, pestiviruses, West Nile Virus, measles, smallpox, cowpox, ebola, coronavirus, and the like. Other pathogens are also disclosed in U.S. Patent Application Publication No. 20080139494, which are incorporated by reference.

In some embodiments, the pathogen is a food borne pathogen. The analyte can be present on a food borne pathogen. Food borne pathogens are pathogens (e.g. viral or bacterial) that cause illness after eating contaminated food. The food itself does not directly cause the illness, but it is rather the consumption of the food borne pathogen that is present on the food that causes the illness. In some embodiments, the food borne pathogen is *E. coli, Campylobacter*, or *Salmonella*. In some embodiments, the analyte is an analyte chosen from a food borne pathogen analyte. For example, the food borne pathogen analyte can be, but is not limited to, chosen from an *E. coli* analyte, a *Campylobacter* analyte, or a *Salmonella* analyte. In some embodiments, the analyte is the species specific O-Antigen. In some embodiments, the O-antigen is the *E. coli* and/or the *Salmonella* O-antigen and can be used for *E. coli* and *Salmonella* detection. In some embodiments, the analyte is a flagellin antigen. In some embodiments, the analyte is the *Campylobacter* flagellin antigen.

In some embodiments, the capture reagent comprises a detection reagent. The detection reagent can be any reagent that can be used to detect the presence of the capture reagent binding to its specific binding partner. The capture reagent can comprise a detection reagent directly or the capture reagent can comprise a particle that comprises the detection reagent. In some embodiments, the capture reagent and/or particle comprises a color, colloidal gold, radioactive tag, fluorescent tag, or a chemiluminescent substrate. The capture reagent and/or particle comprises a near-infrared or infrared tag or substrate. In some embodiments, the capture reagent and/or particle comprises a color, colloidal gold, radioactive tag, fluorescent tag, or a chemiluminescent substrate. In some embodiments, the capture reagent or particle comprises a nanocrystal, functionalized nanoparticles, up-converting nanoparticles, cadmium selenide/cadmium sulfide fusion nanoparticles, quantum dots, and a Near-Infrared (NIR) fluorophore or material (like but not limited to materials such as lanthanide clusters and phthalocyanines, as well as light emitting-diodes consisting of CuPc, PdPc, & PtPc) capable of emitting light in the NIR spectrum. In some embodiments, the capture reagent and/or particle is conjugated to colloidal gold, silver, radioactive tag, fluorescent tag, or a chemiluminescent substrate, near-infrared compound (e.g. substrate, molecule, particle), or infrared compound (e.g. substrate, molecule, particle). The particle can be, for example, a viral particle, a latex particle, a lipid particle, a fluorescent particle, a near-infrared particle, or infrared particle. As used herein, the term "fluorescent particle" refers to a particle that emits light in the fluorescent spectrum. As used herein, the term "near-infrared particle" refers to a particle that emits light in the near-infrared spectrum. As used herein, the term "infrared particle" refers to a particle that emits light in the infrared spectrum. In some embodiments, the colloidal gold has a diameter size of: about 20 nm, about 30 nm, or about 40 nm or in the range of about 20-30 nm, about 20-40 nm, about 30-40 nm, or about 35-40 nm. In some embodiments, the particle comprises a metal alloy particle. In some embodiments, the metal alloy particle has a diameter from about 10 to about 200 nm. Examples of metal alloy particles include, but are not limited to, gold metal alloy particles, gold-silver bimetallic particles, silver metal alloy particles, copper alloy particles, Cadmium-Selenium particles, palladium alloy particles, platinum alloy particles, and lead nanoparticles.

In some embodiments, the test membrane also comprises one or more capture reagents.

The capture reagents of the present invention can also include an anti-antibody, i.e. an antibody that recognizes another antibody but is not specific to an analyte, such as, but not limited to, anti-IgG, anti-IgM, or ant-IgE antibody. Where the test membrane comprises an anti-antibody, such as anti-IgG, anti-IgM, or anti-IgE antibody, this non-specific antibody can be used as a positive control to detect whether the conjugate has been released from the conjugate pad. When the sample is applied to the device it allows a first capture reagent to be released from the conjugate pad. As the capture reagent is released and flows through the device, either attached to the analyte or not, it can contact the anti-antibody, such as anti-IgG or anti-IgM antibody, which can then be detected. This detection can be used to show that the device is working properly.

In some embodiments, the test membrane comprises a second analyte specific capture reagent. In some embodiments, the test membrane comprises a first area comprising a first capture reagent comprising an anti-IgG capture reagent; and a second area comprising a second analyte specific capture reagent, wherein the first and second areas do not completely overlap or coincide with one another. This non-limiting embodiment can be used to demonstrate the device is working properly and be used to detect the presence of the analyte of interest.

In some embodiments, the conjugate pad comprises a first analyte specific capture reagent and the test membrane comprises a second analyte specific capture reagent, wherein the first and second analyte specific capture reagents bind to non-competitive epitopes present on the analyte. The device can, for example, employ a sandwich type assay that occurs in two steps. The first step is the binding of the analyte to the capture reagent present in the conjugate pad. After binding to the first analyte specific capture reagent the analyte can flow through to or make contact with the test membrane where a second analyte specific capture reagent is present. Upon interaction with the test membrane if the test analyte can bind to the second analyte-specific capture reagent it will be able to be detected either through visualization or through the use of another detection device such as, but not limited to, a fluorescent reader. The test membrane and the conjugate pad can comprise additional analyte-specific capture reagents that recognize different analytes or different epitopes. In some embodiments, the test membrane or the conjugate pad comprises 1, 2, 3, 4, 5, 6, 7, 8, 9, 10 analyte-specific capture reagents. In some embodiments, the test membrane or the conjugate pad comprises a plurality of analyte-specific capture reagents. In some embodiments, each analyte-specific capture reagent recognizes a different analyte or a different epitope on the same analyte.

"Different analytes" can also refer to the same protein or homologous nucleic acid molecule but is a protein or nucleic acid molecule that is from different strains of the same organism. Different analytes can also refer to analytes from different organisms. For example, there are any many strains of *E. coli*. Not all strains of *E. coli* cause a food-borne illness. The present invention can be used, for example, to detect an analyte from a pathogenic *E. coli* strain as opposed to detecting an analyte from a non-pathogenic *E. coli* strain. In some embodiments, the conjugate pad and/or test membrane comprises a first and a second analyte-specific capture reagents, wherein the first and said second capture reagents recognize different analytes. In some embodiments, the test membrane and/or conjugate pad comprises a plurality of areas comprising a plurality of analyte-specific capture reagents, wherein the plurality of analyte-specific capture reagents recognize different analytes. In some embodiments, the plurality of areas do not completely overlap or coincide with one another. In some embodiments, the plurality of analytes are each independently chosen from an *E. coli* analyte, an *Campylobacter* analyte, *Listeria* analyte, and a *Salmonella* analyte. In some embodiments of the present invention, the plurality of analytes is 2, 3, 4, 5, 6, 7, 8, 9, 10, or more than 10 analytes.

The devices may be housed singly, in pairs, or in multiple configurations. The housing can be watertight to prevent leakage and can be manufactured from a variety of inert materials, such as polymer materials. The inlet, in some embodiments, can be of sufficient volume to contain any required amount of sample or reagents to be used with the invention.

Because the membranes, members, or pads of the device are, in some embodiments, chemically inert, they may have to be activated at any reaction site where it is desired to immobilize a specific binding reagent against solvent transport. Various methods may be required to render the reagent immobilized according to the particular chemical nature of the reagent. Generally, when the media is nitrocellulose or a mixed nitrocellulose ester, no special chemical linkage is required for the immobilization of reagents. Various techniques may be used for other materials and reagents which include functionalization with materials such as carbonyldiimidazole, glutaraldehyde or succinic acid, or treatment with materials such as cyanogen bromide. Other suitable reactions include treatment with Schiff bases and borohydride for reduction of aldehyde, carbonyl and amino groups. DNA, RNA and certain analytes may be immobilized against solvent transport by baking onto the chromatographic material. Baking may be carried out at temperatures ranging from about 60° C. to about 120° C. for times varying from about five minutes to about 12 hours, and in some embodiments, at about 80° C. for about two hours.

The present invention also provides systems comprising the devices described herein and a buffer container. The buffer container can be any buffer that the sample that is being tested can be mixed with and then applied to the device. For example, the sample can be taken from a source and the sample can be mixed with the buffer. The buffer can be a lysis buffer that will lyse the cells or a buffer that maintains the pH of the sample so that the analysis can be done properly. The buffer container can be any shape and can be included outside or inside the housing of the device.

In some embodiments, the present invention provides a system that comprises a sample collector. The sample collector can be any material that can take a sample from a source and allow the sample to be tested. For example, the sample collector can be a swab, such as a cotton-swab. In some embodiments, the sample collector is an innoculator. In some embodiments, the housing comprises the sample collector and a portion of the sample collector is in the inside of the housing. In some embodiments, the sample collector is partially outside and partially inside the housing. In some embodiments, the sample collector is completely outside the housing.

The present invention also provides for kits comprising the devices described herein. The kit can include a device as described herein, a sample collector, a buffer container, an instruction manual, a positive control, a negative control, or any combination thereof. With respect to the kit, a positive control is a sample that is known to contain the analyte that can be detected with the device present in the kit. In contrast the negative control, would not contain an analyte that can be detected by the kit. The negative control when used in conjunction with the anti-antibody would be able to demonstrate that the device is working properly.

Buffers can also be included in the present invention. Examples of buffers include, but are not limited to, 1×PBS (10 mM Phosphate, 137 mM Sodium Chloride, 2.7 mM Potassium Chloride), a wash buffer (e.g. 10 mM Sodium Phosphate, 150 mM NaCl, 0.5% Tween-20, 0.05% Sodium Azide), a membrane buffer (e.g. 10 mM Sodium Phosphate, 0.1% Sucrose, 0.1% BSA, 0.2%, PVP-40 pH 7.21, filtered with 0.2 µm filter.), Polyclonal Conjugate Block Buffer (e.g. 50 mM Borate, 10% BSA, pH 8.93); Polyclonal Conjugate Diluent (e.g. 50 mM Borate, 1% BSA, pH 9.09), or Blocking Buffers (e.g. 10 mM Sodium Phosphate, 0.1% Sucrose, 0.025% Silwet pH 7.42; 10 mM Sodium Phosphate, 1% Sucrose, 1% Trehalose, 0.01% BSA, 0.025% Tween-20; 0.05% Sodium Azide, 0.025% Silwet pH 7.4; 10 mM Sodium Phosphate, 0.1% Sucrose, 0.1% BSA, 0.2% PVP-40 pH 7.21). The buffer can also be, but is not limited to, a blocking buffer (e.g. 10% BSA in deionized water, pH 7.4 or 1% BSA in deionized water, pH 7.4); 10 mM Borate, 3% BSA, 1% PVP40, and 0.25% Tween-100; and the like.

The conjugate pad and the test membrane can be contacted with any of the buffers described herein either in the presence or absence of a capture reagent and, in some embodiments, allowed to dry.

Examples of buffers that are lysis buffers include, for example, but are not limited to, 2% Tween (v/v) and 0.1% Triton (v/v); 2% Tween (v/v) and 0.1% SDS (w/v); 2% Tween (v/v) and 0.1% BSA (w/v); 2% Tween (v/v) and 1% BSA (w/v), 0.1% SDS (w/v), 1% BSA (w/v), or any combination thereof. The lysis buffers can also be, for example, 5% Tween/PBS; 2% Tween/PBS+0.1% SDS; 2% Tween/PBS+1% BSA. Other examples of lysis buffers include, but are not limited to, 5% Tween-80 (v/v); 5% Triton X-100 (v/v); 5% NP40 (v/v); 2% Tween-80 (v/v); 2% Triton X-100 (v/v); 2% NP40 (v/v); 1% Tween-80 (v/v); 1% Triton X-100 (v/v); and 1% NP40 (v/v). The detergents and other components of the buffers can be made with any suitable buffer suitable for proteins, and includes, but is not limited to, water and phosphate buffered saline. The lysis buffers can be used to prepare the samples prior to the samples making contact with the devices described herein. In some embodiments, a lysis buffer is not used. A lysis buffer is not used on a sample when a surface protein or surface analyte is desired to be detected. Accordingly, in some embodiments, the sample is not subject to lysis or conditions that would cause a cell to be lysed.

The present invention also provides for methods of detecting an analyte comprising contacting a sample with a device and/or system as described herein, wherein the sample contacts the conjugate pad and the test membrane, wherein a positive reaction with the test membrane indicates the presence of the analyte, wherein the conjugate pad comprises a first analyte-specific capture reagent and the test membrane comprises a second analyte-specific capture reagent. A positive reaction is indicated by the capture reagent present in the test membrane binding to an analyte in the test sample. The capture reagent in the test membrane is applied to the test membrane so that it will indicate a positive reaction when it binds to its specific analyte. The specific capture reagent can be applied in any manner such that when it is detected it can form a line, a circle, a plus sign, a broken line, an "X" or any other pattern. In some embodiments, the control line indicating that the device is working properly will cross the analyte specific line and when the analyte specific capture reagent binds to the analyte the detectable label will form a plus sign. The detection can be determined by the detection of the detection reagent as described herein and by routine methods known to one of skill in the art.

In some embodiments, a sample contacts the device, which is then followed by a buffer being applied to the device after the sample has contacted the device. For example, a sample comprising an antigen can be contacted with the conjugate pad such that the sample is transferred to the conjugate pad. Following the contact with the conjugate pad a separate solution can be applied to the device to facilitate or initiate the vertical flow through the devices described herein.

In some embodiments as described herein the capture reagent is an antibody. In some embodiments, the sample that is tested is a solution but can also be a mixture of solution or buffer and solid material that can be applied to the device. The solution will then solubilize the analyte and allow the conjugate pad's capture reagent to come into contact with the analytes present in the sample. In some embodiments, the sample comprises a cell lysate. In some embodiments, the cell lysate has been clarified by centrifugation or other means to remove non-soluble materials.

In some embodiments, the methods comprise contacting a test sample with a sample collector and contacting the sample collector with the device. In some embodiments, the methods comprise contacting the sample collector with a solution or buffer, wherein the solution or buffer is applied to the device. In some embodiments, the samples are contacted with the conjugate pad prior to the sample coming into contact with the test membrane. In some embodiments, the sample is contacted with the conjugate pad and the test membrane simultaneously.

In some embodiments, the method comprises moving the conjugate pad of the devices described herein, wherein the movement of the devices exposes the test membrane for detection. In some embodiments, the locking member moves the conjugate pad. In some embodiments, the conjugate pad is attached to the locking member and/or the sliding button member. In some embodiments, movement or removal of the removable member moves or removes the conjugate pad. In some embodiments, the conjugate pad is attached to the removable member and/or the adhesive member. In some embodiments, when the removable member is moved or removed the adhesive member is also moved with respect to its original position or removed from the device. The analyte that the method can be used to detect can be any analyte. The analyte can be those that are discussed herein or any other analyte that can be detected using the methods and devices described herein. In some embodiments, the method comprises applying the sample to the device and allowing the sample to flow through the device via vertical flow.

In some embodiments the detection or indication of the presence or absence of an analyte occurs in less than 60 seconds. In some embodiments, the detection or indication of the presence or absence of an analyte occurs in about 30 to about 60 seconds. In some embodiments, the detection or indication of the presence or absence of an analyte occurs in less than 2 minutes. In some embodiments, the detection or indication of the presence or absence of an analyte occurs in about 30 seconds.

In some embodiments, the present invention provides devices for detecting an analyte. In some embodiments, the device comprises a housing. The device can comprise a first housing member and a second housing member to form the housing. The first and second housing members are separate members. The first and second housing members can be manufactured as a single piece. The single piece, in some embodiments, can be separated into the two housing members to allow for the introduction of the materials into the housing (e.g. device). In some embodiments, the device comprises an inlet. The inlet can be in either housing member (e.g. first or second housing member). The inlet can be oriented above the conjugate pad, such that a sample that is introduced into the device through the inlet contacts the conjugate pad prior to contacting the test membrane. The device is oriented such that regardless of any pressure being applied to the device, the sample will flow vertically down through the layers of membranes (e.g. analyte detection membrane system). Accordingly, in some embodiments, the second housing member comprises the inlet opening. In some embodiments, the second housing member is on top of the first housing member. The inlet can be any size or shape as described herein so long as the size and shape is sufficient for the introduction of a sample into the device such that the sample can contact the analyte detection membrane system.

The device can comprise one or more force members. The force members can apply pressure to the analyte detection membrane system. The force is applied perpendicular or substantially perpendicular to the membranes or layers of the analyte detection membrane system. In some embodiments, the device comprises at least 1, 2, 3, 4, or 5 force members. In some embodiments, the device comprises at least 1, 2, 3, 4, or 5 force members. In some embodiments, the device comprises a plurality of force members. The force members can be in contact with a housing member. In some embodiments, a first surface of the force member is in contact with a housing member (e.g. first or second housing member). In some embodiments, a second surface of the force member contacts the analyte detection membrane system. As described herein, the force member can be used to compress the analyte detection membrane system to facilitate the flow of the sample through the analyte detection membrane system. The pressure can facilitate the sample to flow vertically through the analyte detection membrane system. The force members can be oriented in the device independently of one another. The force members can also be manipulated such that each force member applies a pressure to a distinct analyte detection membrane system and that the force applied to each analyte detection membrane system is different or, in some embodiments, the same or substantially the same.

In some embodiments, the device comprises one or more movable locking members. In some embodiments, the movable locking member contacts a force member. In some embodiments, the movable locking member contacts each force member present in the device. For example, in a device comprising a first and second force members, the movable locking member is in contact with the first force member and the second force member. The movable locking member, in some embodiments, supports the force member such that the force member is in a raised position. The raised position can be determined by comparing the force member's position when it is in contact with the movable locking member to when the force member is not in contact with the movable locking member. In the absence of contact between the force member and the movable locking member, the force member is in a first position. When the movable locking member is in contact with the force member, the force member is in a second position. In some embodiments, the second position of the force member is considered to be a raised position. The raised position can be used to compress the layers (e.g. membranes) of the analyte detection membrane system. When the movable locking member is not in contact with the force member, in some embodiments, the analyte detection membrane system is not compressed.

The device can comprise one or more movable locking members. In some embodiments, the device comprises a plurality of, or 1, 2, 3, 4, or 5 movable locking members. In some embodiments, the device comprises at least 1, 2, 3, 4, or 5 movable locking members. In some embodiments, the device comprises a number of movable locking members that is equal to the number of force members present in the device.

The movable locking members can also comprise a moving member, such as, but not limited to, a handle. The moving member can be used, for example, to turn or move the movable locking member such that the locking member contacts the force member. In some embodiments, the moving member disengages the locking members from the force member such that the force member changes positions (e.g. from a raised position to a lower position). The moving member can be used to relieve or apply the pressure being applied on the analyte detection membrane system. The moving member can also be used to relieve or apply compression of the analyte detection membrane system. In some embodiments, the moving member rotates the locking member around a central axis of the device. For example, after applying the sample to the device and the sample flows through at least one analyte detection membrane system, the moving member is moved, which rotates the movable locking member in either a clockwise or counterclockwise direction. The rotation of the movable locking member allows the force member to be lowered into a different position. The rotation of the movable locking member can also allow the pressure that is applied to the analyte detection membrane system to be relieved. In some embodiments, the pressure is completely relieved, or, in some embodiments, the pressure is only partially relieved.

In some embodiments, the moving member that moves the movable locking member protrudes through the first or second housing member. In some embodiments, the moving member is accessible through the moving member outlet. In some embodiments, the moving member rotates around a central axis of the device when moved. In some embodiments, the moving member moves the movable locking member laterally (e.g. horizontally) or vertically. In some embodiments, the movable locking member moves laterally (e.g. horizontally) or vertically when moved.

The moving member and the movable locking member can be constructed as a single piece or as two pieces. In some embodiments, where the movable locking member and the moving member are two separate pieces they are constructed to interact with one another such that the movement of one moves the other. For example, one of the two pieces can have a "male member" that protrudes from the surface and inserts into the "female member" of the other piece to form the interaction.

The movement of the movable locking member by the moving member can also be used to move or remove the conjugate pad present in the analyte detection membrane system. As discussed herein, the conjugate pad is removed to allow visualization or the analysis of the test membrane. The conjugate pad, as discussed herein, can be removed completely from the analyte detection membrane system or an amount that is sufficient to allow visualization or analysis of the test membrane. Analysis of the test membrane can be based solely upon visual inspection, or in some embodiments, an optical reader can be used to analyze the test membrane to determine the absence or presence of an analyte in the sample.

In some embodiments, the device comprises a plurality, or two or more analyte detection membrane systems. In some embodiments, the device comprises at least 1, 2, 3, 4, or 5 analyte detection membrane systems. In some embodiments, the device comprises 1, 2, 3, 4, or 5 analyte detection membrane systems. The analyte detection membrane system can be as described herein and throughout the present application.

In some embodiments, the device comprises one or more flexible or non-flexible attachment members. In some embodiments, the device comprises a plurality of flexible or non-flexible attachment members. In some embodiments, the device comprises at least 1, 2, 3, 4, or 5 flexible or non-flexible attachment members. In some embodiments, the device comprises 1, 2, 3, 4, or 5 flexible or non-flexible attachment members. In some embodiments, the flexible or non-flexible attachment member contact the movable locking member. In some embodiments, the flexible or non-flexible attachment member contact the movable locking member and the conjugate pad. The flexible or non-flexible attachment member can be used to remove or move the conjugate pad away from the rest of the layers (e.g. membranes) of the analyte detection membrane system. In some embodiments, the device comprises a number of flexible or non-flexible attachment members that is equal to the number of analyte detection membrane systems present in the device. In some embodiments, the device comprises a number of flexible attachment members that is equal to the number of force members present in the device. The flexible or non-flexible attachment members can also be used to retract the conjugate pad so as to reveal or expose a portion or all of the test membrane.

For example, in some embodiments, a device comprises three analyte detection membrane systems and three force members. In such a device, for example, the device comprises a first, second, and third flexible attachment member. The first flexible attachment member can be in contact with the conjugate pad of the first analyte detection membrane system and a movable locking member. Additionally, in some embodiments, the second flexible attachment member can be in contact with the conjugate pad of the second analyte detection membrane system and a movable locking member. In some embodiments, the third flexible attachment member can be in contact with the conjugate pad of the third analyte detection membrane system and a movable locking member. In some embodiments, the first, second, and third flexible attachment members are in contact with the same movable locking member. In some embodiments, the first, second, and third flexible attachment members are in contact with different movable locking members. For example, in some embodiments, the first and second flexible attachment members are in contact with the same movable locking member and the third flexible attachment member is in contact with a different movable locking member. Each flexible attachment member is independently contacted with one or more movable locking members.

In some embodiments, the movable locking member comprises one or more movable locking member extensions. In some embodiments, the movable locking member extensions contacts a force member. In some embodiments, the device comprises a number of movable locking member extension that is the same as the number of force members that are present in the device. In some embodiments, the movable locking member extension partially encircles or encompasses the force member. In some embodiments, the movable locking member extension completely encircles or encompasses the force member. The shape of the movable locking member or member extension can be any shape to keep the force member in a raised position. In some embodiments, the extension is a hook or hook-like shape that partially or completely encircles or encompasses the force member. The shape is not essential so long as the shape acts as a support for the force actuator (e.g. force member).

The number of movable locking member extensions can the same or different as the number of force members present in a device described herein. In some embodiments, a device comprises a plurality of movable locking member extensions. In some embodiments, a device comprises at least 1, 2, 3, 4 or 5 movable locking member extensions. In some embodiments, a device comprises 1, 2, 3, 4 or 5 movable locking member extensions. For example, in some embodiments, a device comprises a first, second, and third force members attachment members and a first, second, and third movable locking member extensions. In this non-limiting example, for example, the first force member contacts the first movable locking member extension, the second force member contacts the second movable locking member extension, and the third force member contacts the third movable locking member extension.

In some embodiments, the movable locking member comprises a flexible attachment member extension. In some embodiments, the flexible attachment member extension contacts the flexible attachment member. In some embodiments, the flexible attachment member extension comprises a flexible attachment member extension nodule. The nodule can be any shape or size that allows the flexible attachment member to be secured to so that the flexible attachment member securely maintains its contact with the movable locking member. In some embodiments, the one or more movable locking member extensions extend radially (e.g. outward) from the center of the movable locking member.

The number of flexible attachment member extension can the same or different as the number of analyte detection membrane systems present in a device described herein. In some embodiments, a device comprises a plurality of flexible or non-flexible attachment member extensions. In some embodiments, a device comprises at least 1, 2, 3, 4 or 5 flexible or non-flexible attachment member extensions. In some embodiments, a device comprises 1, 2, 3, 4 or 5 flexible or non-flexible attachment member extensions. For example, in some embodiments, a device comprises a first, second, and third flexible attachment members and a first, second, and third flexible attachment member extensions. In this non-limiting example, for example, the first flexible attachment member contacts the first flexible attachment member extension, the second flexible attachment member contacts the second flexible attachment member extension, and the third flexible attachment member contacts the third flexible attachment member extension.

In some embodiments, the devices described herein comprise flexible and non-flexible attachment members and/or member extensions.

In some embodiments, the device comprises a channel system. The channel system can be used to transport the sample (e.g. fluid) from the inlet opening of the device to the analyte detection membrane system(s) present in the device. As used herein, the "channel system" refers to the entire system regardless of how many individual channels are a part of the system. For example, the channel system can comprises two or more channels, such as, but not limited to, capillaries, that transport fluid from the inlet to an analyte detection membrane system. In some embodiments, the channel system comprises one or more branches (e.g. arms). The one or more branches can be transport fluid to one or more analyte detection membrane systems. In some embodiments, the channel system comprises 1, 2, 3, 4, or 5 branches. In some embodiments, the device comprises a number of branches in the channel system that is equal to the number of analyte detection membrane systems present in the device.

In some embodiments, each branch of the channel system comprises capillary tubes that transport the fluid from the inlet to the analyte detection membrane system. In some embodiments, each branch comprises a plurality of capillary tubes. In some embodiments, each branch comprises at least 1, 2, 3, 4, or 5 capillary tubes. In some embodiments, the channel system does not comprise capillary tubes or tube-like formations but is made from a material that allows a portion of the sample to be transported from the inlet to the conjugate pad of the analyte detection system. In some embodiments, the channel system is a porous material that can be used to transport the sample from the inlet to the analyte detection membrane system. In some embodiments, the channel system is made from the same material as the conjugate pad. In some embodiments, the channel system and the conjugate pad are a contiguous piece of material. In some embodiments, the channel system comprises a Porex material. These porous materials allow the inlet to be in fluid communication with the analyte detection membrane system. In some embodiments, the porous material comprises polyethylene, polypropylene, polytetrafluourouethylene (PTFE), PVDF, ethyl vinyl acetate, Nylon 6, thermoplastic polyurethane (TPU), SCP, and the like. In some embodiments, the conjugate pad and the channel system are the same materials or different materials. In some embodiments, the channel system does not comprise a porous material and/or a capillary tube system.

In some embodiments, the channel system contacts the inlet. In some embodiments, the channel system contacts the top of the analyte detection membrane system. In some embodiments, the channel system contacts the top of the conjugate pad or a membrane that is on top of the conjugate pad. In some embodiments, the channel system contacts an edge of the conjugate pad or an edge of a membrane that is on top of the conjugate pad. Regardless of how the sample contacts the analyte detection membrane system, in some embodiments, the sample flows vertically through analyte detection membrane system. Therefore, although the sample may flow horizontally (e.g. laterally) from the inlet to the analyte detection membrane system, the sample is not analyzed until it flows vertically through the analyte detection membrane system. This is distinctly different from lateral flow systems where a sample flows laterally (e.g. horizontally) through multiple membranes or test layers.

In some embodiments, the channel system divides the sample into equal portions, wherein each equal portion contacts an independent analyte detection membrane system. In some embodiments, the channel system divides the sample into one or more unequal portions. The one or more unequal portions are then transported to independent analyte detection membrane systems.

For example, in a device that comprises a first and second analyte detection membrane systems the device comprises a channel system that comprises a first and second branch. In some embodiments, the first branch contacts the first analyte detection membrane system and the second branch contacts the second analyte detection membrane system. Upon application of the sample to the device (e.g. through the inlet opening), the sample is transported in equal portions through the first and second branches of the channel system to the first and second analyte detection membrane systems. In some embodiments, the sample is transported in unequal portions through the first and second branches of the channel system to the first and second analyte detection membrane systems. The sample can be divided into unequal portions, for example, based upon the number of capillaries present in each branch. For example, the first branch can comprise more capillaries than the second branch. The greater number of capillaries will allow more of the sample to be transported through the first branch than the second branch, thereby delivering unequal portions to the first and second analyte detection membrane systems.

Accordingly, the branches of the channel system may have the same number of capillaries or different numbers of capillaries. The numbers of capillaries in each branch of the channel system is independent of each branch. That is each branch of the channel system can have the same number or a different number of capillaries as another branch. Therefore, in some embodiments, the device's channel system can be described as a capillary channel system. In some embodiments, the channel system is enclosed in a channel housing that is separate and distinct from the first and second housing members described herein for the device itself. In some embodiments, the channel housing is transparent, translucent, opaque, or partially translucent.

As discussed herein, the test membrane can be analyzed either visually with the human eye or through a machine, such as an optical reader. In some embodiments, the analysis is done through a portal. In some embodiments, the device comprises one or more portals that are sufficient in size to allow visualization of a test membrane of one or more of the analyte detection membrane systems. In some embodiments, a single portal is used to visualize each of the test membranes present in the device. In some embodiments, the device does not comprise a portal. In embodiments, where the device does not comprise a portal, the test membrane can still be visualized by using a transparent or translucent housing for the device. In some embodiments, the first and/or second housing are transparent or translucent. Where the first and/or second housings are transparent or translucent this can allow an analyte detection membrane systems and its test membrane when it is revealed upon moving or removing the conjugate pad. In some embodiments, the device comprises a plurality of portals. In some embodiments, the device comprises at least 1, 2, 3, 4, or 5 portals. In some embodiments, the device comprises 1, 2, 3, 4, or 5 portals. In some embodiments, a device comprises 1 portal that is continuous and exposes each analyte detection membrane system present in the device to visual inspection.

As discussed herein, the force members can be allowed to move between at least two positions (e.g. raised or lowered; engaged or disengaged). In some embodiments, the force member is lowered and is encompassed by a force actuator outlet. Thus, in some embodiments, the device comprises one or more force actuator outlets that that can accept the force member as it is lowered. In some embodiments, the device comprises a plurality of force actuator outlets. In some embodiments, the force actuator outlet is a groove. In some embodiments, the force actuator outlet is a circle or substantially circular. The force actuator outlet can be used to suspend the force actuator (e.g. force member) at a particular position. The force actuator outlet can also be used to retain the force actuator in a second position. In some embodiments, the circumference of the force actuator outlet is greater than the circumference of the portion of the force member that is entering the outlet. In some embodiments, the circumference of the force actuator outlet is greater than the largest circumference of the force member. In some embodiments, the circumference of the force actuator outlet is not greater than the largest circumference of the force member, wherein the force member has areas with at least two different circumferences. For example, force members are described herein that would have two different circumferences. A force member can comprise a cap with one circumference and a support structure that supports the cap with a different circumference. The support structure can, in some embodiments, have a smaller circumference than the cap. In some embodiments, the force actuator outlet can have a circumference that is larger than the support structure circumference, but smaller than the cap structure circumference. In some embodiments, the number of force actuator outlets is the same or different than the number of the force members present in a device.

The force actuator outlet can also be a continuous depression in a housing member that can accept each and every force member in the device when it is lowered and no longer compressing the analyte detection membrane system. The outlet can be used to temporarily house the force member or it can be permanent, such that the force member cannot be raised again to compress or further compress the analyte detection membrane system.

As discussed herein and throughout, the conjugate pad, permeable membrane, test membrane, and absorbent member can be or are compressed by the force member under certain forces as described herein and including, but not limited to a force from about 1 lbf to about 1000 lbf. In some embodiments, where there are multiple analyte detection membrane systems, the pressure applied to each membrane detection system can be different or it can be the same. For example, in a device that has a first, second, and third analyte detection membrane system, the first analyte detection membrane system can be compressed under a force of 5 lbf, the second analyte detection membrane system can be compressed under a force of 10 lbf, and the third analyte detection membrane system can be compressed under a force of 25 lbf. In another example, in some embodiments, the first and second analyte detection membrane systems are compressed under the same pressure and the third analyte detection membrane system is compressed under a pressure that is different from the first and second analyte detection membrane systems. The differences in pressure can be used to use different flow rates, which can be useful for different analytes. The pressure is correlated with the flow rate. The pressure can be manipulated by the position of the force member and how much the layers of the analyte detection membrane system are compressed. The specific force used can be determined and measured by one of skill in the art using known and routine methods.

As described herein, in some embodiments, the present invention provides a system comprises any device described herein, a buffer container or a sample collector. In some embodiments, the present invention provides a kit comprising any device described herein and one or more of a positive control, a negative control, an instruction booklet, a buffer container, and a sample collector, or any combination thereof.

The methods described herein can be used with a device that has, for example, a plurality, two or more, analyte detection membrane systems. The methods can be also be used with devices that have 2, 3, 4, or 5 analyte detection membrane systems. Where there are more than two analyte detection membrane systems (e.g. 3, 4, 5, 6, 7, 8, 9, or 10)

the methods and the descriptions contained herein are modified to be consistent with the number of analyte detection membrane systems. These changes are made in accordance with the descriptions contained herein and any routine changes that would be known by one of skill in the art. The changes to encompass more than 2 analyte membrane detections systems based upon the descriptions contained herein combined with knowledge of one of skill in the art would not require undue experimentation. In some embodiments, the present invention provides methods of detecting an analyte. In some embodiments as described herein, the device comprises two or more analyte detection membrane systems. In some embodiments, the method comprises contacting a sample with the device and a portion of the sample being transported through a channel system to the conjugate pads of the two or more analyte detection membrane systems. In some embodiments, the method comprises detecting a positive or negative reaction for the analyte, wherein a positive reaction indicates that the presence of the analyte. In some embodiments, the two or more analyte detection membrane systems are compressed by the force member. In some embodiments, the sample vertically flows from the conjugate pad to the test membrane. In some embodiments, the method further comprises compressing the analyte detection membrane system by the force member. In some embodiments, the method comprises moving the conjugate pad of the two or more detection systems after a portion of the sample has contacted and flowed through the conjugate pad, thereby exposing the test membrane for analysis. In some embodiments, the test membrane is exposed within the portal opening for detection. In some embodiments, the conjugate pad of the two or more detection systems is moved by moving the movable locking member. In some embodiments, the moving the movable locking member comprises rotating the movable locking member around the central axis of the device. In some embodiments, the movable locking member is moved laterally or vertically. In some embodiments, the moving lockable member moves the conjugate pad of the two or more detection systems simultaneously or sequentially. In some embodiments, the method further comprises relieving the compression of the two or more analyte detection systems. The pressure can be relieved or lessened, for example, by moving the movable locking member. In some embodiments, the movable locking member is moved (e.g. rotated) by turning or moving the moving member that is connected to the movable locking member.

In some embodiments, one or more of the analyte detection membrane systems are compressed prior to the sample contacting the channel system. In some embodiments, one or more of the analyte detection membrane systems are compressed prior to the sample coming into contact with the conjugate pad of the one or more of the analyte detection membrane systems. In some embodiments, each of the analyte detection membrane systems is compressed simultaneously. In some embodiments, each of the analyte detection membrane systems is compressed independently. In some embodiments, each of the analyte detection membrane systems present in a device is compressed prior to a sample coming into contact with the conjugate pad.

In some embodiments, the method comprises relieving the pressure applied by a force member on the two or more analyte detection membrane systems, wherein said force member moves vertically or horizontally to relieve said pressure. In some embodiments, the method comprises the force member moving from a first position to a second position to relieve the pressure. In some embodiments, the force member moves into or comes into contact with a force actuator outlet when the movement of the force member relieves or reduces the pressure or relieves or reduces the force being applied to the analyte detection membrane system. In some embodiments, the force member drops partially or completely out of the device.

In some embodiments, the present invention provides a device for detecting an analyte comprising a pressure actuator, a pressure release, an analyte detection membrane system, an analyte detection membrane system receptacle, and an outlet. In some embodiments, the analyte detection membrane system receptacle is of sufficient size and shape to accept the analyte detection membrane system. In some embodiments, the receptacle is a groove. In some embodiments, the receptacle is a case that can be, but not necessarily, removed from the device.

In some embodiments, the analyte detection membrane system, as described herein, can be encompassed or contained within a cartridge or housing. The housing can comprise a first and/or second housing member. In some embodiments, where the analyte detection membrane system is contained within a housing or a cartridge, the receptacle is of sufficient size and shape to accept the housing or the cartridge. In some embodiments, the housing or cartridge comprises an inlet. The inlet can be used to apply the sample to the analyte detection membrane system. In some embodiments, the cartridge or housing comprises a second outlet that allows the sample to flow through and out of the housing and cartridge. The analyte detection membrane system can be any analyte detection membrane system as described herein.

In some embodiments, the device comprises a pressure actuator. The pressure actuator, for example, can be the force member that is described in herein. In some embodiments, the pressure actuator is an air valve or vacuum valve that either applies air pressure to the analyte detection membrane system or draws a vacuum through the analyte detection membrane system. In some embodiments, the pressure actuator can be regulated by a pressure release or pressure regulator. The pressure release or pressure regulator can be, for example, a vacuum release. The release or regulator can be used to regulate the pressure or vacuum being applied to the analyte detection membrane system. The pressure or vacuum can be applied to the analyte detection membrane system through an outlet or tube that is present in the device. The outlet can be the same outlet present in the cartridge or housing described herein or it can be a different outlet or tube. The outlet or tube can be used so that the pressure or vacuum to be applied with specificity rather than allowing it to diffuse across the entire device.

In some embodiments, the housing (e.g. cartridge) encasing the analyte membrane detection comprises an upper housing and a lower housing. In some embodiments, the housing comprises a plurality of membrane or pad holders. In some embodiments, the housing comprises one or more membrane or pad holders. In some embodiments, the housing comprises 1, 2, 3, 4, or 5 membrane or pad holders. In some embodiments, the housing comprises at least 1, 2, 3, 4, or 5 membrane or pad holders. In some embodiments, the housing comprises an inlet. In some embodiments, the housing comprises an outlet. In some embodiments, the vacuum actuator directly or indirectly contacts the housing outlet.

In some embodiments, the device and any device described herein comprises an ejector for ejection the housing. The ejector can be used to facilitate the removal of the housing that contains the analyte detection membrane system. In some embodiments, the devices comprise a housing separator. The housing separator can be used to facilitate the separation of the housing. In some embodiments, the ejector can also act as the housing separator.

In addition to the methods described herein, in some embodiments, a method of detecting an analyte comprises applying a sample to a device comprising a pressure actuator, a pressure regulator, an analyte detection membrane system, an analyte detection membrane system receptacle, and an outlet or any other device or analyte detection membrane system described herein. In some embodiments, the sample is contacted with the analyte detection membrane system, wherein the sample vertically flows through the analyte detection membrane system. In some embodiments, the method comprises detecting the presence or absence of the analyte.

In some embodiments, detecting comprises removing or moving the conjugate pad present in the analyte detection membrane system a sufficient amount to visualize the result, wherein a positive result indicates the presence of said analyte. In some embodiments, detection comprises removing the analyte detection membrane system from the device and further removing or moving the conjugate pad a sufficient amount to visualize the detection of the analyte. In some embodiments, the analyte detection membrane system is contained within a housing or cartridge, and therefore, in some embodiments, the housing or cartridge is removed from the device prior to the movement or removal of the conjugate pad. In some embodiments, the housing is separated into a first (e.g. upper) and a second (e.g. lower) housing prior to the removal or movement of the conjugate pad as described herein. In some embodiments, the separation of the housing into a first and a second housing removes or moves the conjugate pad to visualize the test membrane as described herein. In some embodiments, the housing is separated manually and/or mechanically. In some embodiments, the housing (e.g. cartridge) is ejected from the device. In some embodiments, the housing is ejected from the device by an ejector. In some embodiments, the housing is separated by a separator. In some embodiments, the ejector also functions as a separator.

In some embodiments, the method comprises applying pressure on or drawing a vacuum through an analyte detection membrane system. In some embodiments, the method comprises releasing or reducing the pressure or the vacuum. In some embodiments, the pressure or vacuum is released or reduced by using the pressure regulator. In some embodiments of the methods described herein, the sample that is contacted with the analyte detection membrane system flows through the analyte membrane system at a flow rate that is regulated by a pressure actuator. In some embodiments, the entire sample flows through the analyte detection membrane system at a constant rate. In some embodiments, the sample flows through the analyte detection membrane system at a variable rate. In some embodiments, the variable rate comprises at least one period of time where the flow rate of a portion of the sample is 0. For example, the pressure being applied or vacuum being drawn can be regulated such that the sample stops flowing through the analyte detection membrane system for a period of time. This can be referred to as a "dwell." As described elsewhere in the present document, the dwell can be implemented by placing impermeable or slightly impermeable membranes between the conjugate pad and the other layers of the analyte detection membrane system. The dwell, however, can also be regulated by regulating (e.g. changing) the pressure that is applied to the analyte detection membrane system. The dwell can also be regulated by regulating (e.g. changing) the vacuum that is being drawn through the analyte detection membrane system. Any method of regulating the flow rate through the analyte detection membrane system, including but not limited to, the flow rate through the conjugate pad and/or the test membrane can be used.

The devices herein, can also be automated or used in conjunction with an optical reader or other type of spectrometer. The advantages of combining the systems and devices described herein with an optical reader or other type of spectrometer is that the sensitivity of the devices and assays can be increased such that less analyte present in the sample is necessary to identify a sample as being positive for that analyte. This greater sensitivity can be then be used, for example, to determine if food contains pathogens, a person has a certain disease or condition, or if a product has an analyte that is otherwise undetectable using other devices and methods in the same amount of time it takes to use the presently described methods and devices.

Accordingly, in some embodiments, the present invention provides a device for detecting an analyte comprising a sample inlet, an analyte detection cartridge receptacle, an analyte detection cartridge receptacle inlet, an optional conjugate pad remover, a pressure actuator, a spectrometer (e.g. optical reader), a display unit, a signal processing unit. The pressure actuator can be a force member whose position is modified to regulate the pressure being applied to the analyte detection membrane system that is used in conjunction with a device. The pressure actuator can also regulate the pressure by drawing a vacuum through the analyte detection membrane system that is used in conjunction with a device. The spectrometer can be any spectrometer that can detect the presence of a signal. The signal can be an optical signal. The signal can be a signal that is emitted in a spectrum chosen from, for example, infrared spectrum; near-infrared spectrum; visible spectrum, x-ray spectrum, ultra-violet spectrum, gamma rays, electromagnetic spectrum, and the like.

The spectrometer can be connected to the signal processing unit (e.g. computer). The signal processing unit can take the signal that is transmitted to it and analyze the signal to determine the presence or absence of the sample. An example of a signal processing unit is, but not limited to, a computer. The signal processing unit can programmed to analyze the signal transmitted by the spectrometer. The programming can implement an algorithm to analyze the signal to determine the presence or absence of an analyte in the sample. The algorithm can be based upon criteria that are pre-installed in the signal processing unit's memory or that are entered by the user of the device. The types of information that can be entered can be cut-offs for a positive or negative signal, processing times, and the like. The signal processing unit can also be used to regulate the pressure applied to or the vacuum drawn through the analyte detection membrane system.

The signal processing unit can be used or programmed to regulate the flow rate of the sample through the analyte detection membrane system. The flow rate can be regulated by regulating the pressure that is applied to or a vacuum that is drawn through the analyte detection membrane system. As described above with respect to the methods described herein, the sample that is contacted with the analyte detection membrane system flows through the analyte membrane system at a flow rate that is regulated by a pressure actuator. The pressure regulator can be in turn regulated by, for example, the signal processing unit. In some embodiments, the entire sample flows through the analyte detection membrane system at a constant rate, which is regulated by the signal processing unit. In some embodiments, the sample flows through the analyte detection membrane system at a variable rate, which is regulated by the signal processing unit. In some embodiments, the variable rate comprises at least one period of time where the flow rate of a portion of the sample is 0, which can be regulated by the signal processing unit. For example, the pressure being applied or vacuum being drawn can be regulated by the signal processing unit such that the sample stops flowing through the analyte detection membrane system for a period of time. As discussed herein, this can be referred to as a "dwell." The dwell, for example, can be regulated by regulating (e.g. changing) the pressure that is applied to the analyte detection membrane system, which can be implemented or controlled by the signal processing unit. The dwell can also be regulated by regulating (e.g. changing) the vacuum that is being drawn through the analyte detection membrane system, which can be implemented or controlled by the signal processing unit. Any method of regulating the flow rate through the analyte detection membrane system, including but not limited to, the flow rate through the conjugate pad and/or the test membrane can be used and such method can be regulated or implemented by the signal processing unit.

In some embodiments, the devices described herein and throughout, comprises an analyte detection cartridge receptacle positioning member. The detection cartridge receptacle positioning member can be used, for example, to place the analyte detection membrane system in the proper position to accept the sample and/or for the sample to be analyzed. In some embodiments, the system is positioned for spectrometer analysis. The detection cartridge receptacle positioning member can be, in some embodiments, motorized and/or controlled by the signal processing unit. In some embodiments, the detection cartridge receptacle positioning member is not motorized but can controlled by a manual controller, such as, but not limited to a lever or screw that allows that receptacle's position to be modified. In some embodiments, the signal processing unit controls the movement of the analyte membrane detection receptacle by moving the analyte membrane detection receptacle moving member. In some embodiments, the analyte detection cartridge receptacle positioning member is in contact with analyte detection cartridge receptacle.

In some embodiments, the devices described herein can comprise a waste receptacle. The waste receptacle can be in the interior of the device or outside but still contacting the device. The waste receptacle can accept analyte detection membrane systems that have been used. In some embodiments, as described herein, the analyte detection membrane system is contained in a housing (e.g. cartridge). The housing can then be ejected into the waste receptacle. The ejection can be manual or automated. In some embodiments, the ejection is controlled by a signal processing unit. In some embodiments, the signal processing unit controls an ejector that ejects the analyte detection membrane system from the analyte detection membrane system receptacle into the waste receptacle. Like all of the devices described herein, in some embodiments, the device comprises an analyte detection membrane system, which can or cannot be encased in a housing (e.g. cartridge).

In some embodiments of the present devices described herein, the pressure actuator contacts the analyte detection membrane system. In some embodiments, the pressure actuator is attached to the device at a point that allows movement of the pressure actuator. In some embodiments, the pressure actuator is attached at a pivot point that allows the pressure actuator to pivot at a single contact point.

In some embodiments, the devices described herein comprise a display. In some embodiments, the display is an electronic display. In some embodiments, the signal processing unit receives an input from the spectrometer and displays information on the display unit. The display unit can be display various information, including but not limited to, the presence and/or absence of one or more analytes, status, and the like.

In some embodiments, the present invention comprises detecting an analyte using a device comprising a signal processing unit or a device described herein. In some embodiments, the method comprises contacting the device with a sample that contacts the analyte detection membrane system within the device. The sample then flows through the analyte detection membrane system. In some embodiments, the method comprises detecting the presence or absence of the analyte. In some embodiments, the detecting comprises the optical reader detecting an optical signal from the analyte membrane system, the optical reader communicating the optical signal to the signal processing unit, the signal processing unit analyzing the optical signal to determine the presence or absence of the analyte; and the signal processing unit displaying a result on the display unit. The displayed result can be visual and/or audible. The signal analyzed can be a signal in a spectrum chosen from infrared spectrum; near infrared spectrum; visible spectrum, x-ray spectrum, ultra-violet spectrum, gamma rays, or electromagnetic spectrum. In some embodiments, the signal is in the near-infrared spectrum. In some embodiments, the method comprises ejecting the analyte detection membrane system into a waste receptacle. In some embodiments, the signal processing unit is a computer.

Referring to the drawings, in some embodiments, FIGS. 1 through 36 depict embodiments of devices, components of such representative devices, and various views of such embodied devices that can be used in the methods and/or in conjunction with or without other devices and/or systems described herein.

FIG. 1 depicts a device comprising a first housing member (10), a buffer container (15), a second housing member (20), a groove for the sliding button (25), a sliding button (30), an inlet opening (35), a collar (40), and a test membrane (45). FIG. 1 depicts a test membrane (45) comprising two capture reagents. The first (10) and second (20) housing members can also be referred to as the lower and upper housing members, respectively. In FIG. 1, the sample would be applied through the inlet opening (35) and can be allowed to vertically flow through to the test membrane (45). In FIG. 1, the groove (25) allows the sliding button to move, which when attached to the locking member moves the locking member and can, in some embodiments, move the conjugate pad and change the position of the force member.

Figure 2:
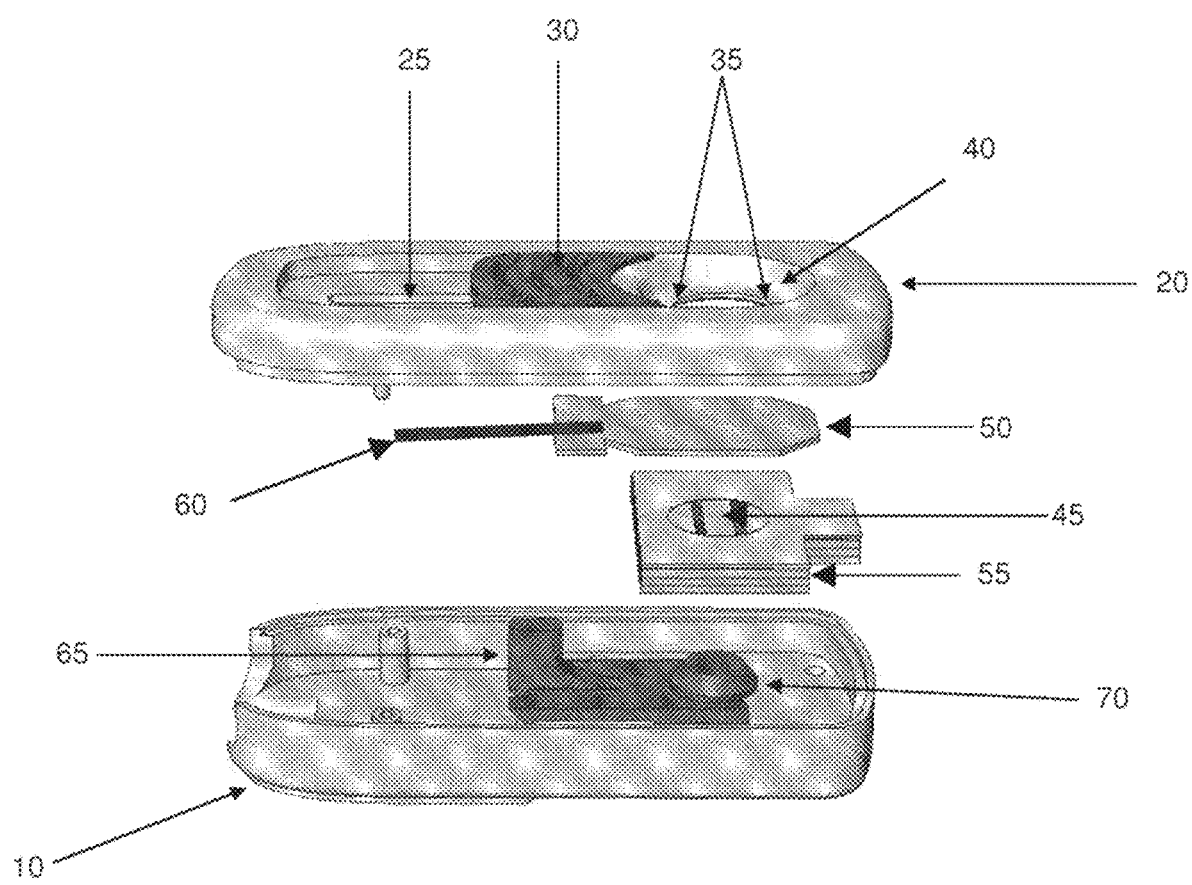
FIG. 2: Depicts some components of a representative device according to some embodiments of the present invention.

FIG. 2 depicts a device comprising a first housing member (10), a second housing member (20), a groove for the sliding button (25), a sliding button (30), an inlet opening (35), a collar (40), a test membrane (45), a conjugate pad (50), a plurality of absorbent members (e.g. pads) (55), an attachment member (60), a locking member (65), and a force member (70). FIG. 2 depicts the conjugate pad (50), test membrane (45) and absorbent pad (55) arranged substantially parallel to one another. The force member (70) when in contact with the absorbent member would be applying pressure that is substantially perpendicular to the conjugate pad. As can be seen in FIG. 2, a sample that is contacted with the device through the inlet opening (35) would flow vertically through the conjugate pad (50) to the test membrane (45). Not explicitly shown in FIG. 2, but in some embodiments, a the permeable membrane is also substantially parallel to the conjugate pad (50) and to the test membrane (45), with a first surface of the permeable membrane contacting a surface of the conjugate pad (50) a second surface of the permeable membrane contacting a surface of the test membrane (45).

Figure 3:
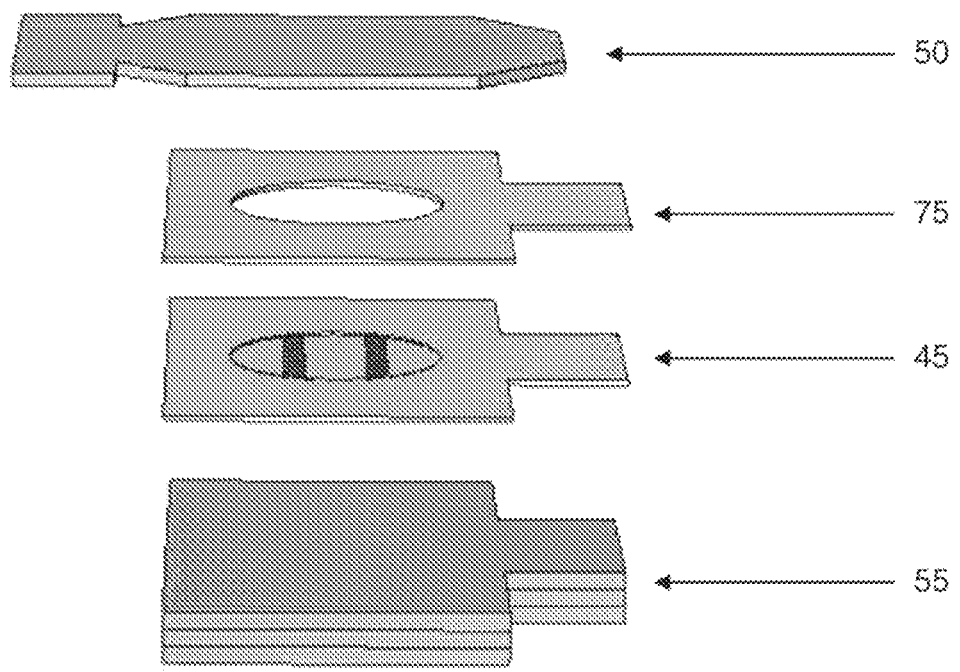
FIG. 3: Depicts some components of a representative device according to some embodiments of the present invention.

FIG. 3 depicts a conjugate pad (50), a permeable membrane (75), a test membrane (45), and a plurality of absorbent members that maybe separated by spacers (55). FIG. 3 depicts the components being substantially parallel with one another. FIG. 3 depicts the permeable membrane (75) comprising an opening. This opening can be used to allow visualization and detection of the test membrane's results.

Figure 4:
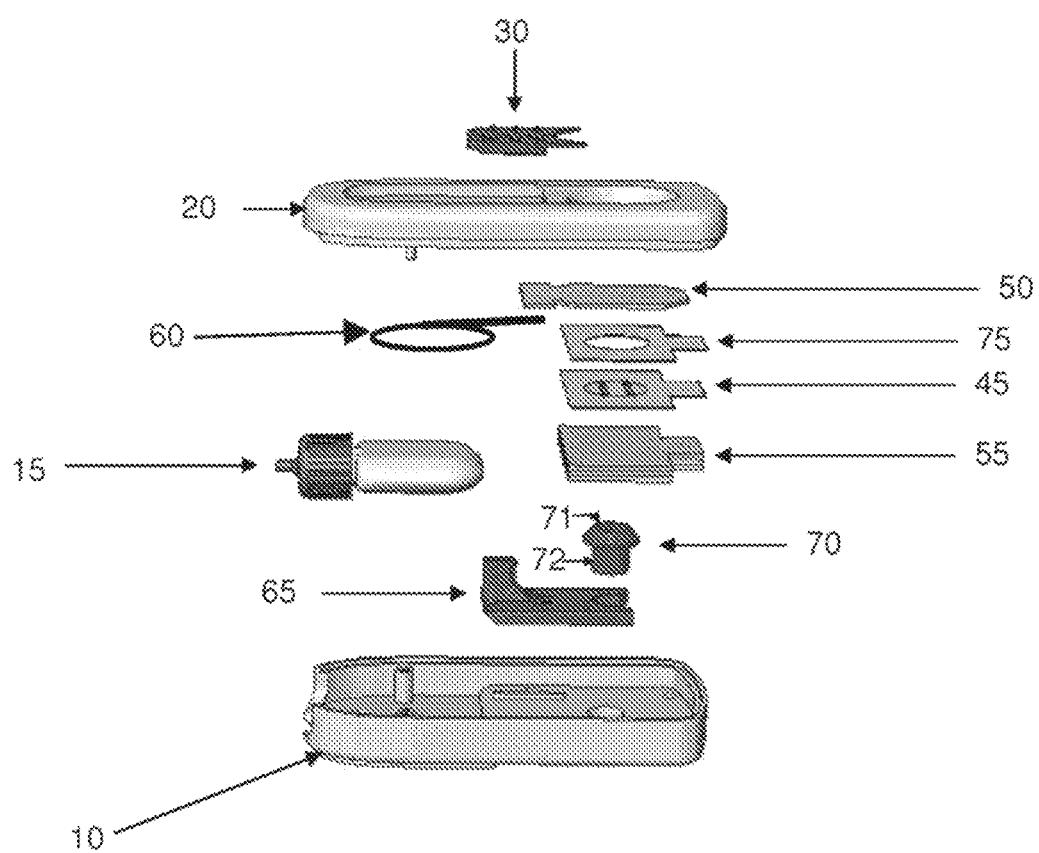
FIG. 4: Depicts some components of a representative device according to some embodiments of the present invention.

FIG. 4 depicts a device comprising a first housing member (10), a buffer container (15), a second housing member (20), a sliding button (30), a test membrane (45), a conjugate pad (50), a permeable membrane (75), a plurality of absorbent members that may be separated by spacers (e.g. pads) (55), an attachment member (60), a locking member (65), and a force member (70). FIG. 4 also depicts the force member (70) comprising a shaft (72) and a head (71) where the head (71) is wider than the shaft (72).

FIG. 5 depicts a partial view of a device comprising a first housing member (10), a locking member (65), a sliding button (30), and force member (70). FIG. 5 depicts the locking member (65) in contact with the force member (70) such that the force member (70) is in a raised method. FIG. 5 also depicts the movement of the locking member (65) and the sliding button (30) away from the force member (70) allowing the force member to change positions. In some embodiments, the change in position is that the force member is lowered.

Figure 6:
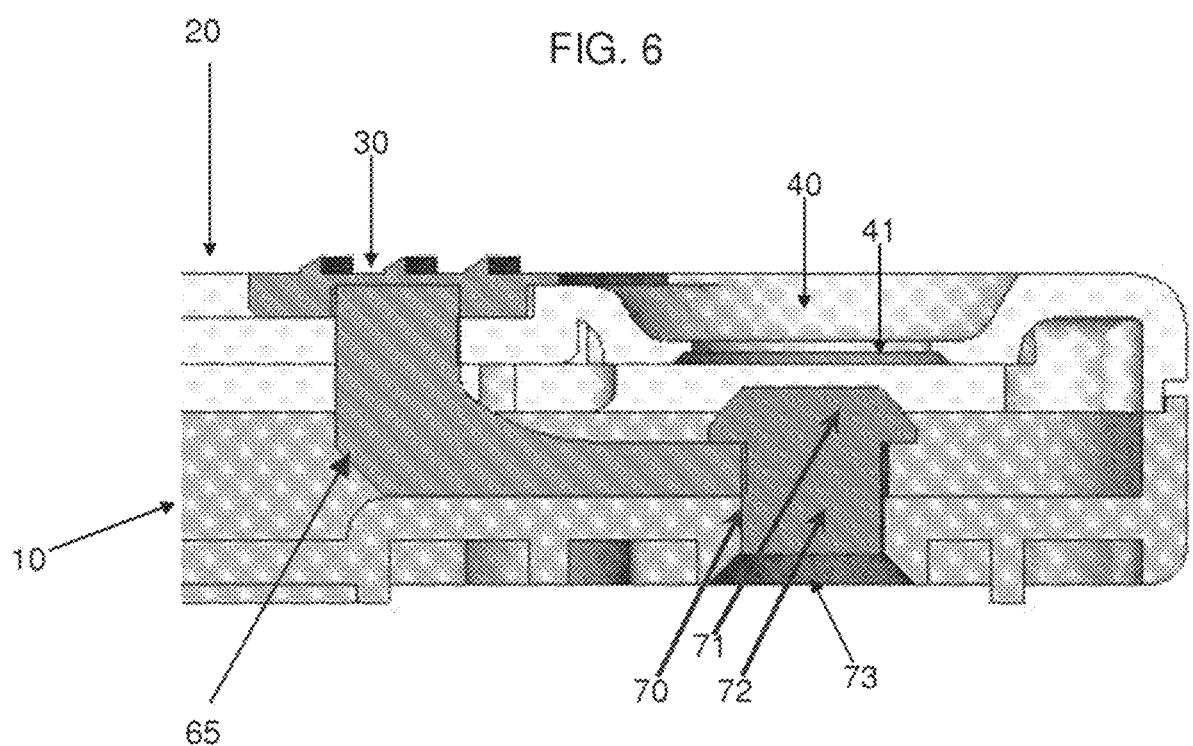
FIG. 6: Depicts a lateral view of some components of a representative device according to some embodiments of the present invention.

FIG. 6 depicts a side cut away view of a device comprising a first housing member (10), a second housing member (20), a sliding button (30), a locking member (65), a collar (40), an O-ring (41), a force member (70), and a support for the force member (73). The support for the shaft can be, for example, part of the first housing member (10) and is shaded differently for example purposes only. FIG. 6 depicts the button (30) in contact with the locking member (65) in such a way that movement of the button (30) will move the locking member (65). Movement of the locking member (65) will take away the support from the force member (70), which would allow the force member (70) to change positions. FIG. 6 also depicts the shaft (72) and the head (71) of the force member. The head (71) creates a lip where the locking member (65) can slide under and support the force member (70).

Figure 7:
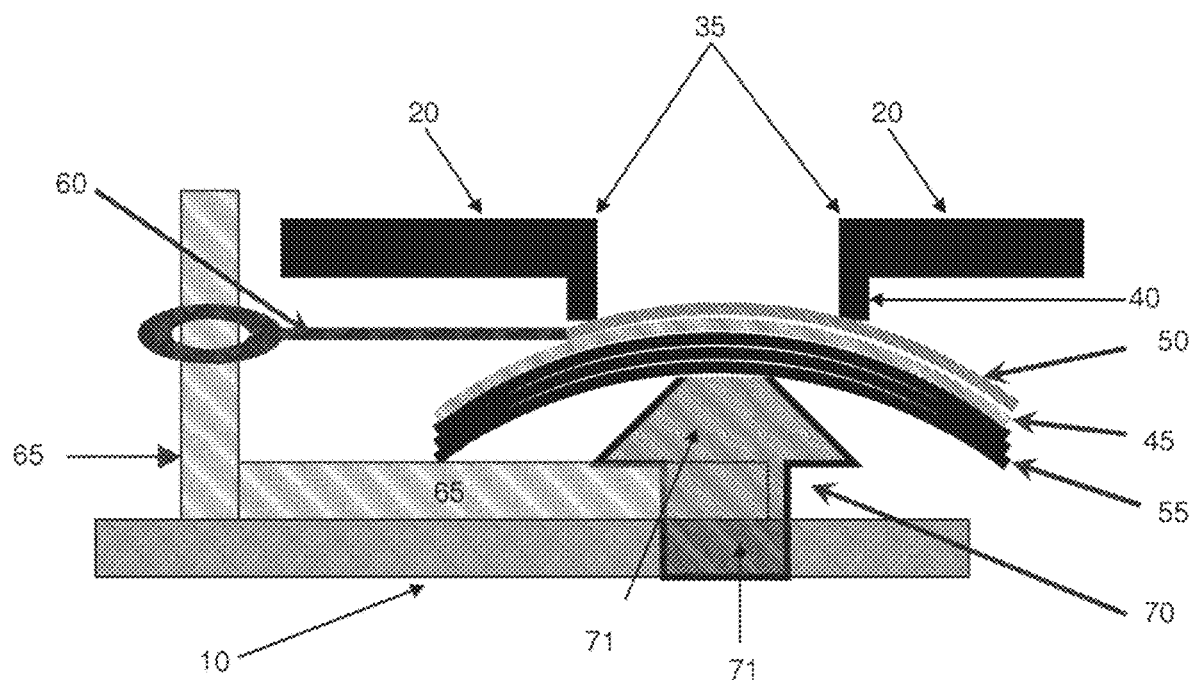
FIG. 7: Depicts a lateral view of some components of a representative device according to some embodiments of the present invention.

FIG. 7 depicts a partial view of a device comprising a first housing member (10), a second housing member (20), an inlet opening (35), a test membrane (45), a conjugate pad (50), a plurality of absorbent members that may be separated by spacers (55), an attachment member (60), a locking member (65), and a force member (70). FIG. 8 depicts the attachment member (60) attached to the conjugate pad (50) and the locking member (65). FIG. 8 also depicts the conjugate pad being compressed against the second housing member (20) and the perimeter of the inlet opening (35). FIG. 7 depicts the head of the force member (71) applying the pressure by contacting the plurality of absorbent members that may be separated by spacers (55). In FIG. 9, a sample can be applied to the device through the inlet opening (35) so that the sample contacts the conjugate pad (50) and because of the pressure the sample through vertical flow contacts the test membrane (45).

Figure 8A:
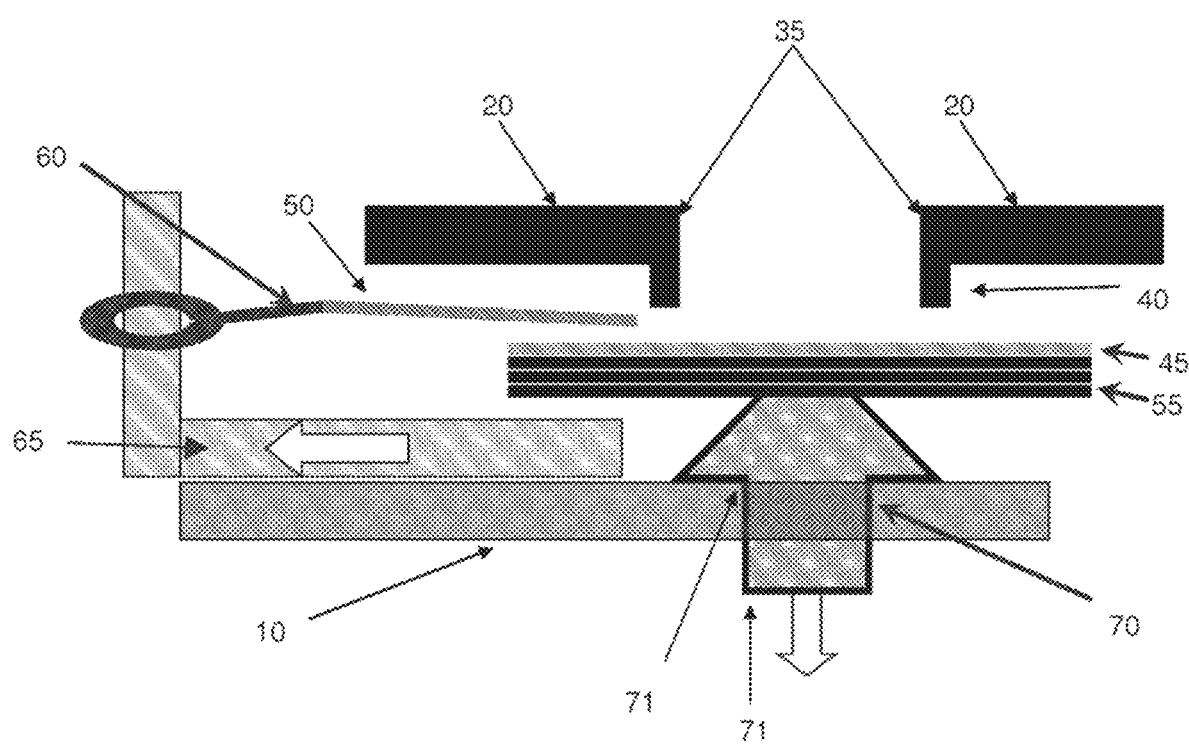
FIG. 8A: Depicts a lateral view of some components of a representative device according to some embodiments of the present invention.
Figure 8B:
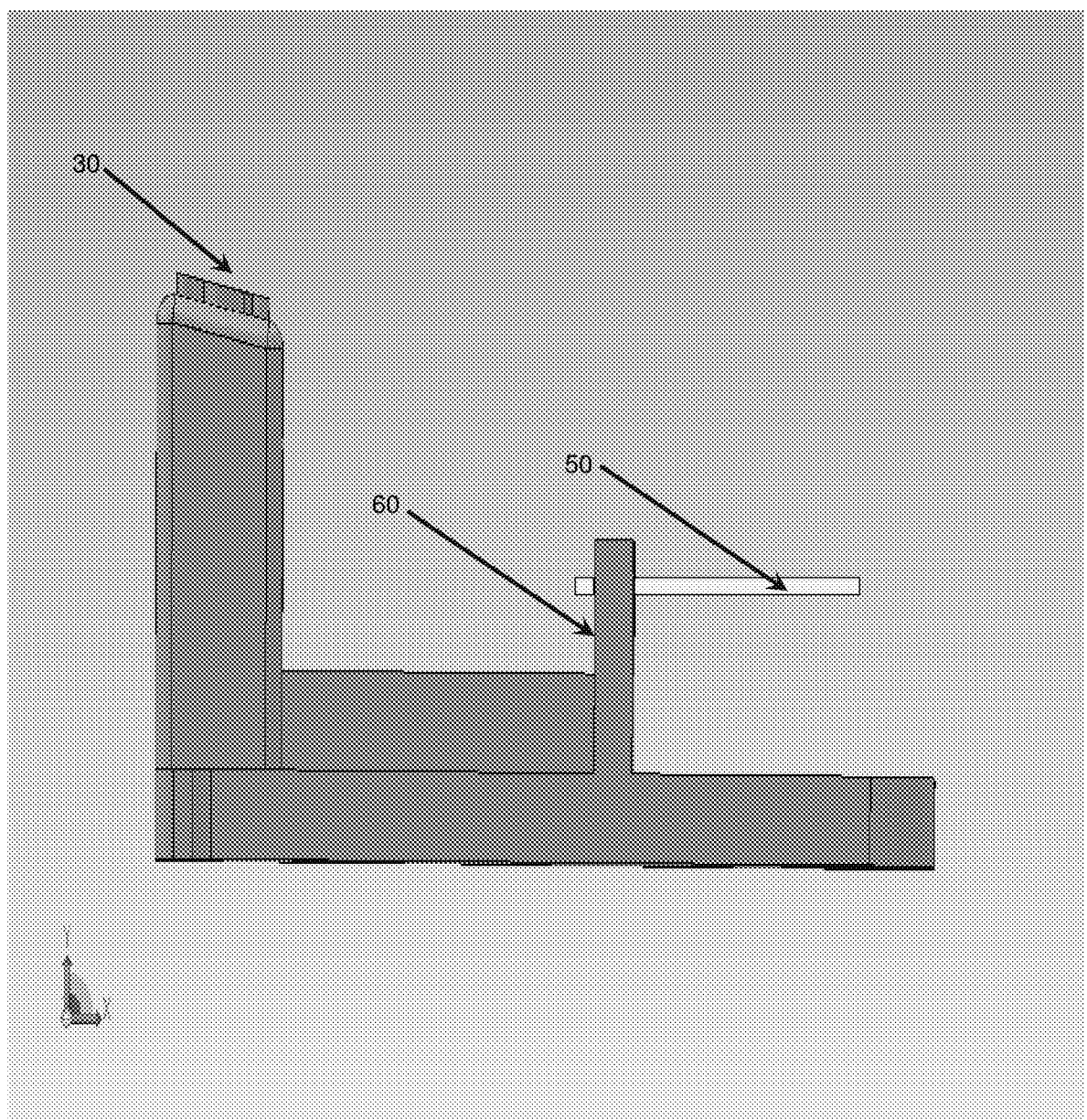
FIG. 8B: Depicts a view of some components, such as but not limited to, a non-flexible attachment member, of a representative device according to some embodiments of the present invention.

FIG. 8A depicts a partial view of a device comprising a first housing member (10), a second housing member (20), an inlet opening (35), a test membrane (45), a conjugate pad (50), a plurality of absorbent members that may be separated by spacers (55), an attachment member (60), a locking member (65), and a force member (70). FIG. 8 depicts the movement of the locking member (65), which is attached to the attachment member (60). The movement of the attachment member (60), which is attached to the conjugate pad (50) moves the conjugate pad. FIG. 8 depicts the test force member (70) changing positions and a lessening or elimination of the pressure and/or compression of the test membrane (45). FIG. 9 also depicts the movement of the conjugate pad (50) away from the inlet opening (35) revealing the test membrane (45) for visualization and/or detection.

Figure 8C:
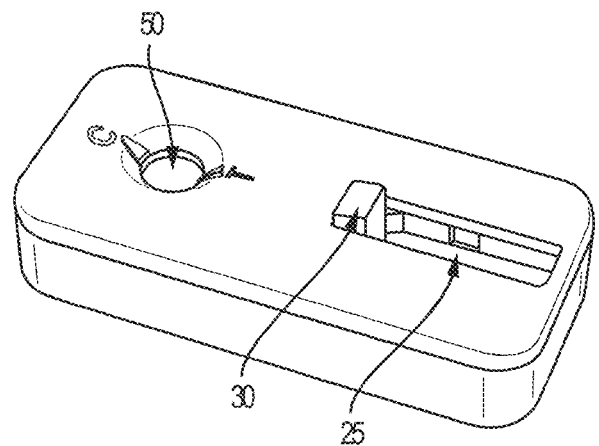
FIG. 8C: Depicts a perspective view of a representative device according to some embodiments of the present invention.
Figure 8D:
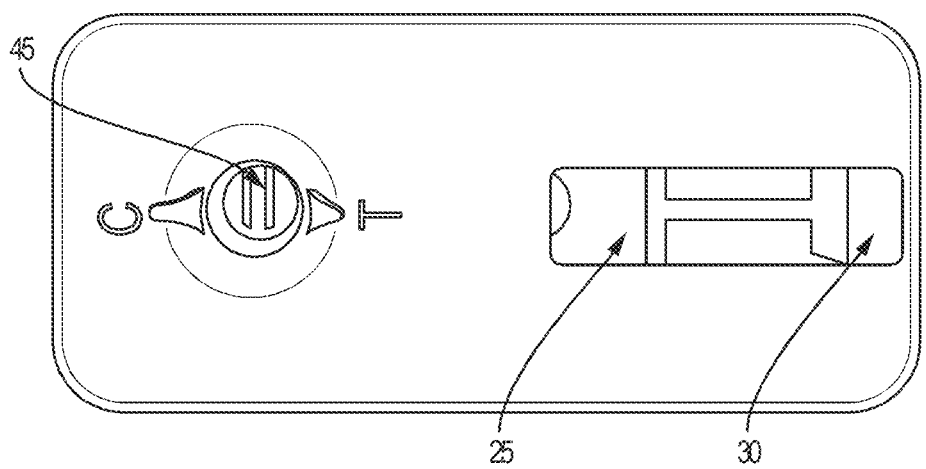
FIG. 8D: Depicts a perspective view of a representative device according to some embodiments of the present invention.
Figure 9:
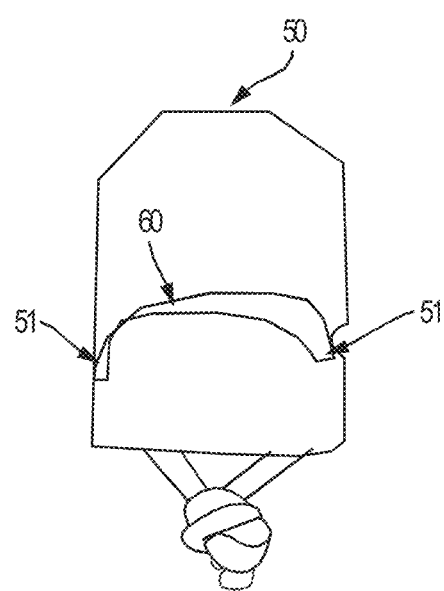
FIG. 9: Depicts a flexible attachment member attached to a conjugate pad.

FIG. 8C depicts a device comprising, in part, a conjugate pad (50), a sliding button (30), and the groove for the sliding button (25). Unseen in FIG. 8C are components similar to that shown in FIG. 8B. FIG. 8D depicts a device similar to that shown in FIG. 8C, except the sliding button (30) has been moved to move the conjugate pad and expose the test membrane (45).

FIG. 9 depicts an attachment member (60) attached to a conjugate pad (50). FIG. 9 depicts notches (51) in the conjugate pad (50) as locations for the attachment member (60) to attach to. The attachment member can also be attached through other means such as through adhesives, staples, and other forms of attachment.

Figure 10:
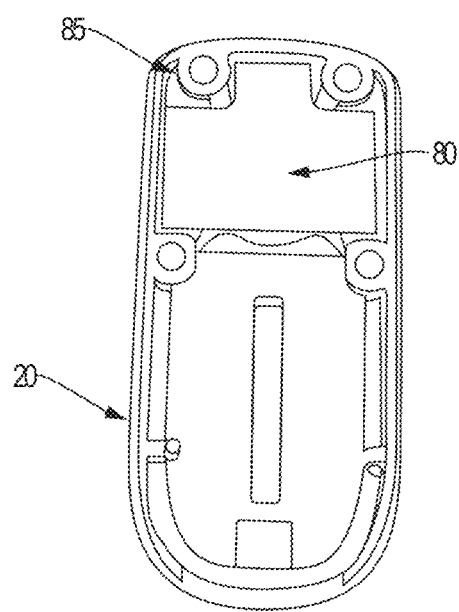
FIG. 10: Depicts membranes in a representative housing member.

FIG. 10 depicts a partial view of device comprising a second housing member (20), a plurality of pads or membranes (80), wherein the plurality of pads comprises a test membrane, a permeable membrane, and one or more absorbent members that may be separated by spacers, and retaining members (85) that can retain the plurality of pads or membranes (80). FIG. 10 depicts the structures that when the conjugate pad is moved the plurality of pads remains in place. Any means or other structure can be used to keep the plurality of pads in place.

Figure 11:
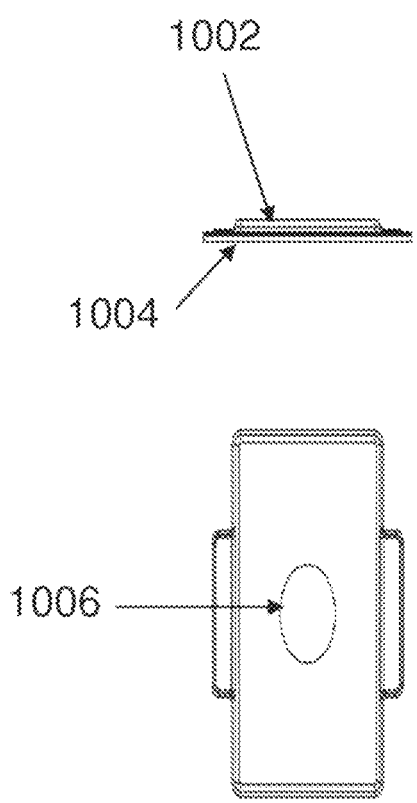
FIG. 11 depicts a side view and a top view of a representative device according to some embodiments of the present invention.

FIG. 11 depicts a representative device comprising a first housing member (1002) that further comprises a housing inlet (1006), and a second housing member (1004). In some embodiments, the first and second housing members can be constructed as a single unit. The housing inlet allows for the introduction of a sample onto the components inside the housing. The housing inlet can be of sufficient size to handle an appropriate amount of volume of a solution that is added to the device. In some embodiments, the size of the opening created by the housing inlet is sufficient to handle about 0.1 to about 3 ml, about 0.1 to about 2.5 ml, about 0.5 to about 2.0 ml, about 0.1 to about 1.0 ml, about 0.5 to about 1.5 ml, about 0.5 to about 1.0 ml, and about 1.0 to about 2.0 ml. In some embodiments, the dimensions of the device are such that any dimension (e.g., width, depth, or height) is less than or equal to about 5.08 cm (2.000 inches). In some embodiments, the height of the device is less than about 0.635 cm (0.250 inches), less than about 0.254 cm (0.100 inches), less than about 0.191 cm (0.075 inches), less than about 0.165 cm (0.065 inches), less than about 0.152 cm (0.06 inches), or less than about 0.140 cm (0.055 inches). In some embodiments, the height of the device is about 0.127 cm (0.050 inches). In some embodiments, the width or depth of the device is less than or equal to about 5.08 cm (2.000 inches), about 4.83 cm (1.900 inches), about 4.699 cm (1.850 inches), about 4.572 cm (1.800 inches), about 4.445 cm (1.750 inches), about 4.191 cm (1.650 inches), about 4.064 cm (1.600 inches), or about 3.81 cm (1.500 inches). In some embodiments, the device is about 0.127 cm (0.050 inches) in height, about 4.445 cm (1.750 inches) in depth, and about 3.81 cm (1.500 inches) in width.

In some embodiments, the device comprises a plurality of components comprising one or more of: a removable member, a conjugate pad, an adhesive member, a test membrane, an absorbent member(s), a force member, a support member, or any combination thereof.

In some embodiments, the device comprises a force member, a removable member, a conjugate pad, a test membrane, an adhesive member and/or an absorbent member(s). In some embodiments, the device comprises an analyte detection membrane system. In some embodiments, the analyte detection membrane system comprises a conjugate pad, a test membrane, and an absorbent member. In some embodiments, the analyte detection membrane system comprises an additional permeable membrane, but the device can also be free of a permeable membrane. In some embodiments, the analyte detection membrane system comprises in the following order: a conjugate pad, an adhesive member, a test membrane, and an absorbent member.

Figure 12:
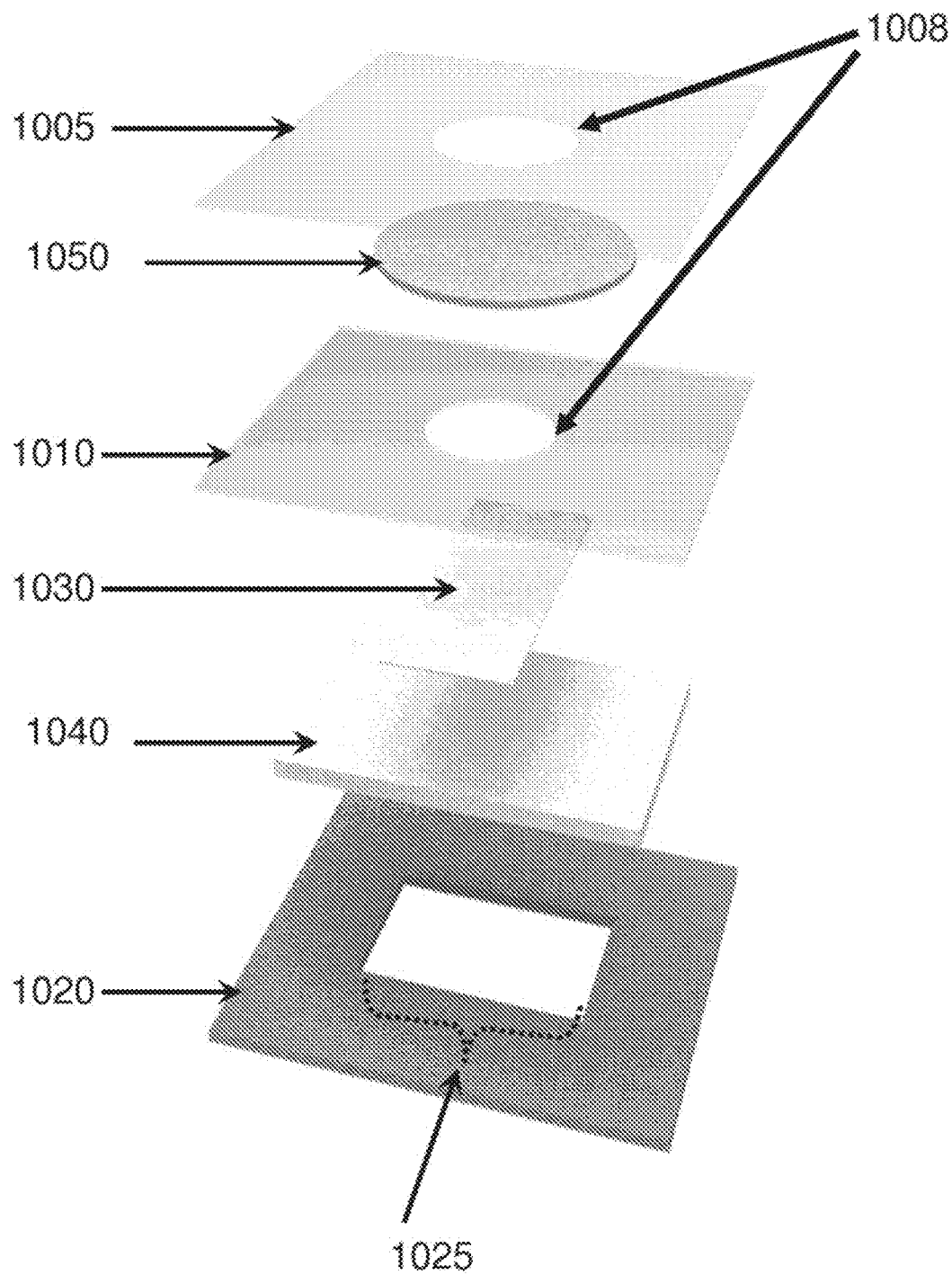
FIG. 12 depicts one type of analyte detection membrane system for a representative device according to some embodiments of the present invention.

FIG. 12 depicts an exploded view of the inside of a representative device comprising a removable member (1005), a conjugate pad (1050), an adhesive member (1010), a test membrane (1030), an absorbent member (1040), and a support member (1020), wherein the support member further comprises an optional support member inlet (1025). The removable member and the adhesive member can also comprise optional removable member inlet (1008) and adhesive member inlet (1012), respectively. Such components could reside within, for example, the device of FIG. 11.

Figure 13:
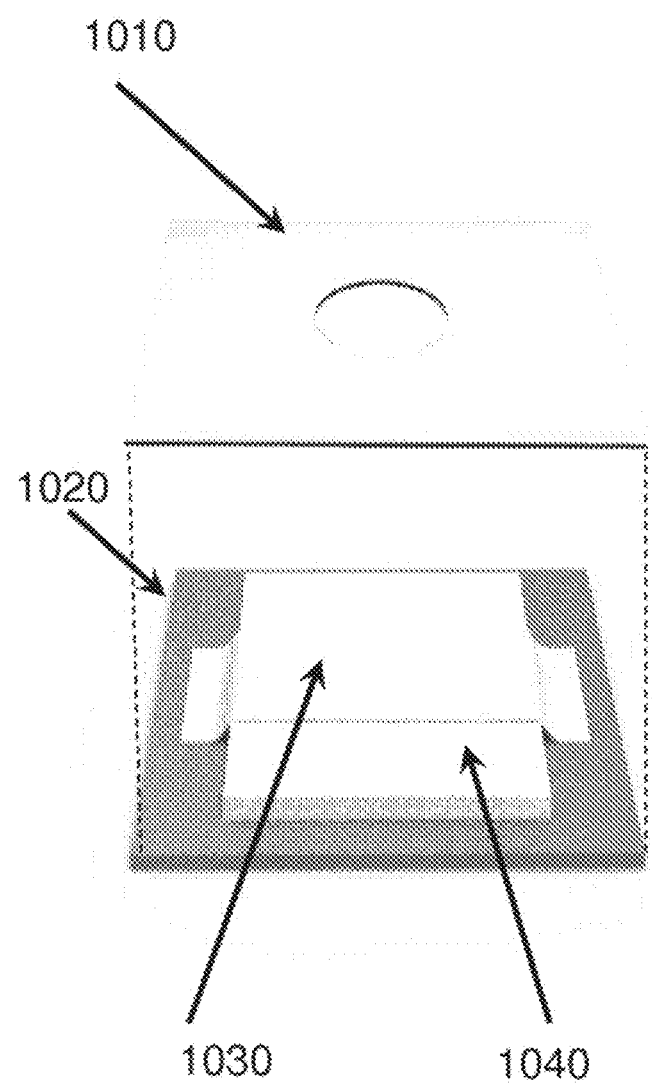
FIG. 13 depicts one type of analyte detection membrane system for a representative device according to some embodiments of the present invention.

FIG. 13 depicts representative components of another representative device comprising an adhesive member (1010), a support member (1020), a test membrane (1030), and an absorbent member (1040). As can be seen in FIG. 13, a sample can flow through the adhesive member (1010) and contact the test membrane (1030).

Figure 14:
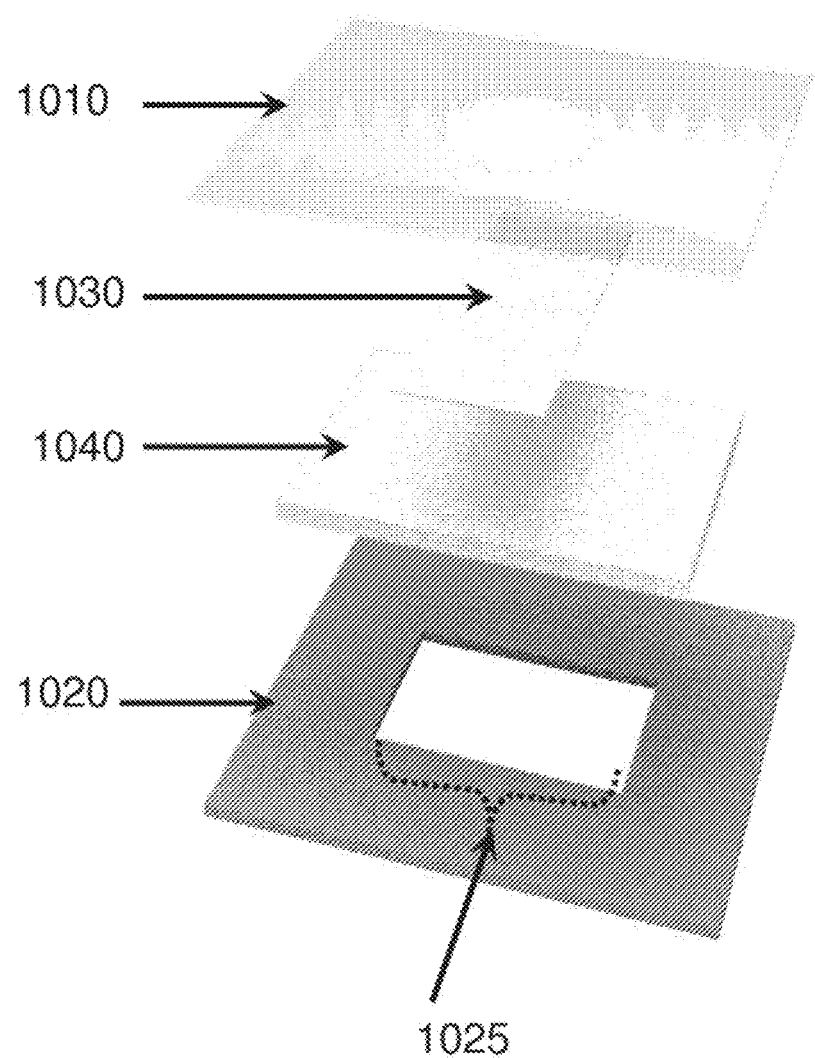
FIG. 14 depicts one type of analyte detection membrane system for a representative device according to some embodiments of the present invention.

FIG. 14 depicts an adhesive member (1010), a support member (1020), a test membrane (1030), and an absorbent member (1040). FIG. 14 depicts the components being substantially parallel with one another. FIG. 14 further depicts the support member (1020) comprising a support member inlet (1025). This inlet can be used to allow the sample to vertically flow through the device.

Figure 15:
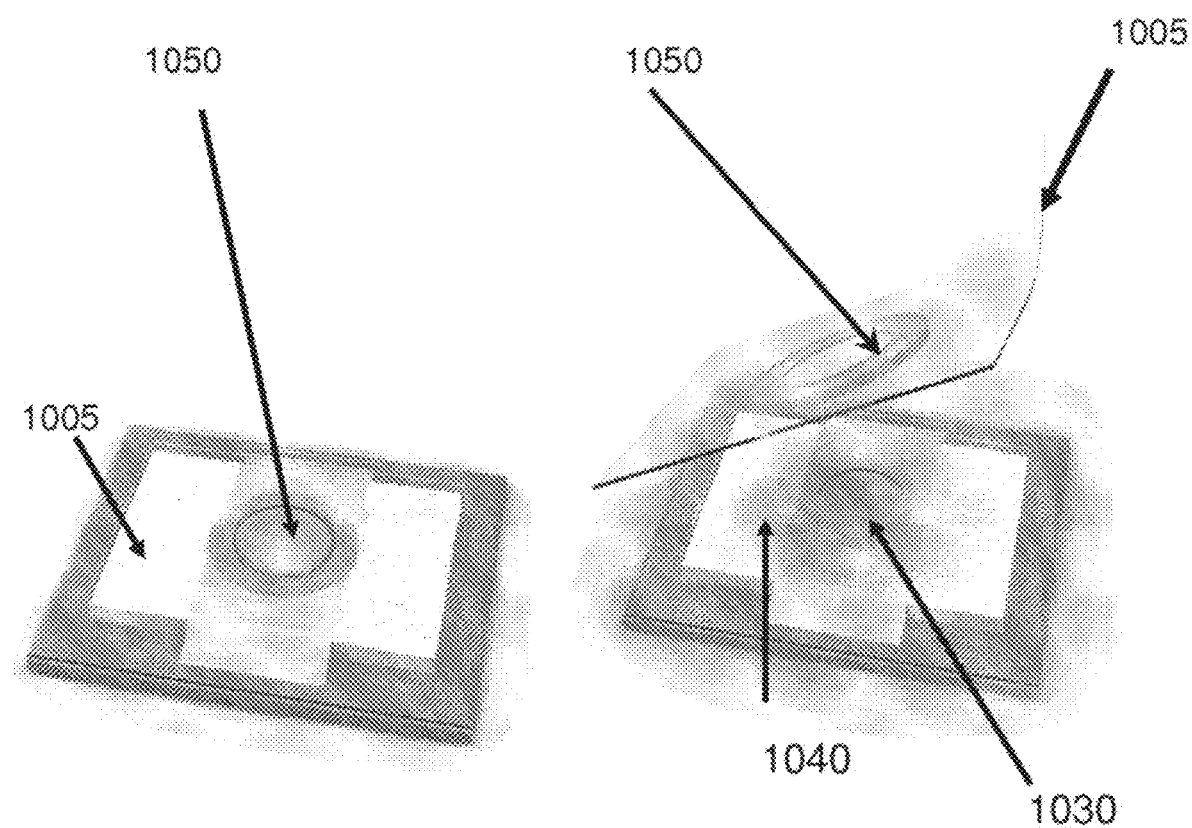
FIG. 15 depicts one type of analyte detection membrane system for a representative device according to some embodiments of the present invention.

FIG. 15 depicts, in part, a conjugate pad (1050), a test membrane (1030), and an absorbent member (1040). FIG. 15 also depicts the conjugate pad in contact and/or attached to a removable member (1005). FIG. 15 also depicts the removable member being removed or moved away from the device, which also removes or moves away from the device the conjugate pad. The movement of the conjugate pad allows the test membrane to be visualized, which facilitates analysis and detection of analytes.

FIG. 16 depicts examples of force members. Representative force members can come in a variety of shapes, sizes, and configurations, but each member applies pressure on the components that are placed in or on the force member. Each force member can also comprise an opening (+) into which the analyze sample is applied. FIG. 16 depicts non-limiting examples of force members with a first member (110) and a second member (100).

Figure 17A:
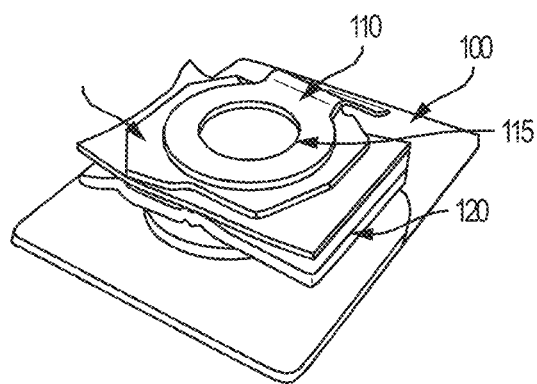
FIGS. 17A-17D depict a representative device according to some embodiments of the present invention.
Figure 17C:
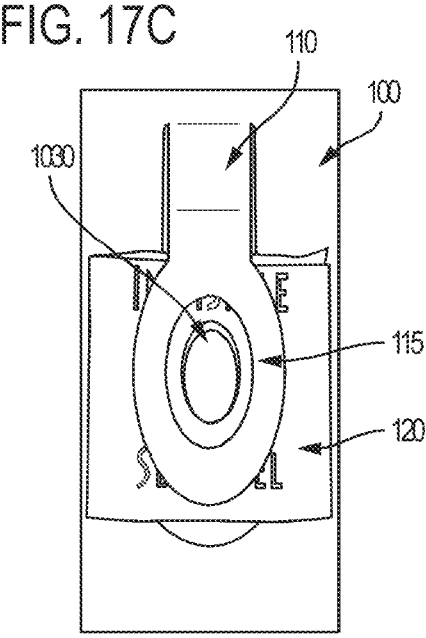
Figure 17B:
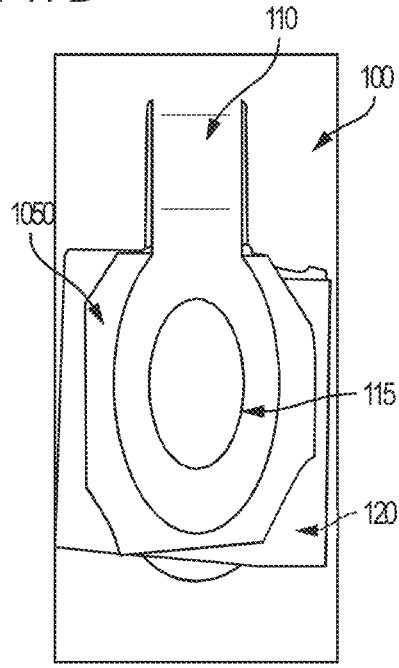
Figure 17D:
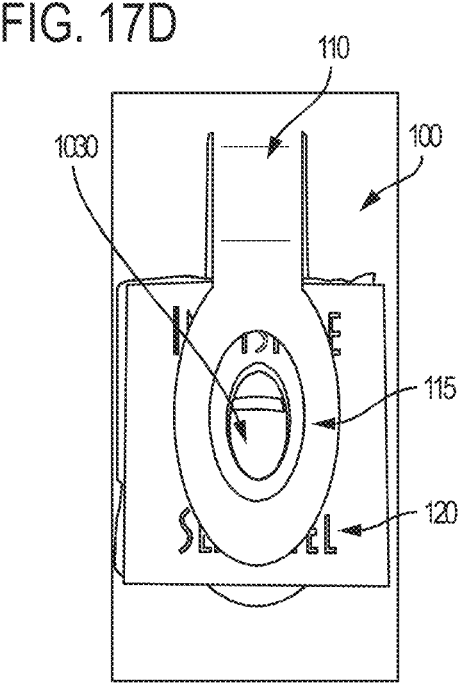

FIGS. 17A, 17B, 17C, and 17D depict, in part, a force member comprising a first member (110), b) a second member (100), an inlet (115), and an analyte detection membrane system (120). FIGS. 17A and 17B also depict, in part, a conjugate pad (1050). The conjugate pad is not seen in FIGS. 17C and 17D. FIGS. 17C and 17D also depict, in part, a test membrane (1030) that is part of the analyte detection membrane system. FIG. 17D also depicts in part, a test membrane (1030) that has been reacted with a control, which is visualized by the band.

FIG. 18 depicts, in part, a container comprising a removable or movable tab (200), an inlet (210), a conjugate pad (1050), and the tab of the conjugate pad (1050). The tab of the conjugate pad (255) can be used to remove the conjugate pad (1050) from the device to expose the test membrane. For example, a user could pull the tab of the conjugate pad (255) to remove the conjugate pad (1050) from the container. What is not visualized is the analyte detection membrane system that is compressed between a first member (110) and a second member (100) as described herein.

FIG. 19 depicts, in part, a first outer member (310), a second outer member (320), a movable or removable tab (330), and a conjugate pad (1050). The movable or removable tab (330) comprises an inlet that exposes the conjugate pad (1050) so that the sample can be applied to the conjugate pad. FIG. 19 does not show the first inner member (110) and the second inner member (100) compressing the analyte detection membrane system (120). The removable or movable tab (330) when moved or removed, moves or removes the conjugate pad (1050), which allows the test membrane to visualized and analyzed.

The removable member inlet within the removable member allows the introduction of a sample onto the conjugate pad. The inlet can be of sufficient size to handle an appropriate amount of volume of a solution that is added to the device. In some embodiments, the size of the inlet is large enough to handle about 0.1 to about 3 ml, about 0.1 to about 2.5 ml, about 0.5 to about 2.0 ml, about 0.1 to about 1.0 ml, about 0.5 to about 1.5 ml, about 0.5 to about 1.0 ml, and about 1.0 to about 2.0 ml. The removable member can also be constructed such that a portion of the removable member is permeable to solutions (i.e., the area defined by the removable member inlet) and another area is impermeable. The permeable area can act as an inlet because it would allow solutions to cross the removable member and contact the conjugate pad. The removable member inlet can have any one of numerous shapes and sizes. In some embodiments, the first housing member serves as the removable member. In other embodiments, the first housing member and the removable member are separate components. In embodiments where the first housing member and the removable member are separate components, at least a portion of the housing inlet and removable member inlet overlap such that a solution can enter through both inlets.

In some embodiments, the removable member contacts a first surface of a conjugate pad. The removable member can also be attached to the conjugate pad. The removable member can be attached to the conjugate pad by any means such that when the removable member is removed from the device or its position is changed, the conjugate pad is also removed or the position of the conjugate pad is also changed. The removable member can be attached to the conjugate pad with, for example, but not limited to, an adhesive. Adhesives include, but are not limited to, glue, tape, or other substance that would allow the removable member and the conjugate pad to be attached to one another.

The removable member, in some embodiments, directly contacts the conjugate pad or indirectly contacts the conjugate pad through another layer. The sample can be, in some embodiments, directly applied to the conjugate pad through the opening in the removable member.

Figure 20A:
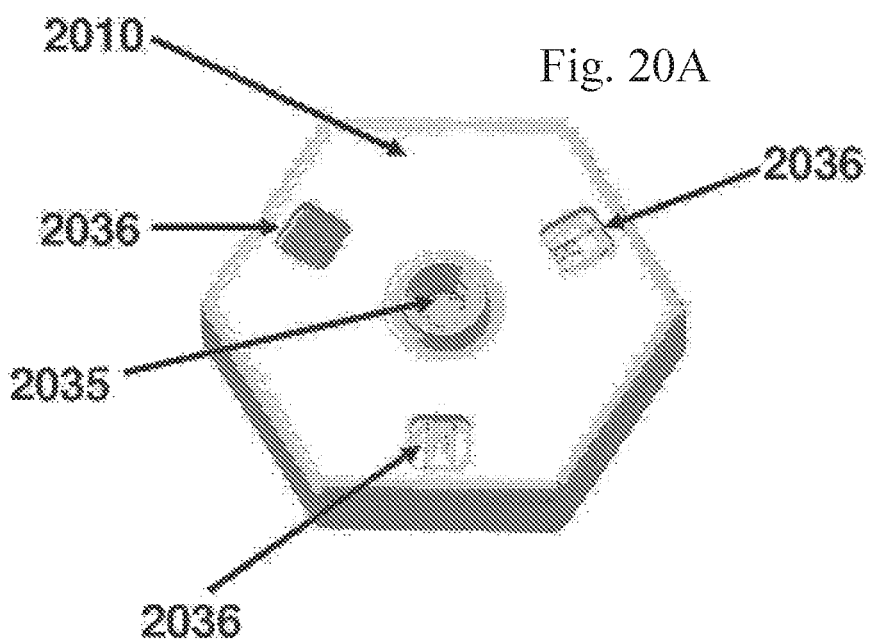
FIGS. 20A-20B depict a view of a representative device according to some embodiments of the present invention.
Figure 20B:
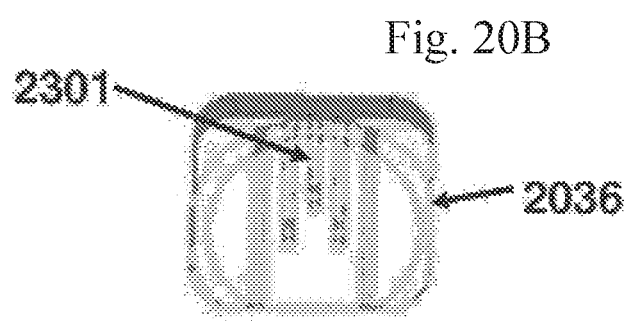

FIG. 20A depicts, in part, an overhead view of a device comprising a plurality of portals (2036), an inlet (2035), and a housing member (2010). FIG. 20A also depicts, in part, a portion of the channel system (2300) that is visible through the portal (2301). FIG. 20B depicts, in part, an enlarged area of the device, specifically, the portal (2036). In the portal one can also see a plurality of capillary tubes (2301).

Figure 21:
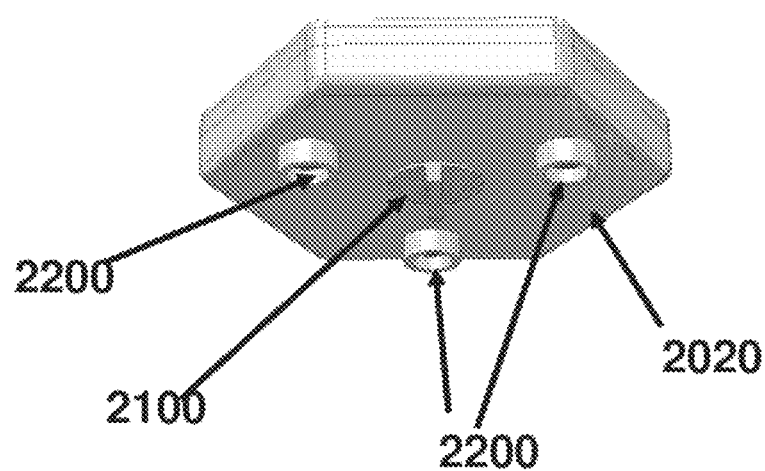
FIG. 21 depicts an underneath view of a representative device according to some embodiments of the present invention.

FIG. 21 depicts an underneath view of a device comprising a plurality of force actuator outlets (2200), a housing member (2020), and a moving member (2100).

Figure 22:
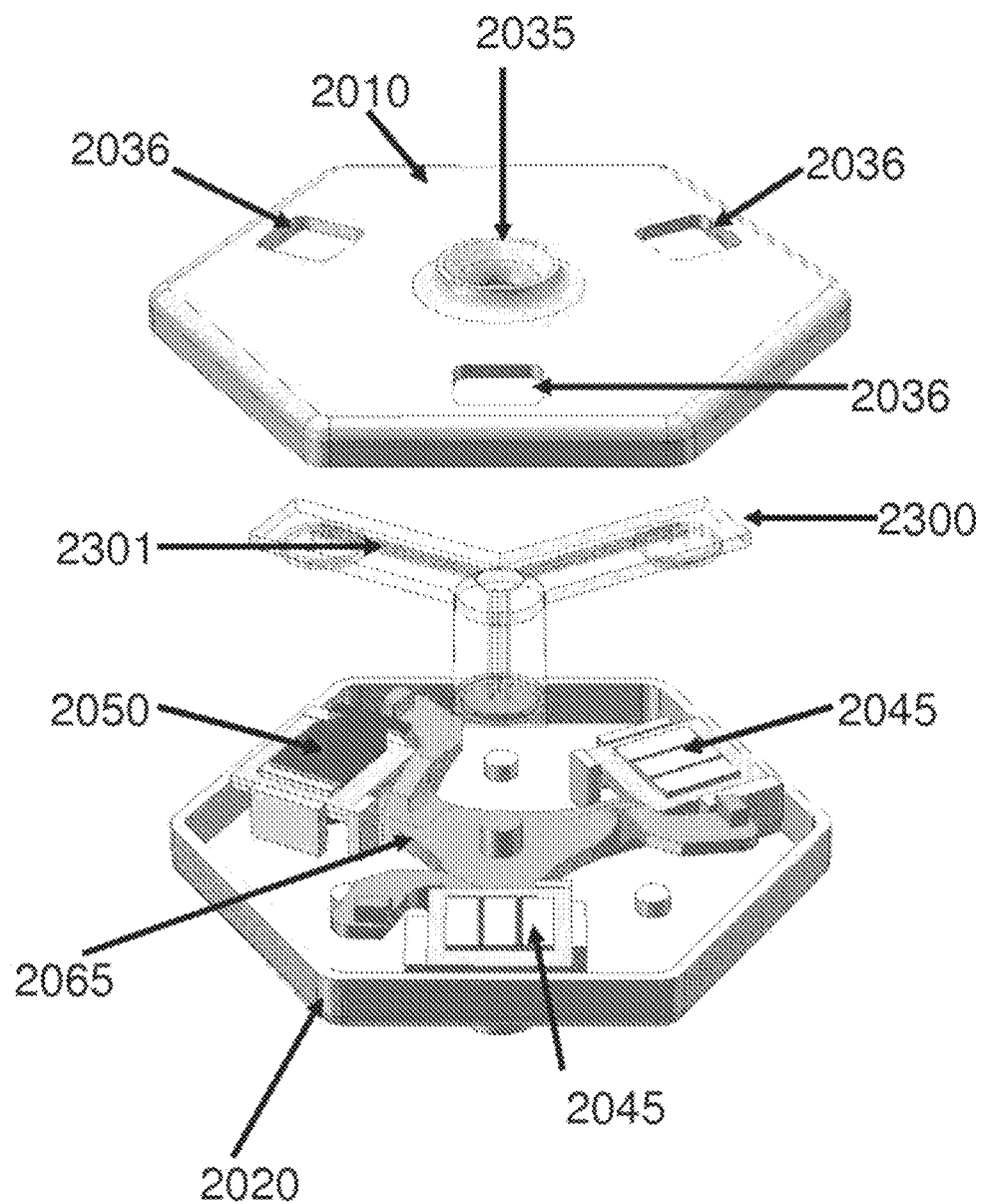
FIG. 22 depicts an exploded view of a representative device according to some embodiments of the present invention.

FIG. 22 depicts, in part, a first housing member (2010), a second housing member (2020) a plurality of portals (2036), an inlet (2035), a channel system (2300), a plurality of capillary tubes (2301), a conjugate pad (2050), a plurality of test membranes (2045), and movable locking member (2065). The channel system depicted in FIG. 22 is depicted as consisting 3 branches, which is equal to the number of analyte detection membrane systems present in the device.

Figure 23:
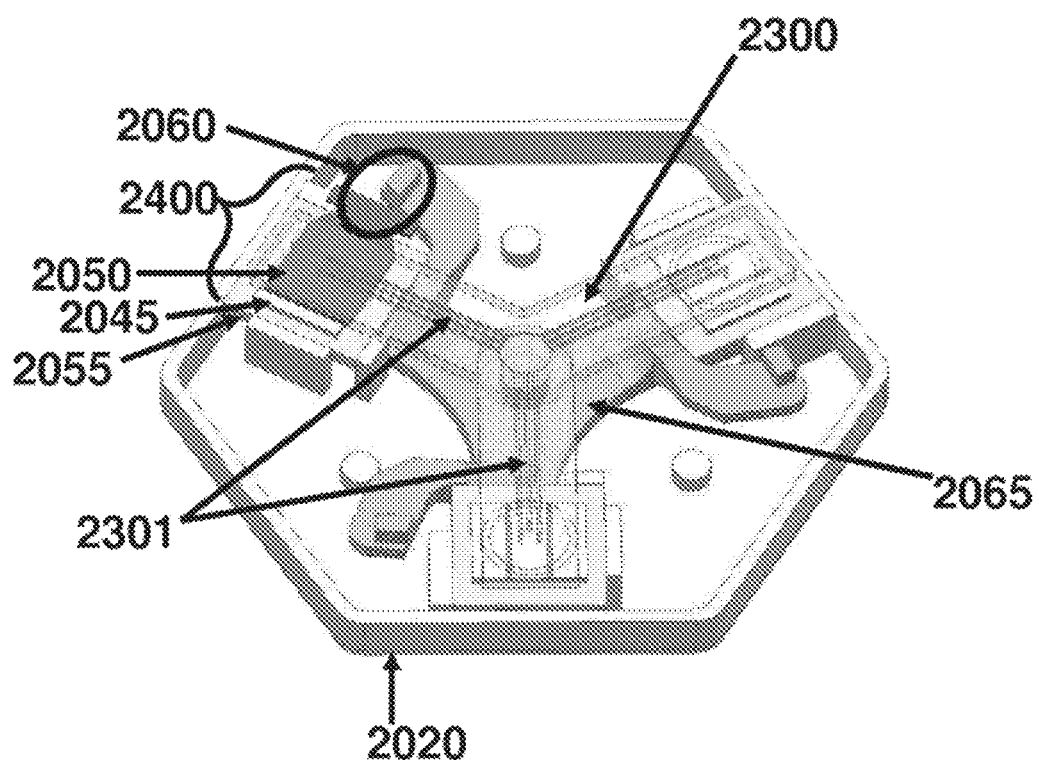
FIG. 23 depicts an interior view of a representative device according to some embodiments of the present invention.

FIG. 23 depicts, in part, a second housing member (2020), a channel system (2300), a plurality of capillary tubes (2301), a conjugate pad (2050), a test membrane (2045), and an absorbent membrane (2055), and a movable locking member (2065), a flexible attachment member (2060), an analyte detection membrane system (2400)

Figure 24A:
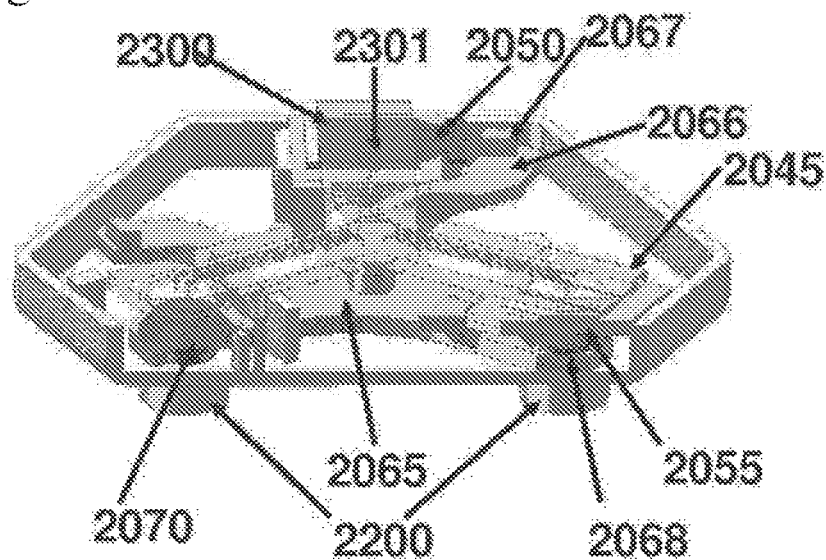
FIGS. 24A-24B depict a cross-sectional view of a representative device according to some embodiments of the present invention.

FIG. 24A depicts, in part, a plurality of force actuator outlets (2200), a channel system (2300), a plurality of capillary tubes (2301), a plurality of force members (2070), a movable locking member (2065), a plurality of movable locking member extensions (2068), a conjugate pad (2050), a plurality of flexible or non-flexible attachment member extensions (2066) and nodule (2067), a test membrane (2045), and absorbent membrane (2055).

Figure 24B:
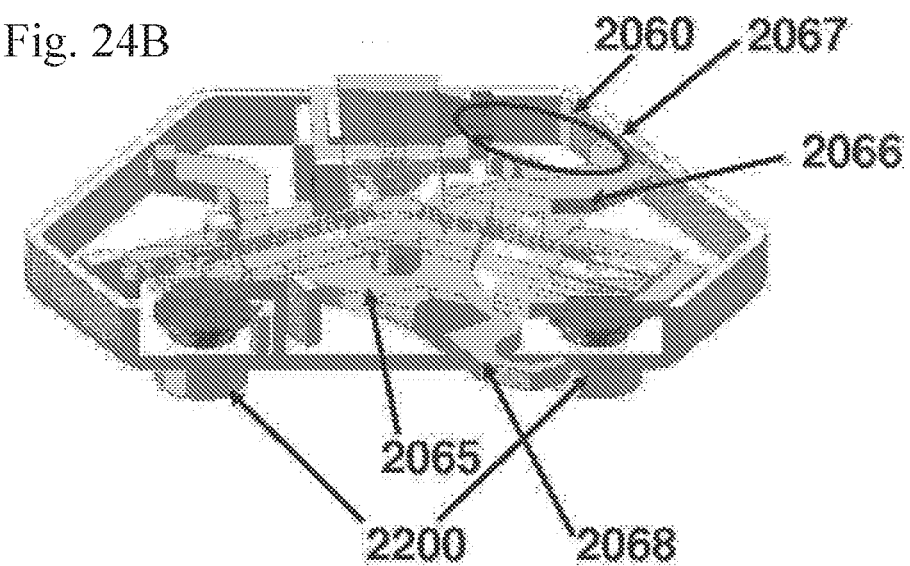

FIG. 24B depicts, in part, a similar portion of the device shown in FIG. 24A, however, the movable locking member (2065) has been rotated around a central axis and the movable locking member extension (2068) no longer supports the force member (2070) and the force member has receded or dropped into the force actuator outlet (2200).

Figure 25A:
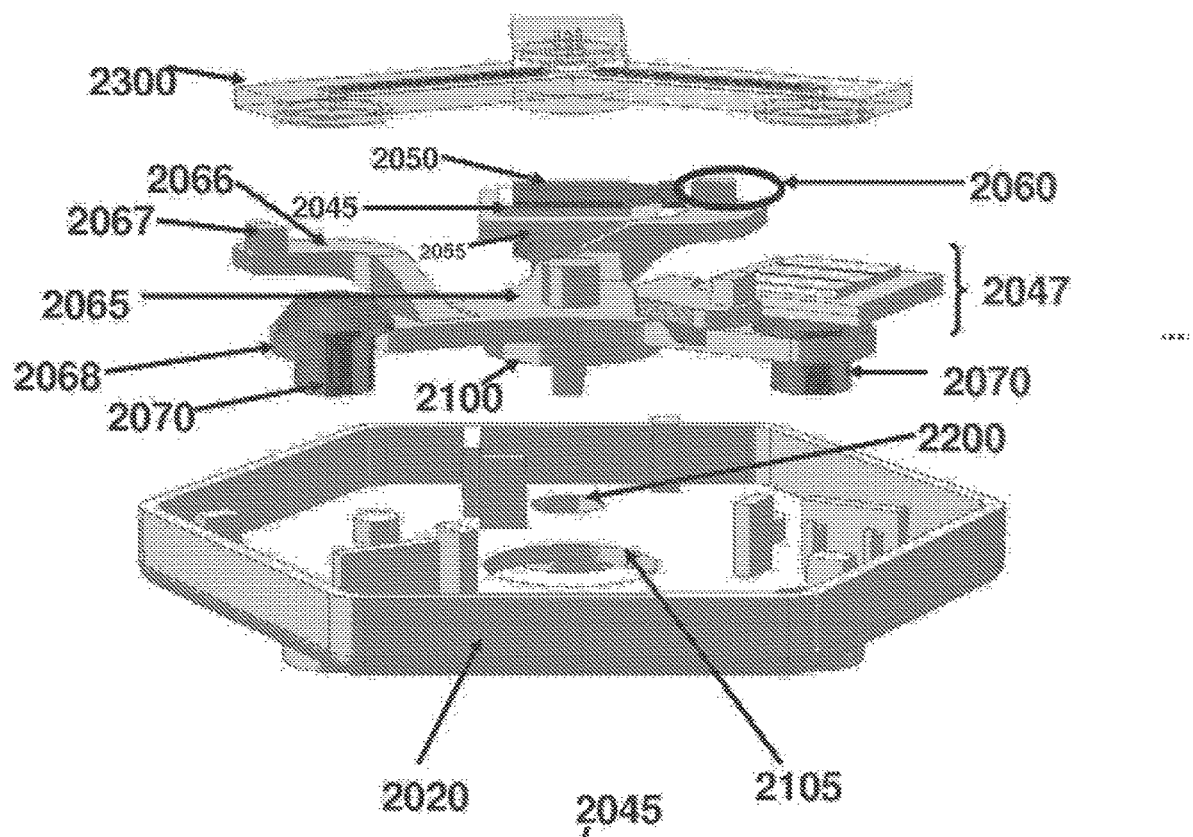
FIGS. 25A-25B depict an exploded view of a representative device according to some embodiments of the present invention.
Figure 25B:
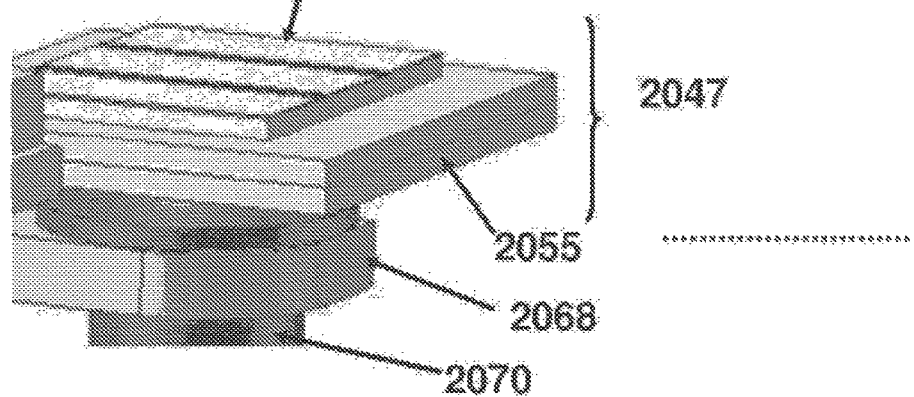

FIG. 25 depicts, in part, an exploded view of a device comprising a channel system (2300), a conjugate pad (2050), a test membrane (2045), a plurality of force members (2070), a movable member (2100) that can turn the movable locking member depicted (2065). FIG. 25 also depicts, in part, movable locking member extension (2068), a plurality of flexible or non-flexible attachment member extensions (2066) and nodule (2067), a flexible attachment member (2060), an outlet (2105), a second housing member (2020), a plurality of force actuator outlets (2200), and a portion of an analyte detection membrane system (2047). The area comprising the portion of the analyte detection membrane system (2047) has been enlarged and depicts, in part, a force member (2070), a test membrane (2045), an absorbent member (2055), and portion of the movable locking member extension (2068).

Figure 26A:
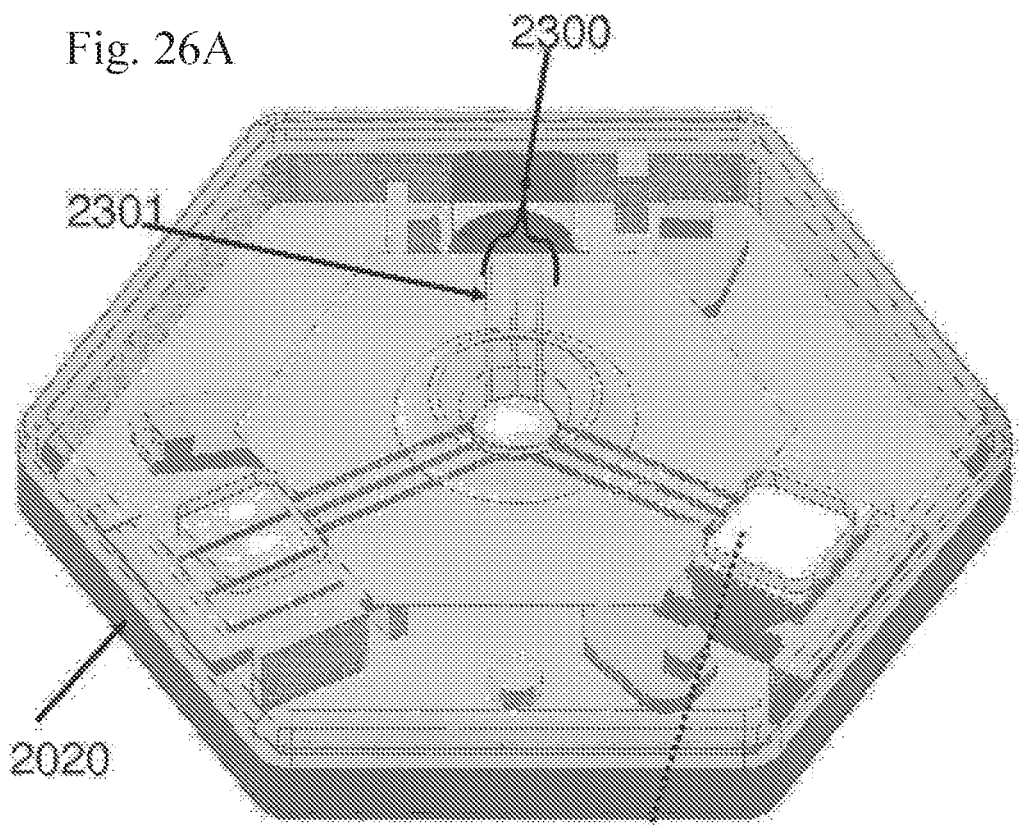
FIGS. 26A-26B depict an interior view of a representative device according to some embodiments of the present invention.
Figure 26B:
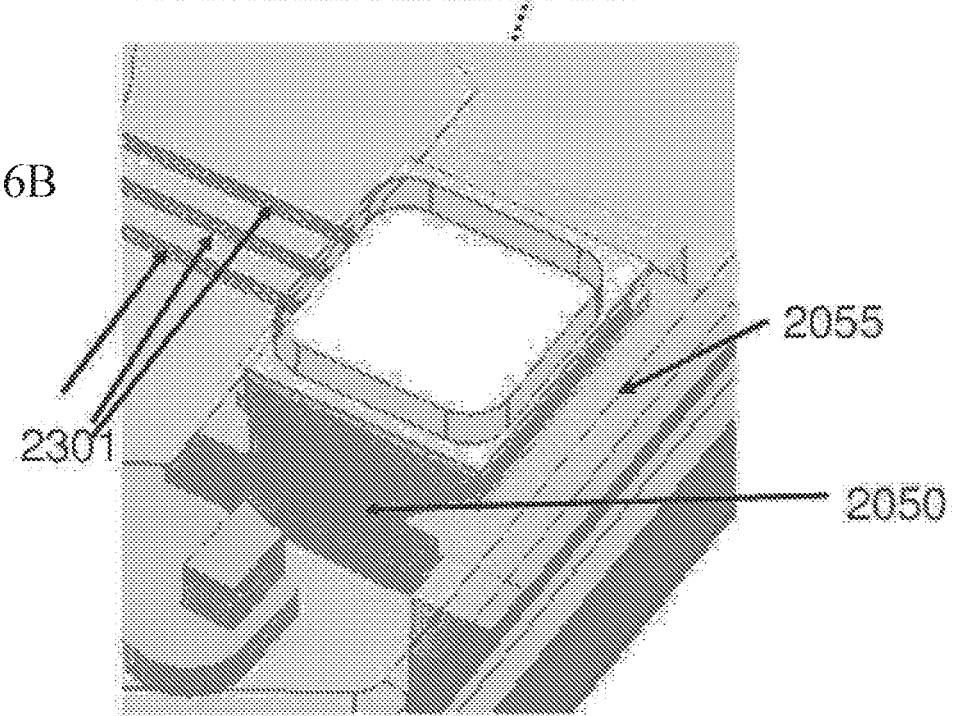

FIG. 26 depicts, in part, a housing (2020), a capillary channel (2301) and the channel system (2300). A portion of FIG. 26 has been enlarged to depict the conjugate pad (2050), the absorbent member (2055), and a plurality of capillary tubes (2301).

FIG. 27 depicts, in part, a cross-sectional view of a device comprising a plurality of portals (2036), an inlet (2035), a movable locking member (2065), a movable member that can move the movable locking member (2100), a force member (2700), a force actuator outlet (2200), a plurality of absorbent members (2055), a test membrane (2045), and a movable locking member extension (2068). FIG. 27 also depicts an exploded view of a portion of the analyte detection membrane system comprising a conjugate pad (2050), a permeable membrane (2056), and an absorbent member (2055).

Figure 28:
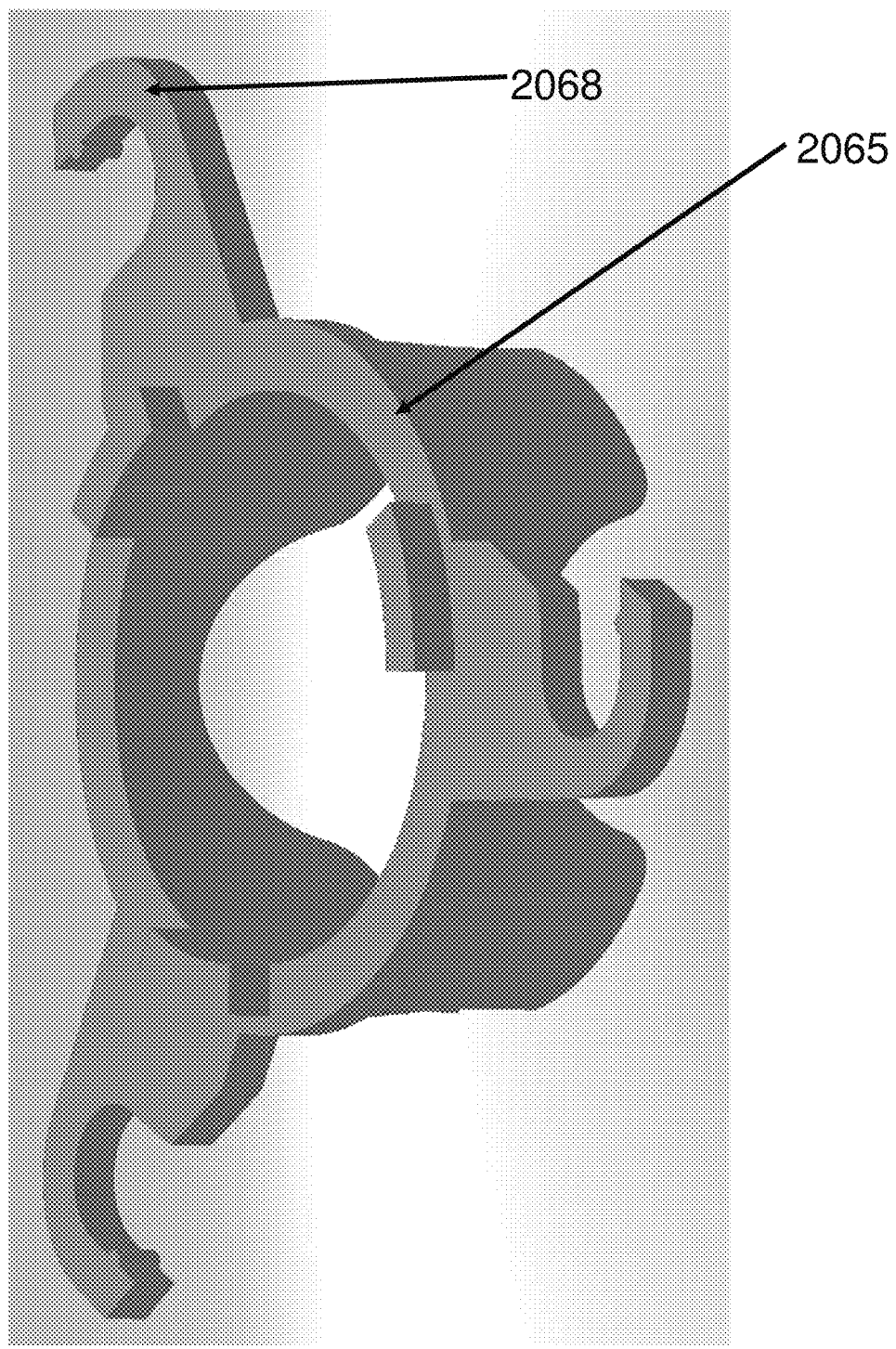
FIG. 28 depicts a representative movable locking member according to some embodiments of the present invention.

FIG. 28 depicts, in part, a non-limiting example of a movable locking member (2065) and a movable locking member extension (2068).

Figure 29:
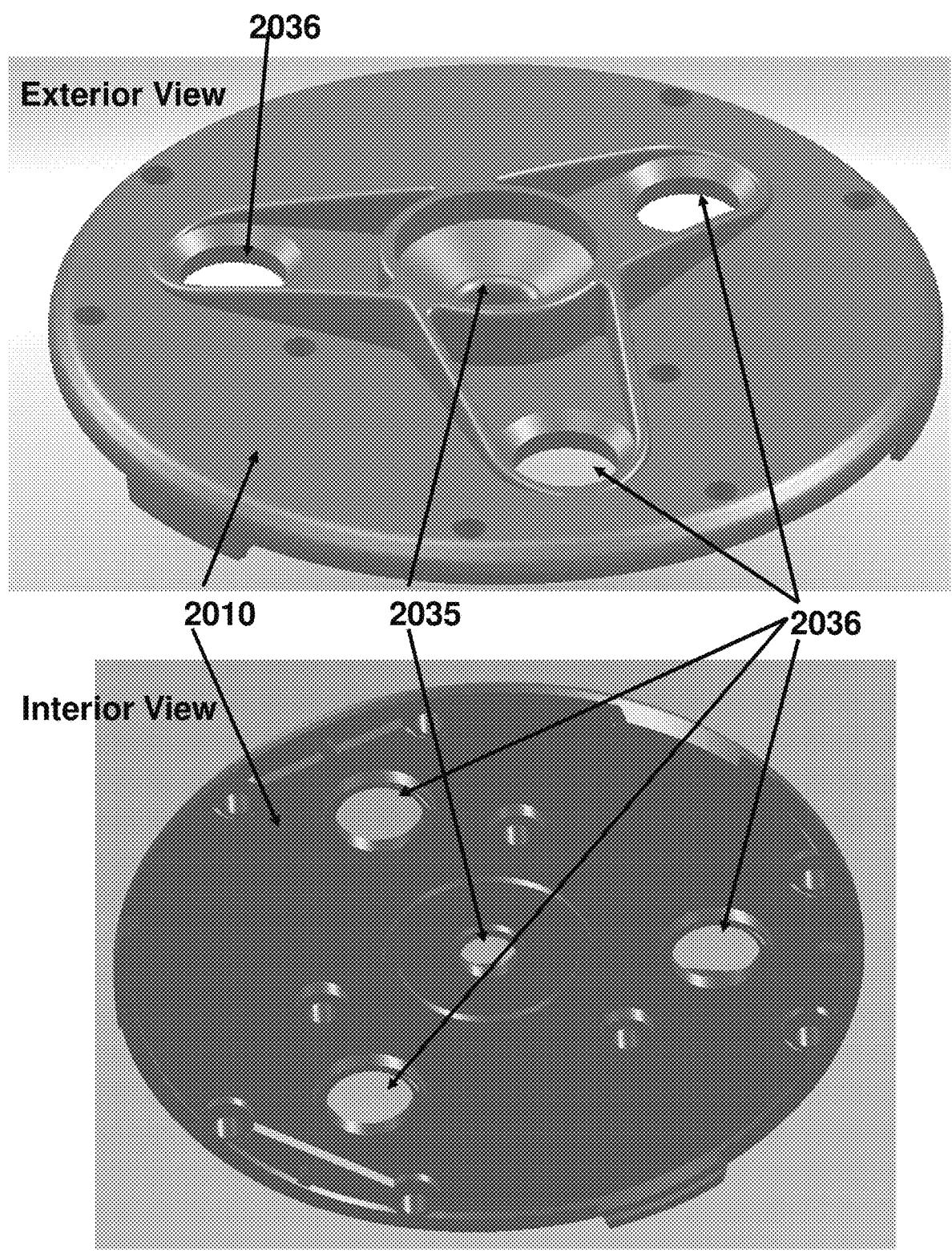
FIGS. 29A-29B depict a representative housing according to some embodiments of the present invention.

FIG. 29 depicts, in part, an exterior view and an interior view of a housing comprising a plurality of portals (2036) and an inlet (2035).

Figure 30:
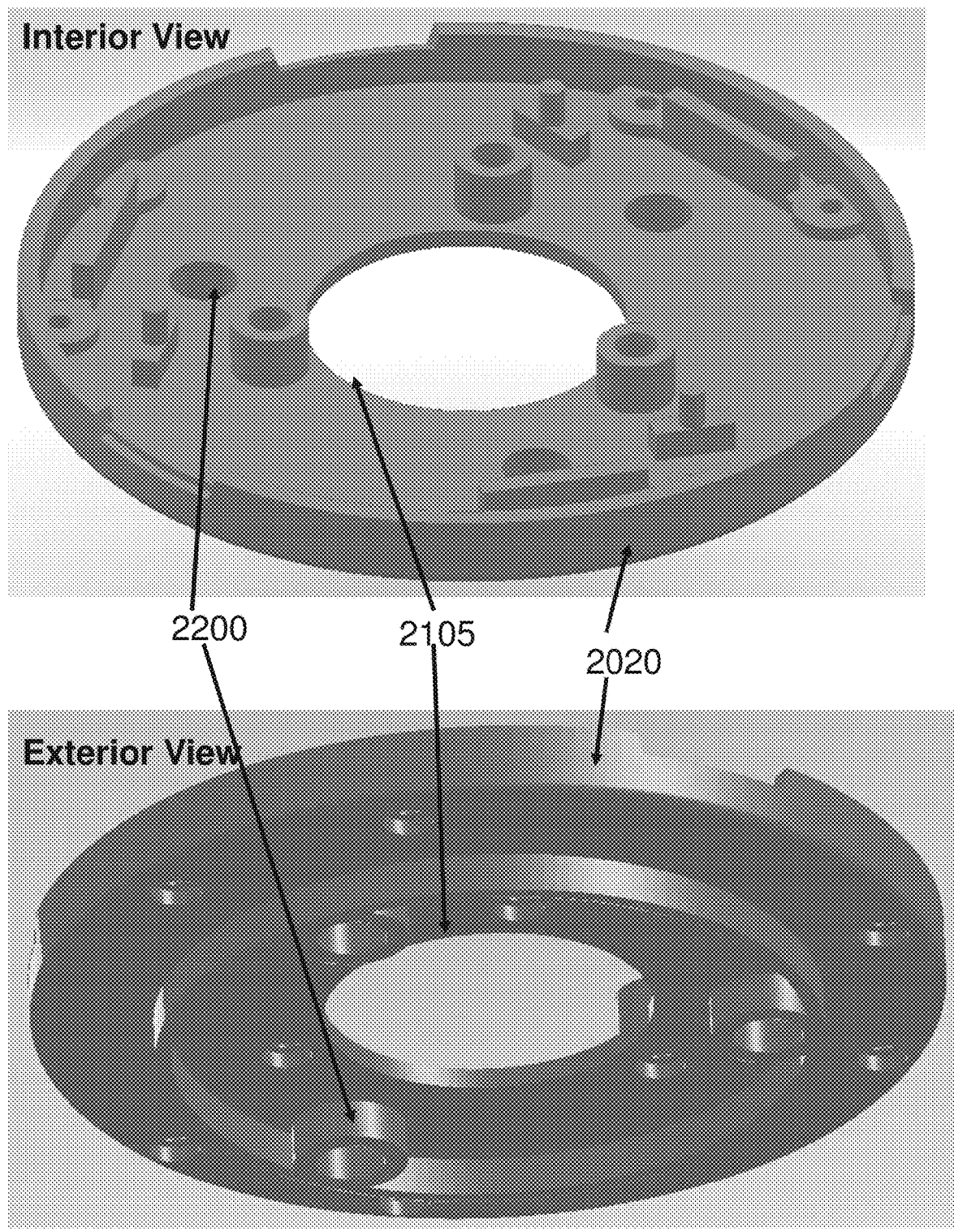
FIGS. 30A-30B depict a representative housing according to some embodiments of the present invention.

FIG. 30 depicts, in part, an interior view and an exterior view of a housing comprising a plurality of force actuator outlets (2200) and a movable member outlet (2105).

Figure 31A:
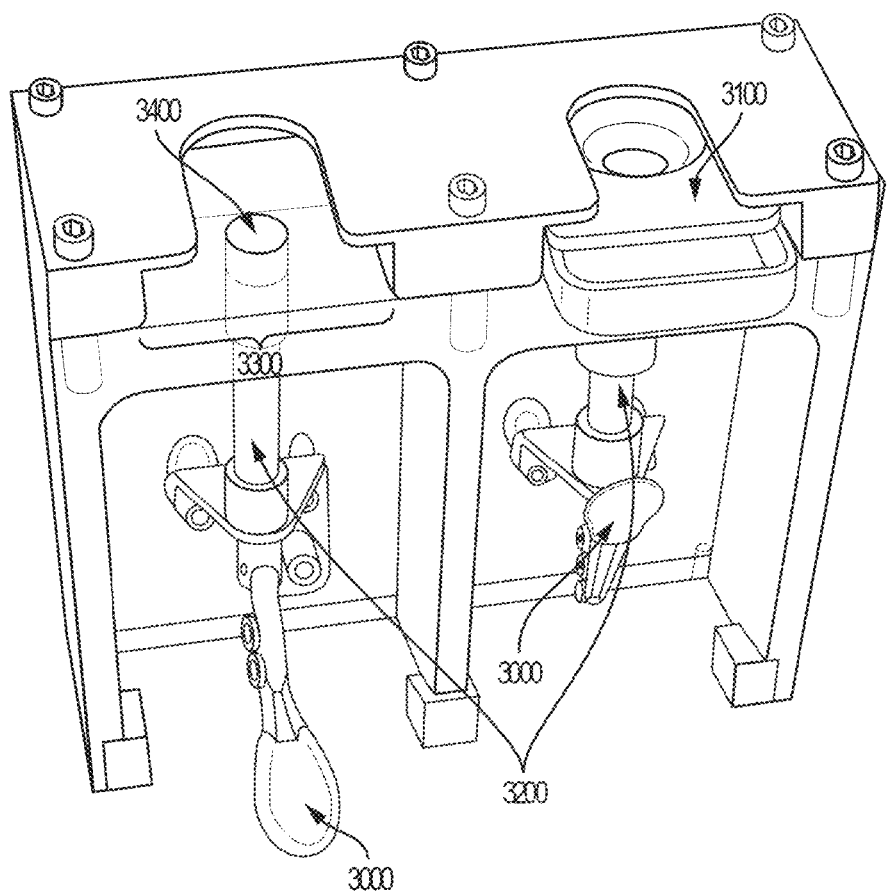
FIG. 31A depicts a representative device according to some embodiments of the present invention.

FIG. 31A depicts, in part, a device comprising a cartridge (3100) that can encompass an analyte detection membrane system, a force actuator (3200) and force release (3000), and outlet (3400), and an analyte detection membrane system receptacle (3300).

Figure 31B:
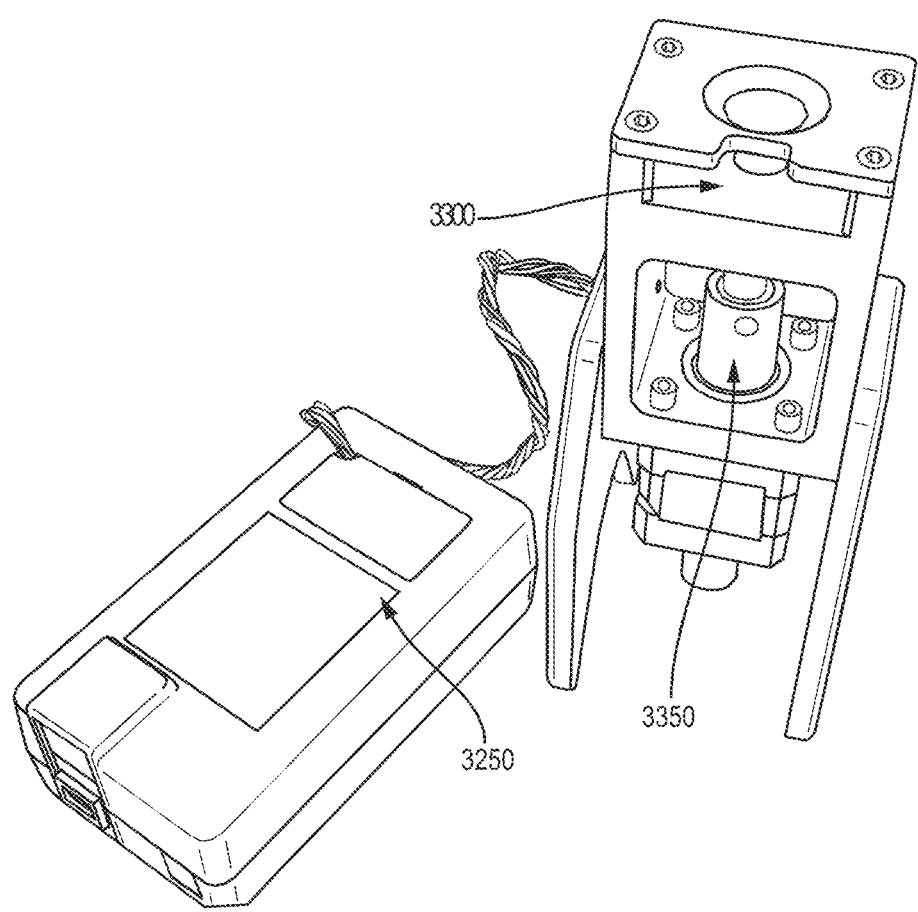
FIG. 31B depicts a representative device according to some embodiments of the present invention.

FIG. 31B depicts, in part, a device comprising a controller (3250) operably linked to the force actuator and release. The controller (3250) controls the pressure and/or vacuum applied to the cartridge or analyte membrane detection system. The controller, therefore in some embodiments, can control the flow rate of the sample as it passes through the analyte membrane detection system. FIG. 31B shows a piston (3350) that can be controlled by the controller. The piston can apply pressure to the cartridge that can be inserted into the cartridge receptacle (3300). The pressure can be increased or decreased to modulate or tune the flow rate. As discussed herein, the flow rate can also be modulated using vacuum force or other types of force.

Figure 32:
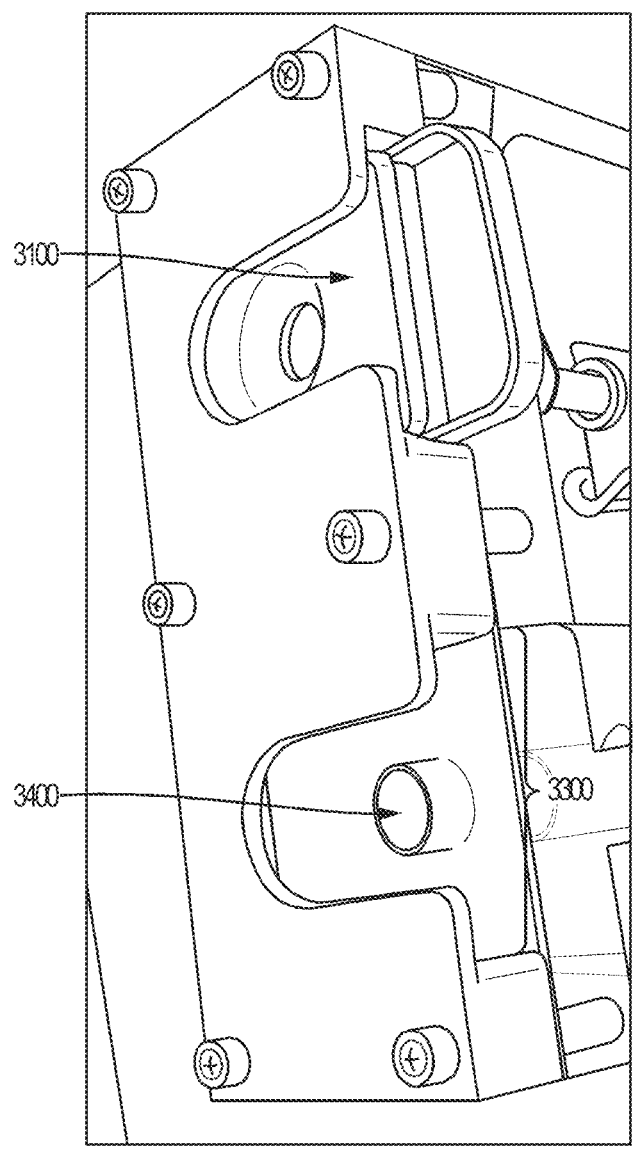
FIG. 32 depicts an enlarged view of a representative device according to some embodiments of the present invention.

FIG. 32 depicts, in part, an enlarged view of the outlet (3400), the receptacle (3300), and the cartridge (3100) depicted in FIG. 31.

Figure 33:
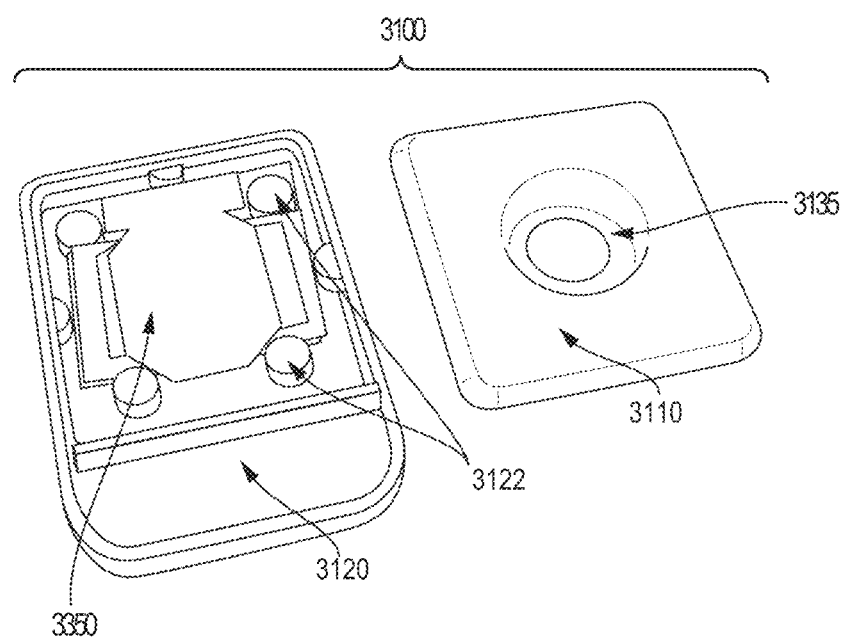
FIG. 33 depicts an exploded view of a cartridge and analyte detection membrane system according to some embodiments of the present invention.

FIG. 33 depicts, in part, an exploded view of a cartridge (3100) comprising a first housing member (3110), an inlet (3135), a conjugate pad (3350), a second housing member (3120), and a plurality of a membrane holders (3122).

Figure 34:
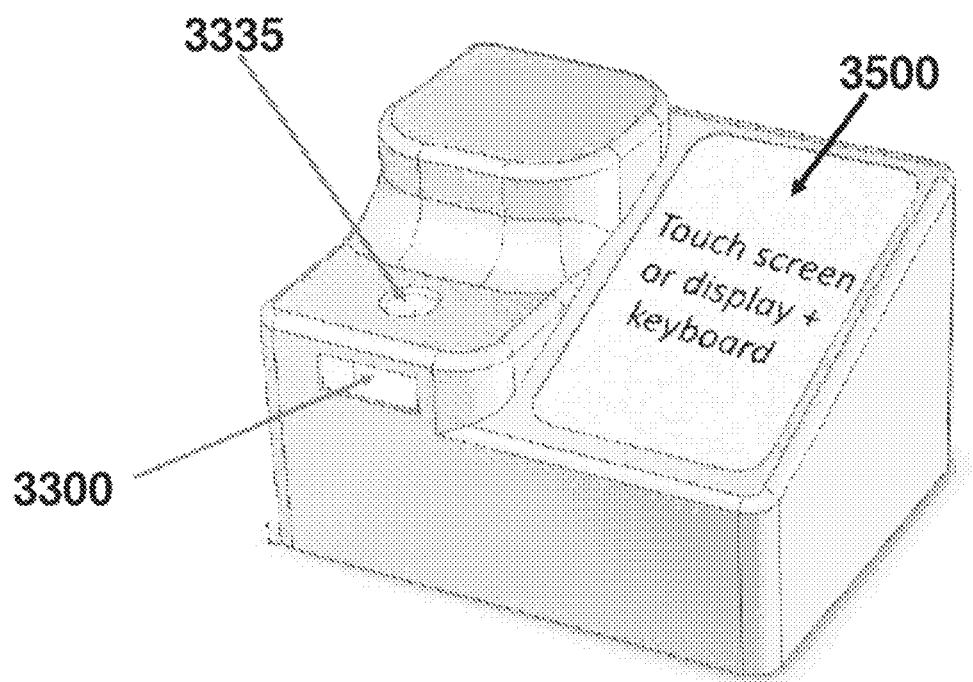
FIG. 34 depicts a representative device according to some embodiments of the present invention.

FIG. 34 depicts, in part, a device for detecting an analyte comprising an inlet (3335), a membrane system receptacle (3300), and display (3500).

Figure 35:
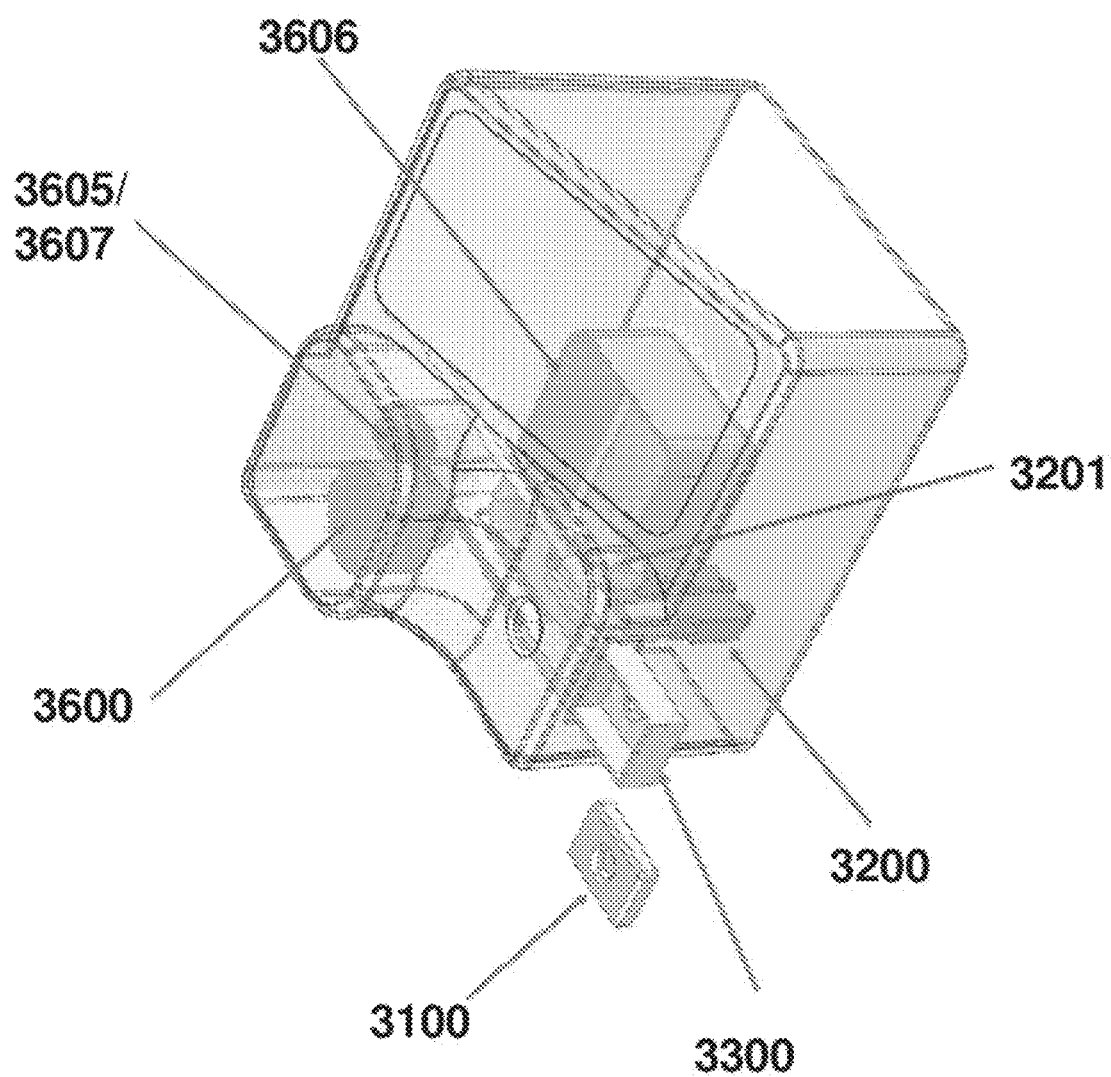
FIG. 35 depicts a representative device according to some embodiments of the present invention.

FIG. 35 depicts, in part, the interior of the device depicted in FIG. 34. The device comprises a cartridge comprising an analyte detection membrane system (3100), a membrane system receptacle (3300), a force actuator (3200), a spectrometer (e.g. optical reader or photodetector (3600), an optional conjugate pad remover (3201), an optional waste receptacle (3606), a motor and membrane system receptacle mover (3605/3607).

Figure 36A:
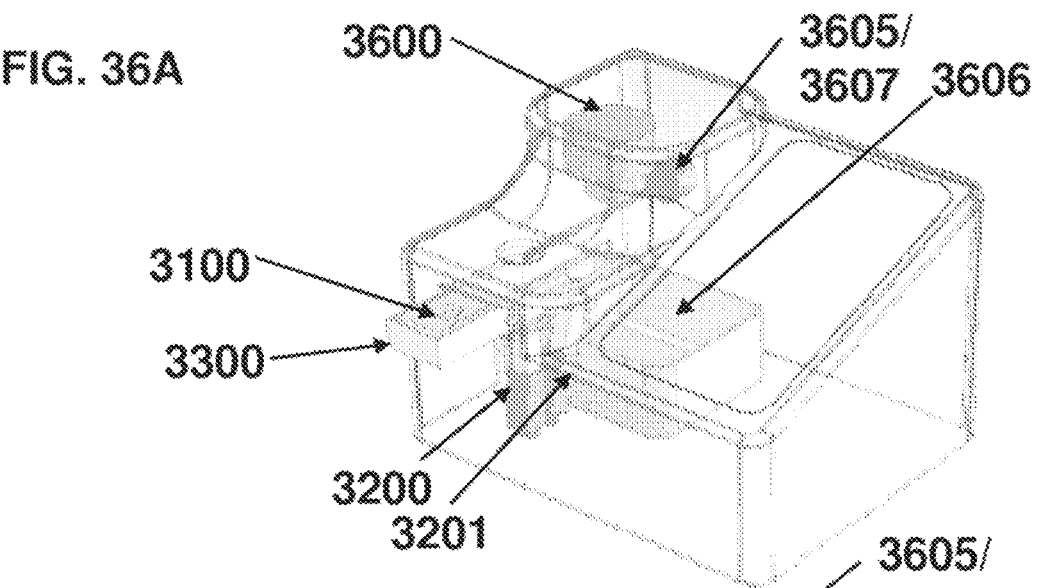
FIGS. 36A-36C depict a representative device according to some embodiments of the present invention.
Figure 36B:
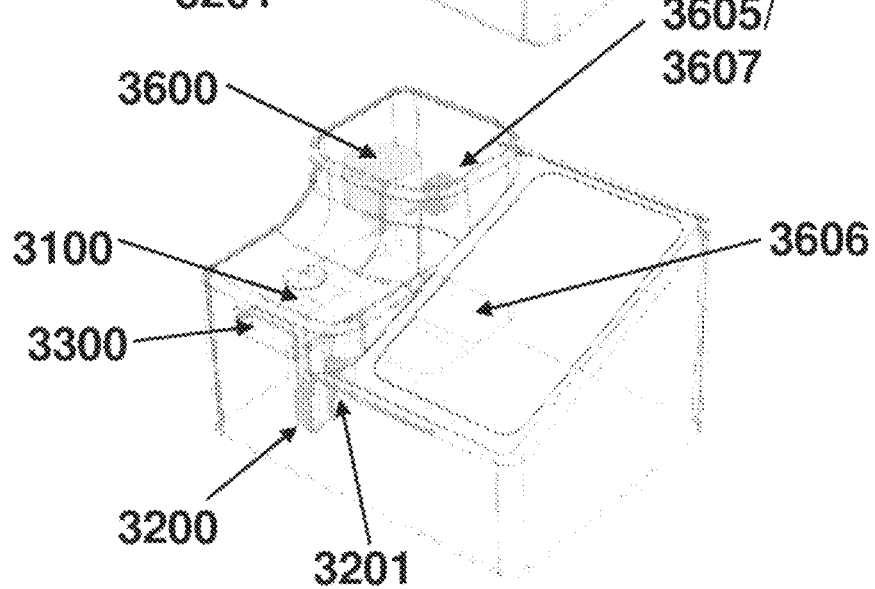
Figure 36C:
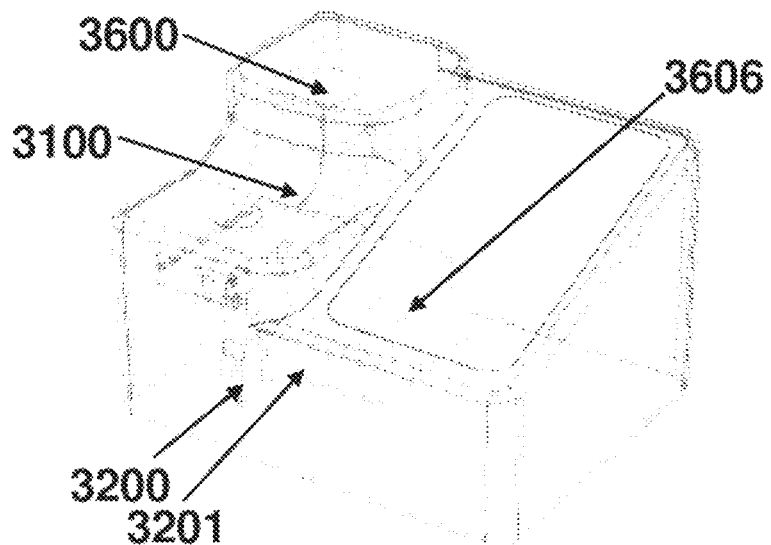

FIG. 36, shows the interior of a device depicted in FIGS. 34 and 35 at various stages of use with the same components depicted in FIG. 35. FIG. 36A depict the cartridge being inserted into the receptacle. FIG. 36B depicts the receptacle holding the cartridge being moved beneath the inlet for sample application and FIG. 36C depicts the sample being analyzed by the spectrometer.

The invention is now described with reference to the following examples. These examples are provided for the purpose of illustration only and the invention should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

EXAMPLES

Example 1

Antibody specific for *E. coli* 0157:H7 conjugated to colloidal gold was baked and dried onto the conjugate pad.

A second antibody specific for *E. Coli* O157:H7 and an anti-antibody was striped onto a test membrane and assembled into an analyte detection device.

A sample containing LPS *E. Coli* 0157 was serially diluted in PBS to concentrations of 100 µg/ml, 50 µg/ml, 25 µg/ml, 12.5 µg/ml, 6.25 µg/ml, 3.125 µg/ml, 1.56 µg/ml, and 0.78 µg/ml. The samples were applied to the device to detect the presence of LPS *E. Coli* 0157. The experiments were graded based upon signal intensity and the results are shown below. PBS was used as a negative control. TL refers to the test line (analyte specific) and CL refers to the control line (non-analyte specific). The detection occurred within 30 to 60 seconds of application of the sample onto the conjugate pad. The device could detect the presence of a food borne analyte.

| Sample Concentration | Grade | |
|---|---|---|
| | TL | CL |
| 100 ug/ml | 6 | 8 |
| 50 ug/ml | 6 | 8 |
| 25 ug/ml | 4 | 8 |
| 12.5 ug/ml | 4 | 8 |
| 6.25 ug/ml | 3 | 8 |
| 3.125 ug/ml | 3 | 8 |
| 1.56 ug/mL | 1 | 8 |
| 0.78 ug/ml | 1 | 8 |
| 1XPBS (Negative Control) | 1 | 8 |

Example 2

Evaluation of Species Specificity and Detection of *E. coli* O157:H7, *Campylobacter jejuni*, and *Salmonella enterica* serovar *Typhimurium* in a device comprising 3 analyte detection membrane systems and a channel system. A multiplex assay was performed using a device comprising 3 analyte detection membrane systems and a channel system comprising 3 branches. The assay was performed to see if a single sample could be used to detect 3 different strains of bacteria, *E. coli* O157:H7, *Campylobacter jejuni* subspecies *jejuni*, and *Salmonella enterica* serovar *Typhimurium*. The assay was performed with clinically relevant species of bacteria responsible for food-borne contamination and resulting illness in the United States in order to assess the specificity of the test for *E. coli* O157:H7, *Campylobacter jejuni* subspecies *jejuni*, and *Salmonella enterica* serovar *Typhimurium*. An evaluation of the functionality of the test was also conducted during the assay to assess the device's ability to function normally in the absence of pathogen exposure. The sample was contacted with the device and the device was successful in detecting *S. enterica Typhimurium* with high specificity as it showed positive results for multiplex assay samples where the strain was present, and negative results in samples where the strain was not added. *E. coli* O157:H7 strain was also detected in the samples were the analyte was present and not detected in samples where the analyte was not present. For *C. jejuni* strain, the device did not create any false positives, but was not 100% accurate in identifying samples that had *C. jejuni* present. The device was still capable of identifying more than 1 analyte from a single sample, and could identify up to 3 analytes depending on the sample. An increase or concentration of analyte or a higher affinity antibody could be used to increase detection and/or sensitivity.

The conclusion of the study is that a multiplex device comprising 3 analyte detection membrane systems and a channel system was successful in detecting multiple species of bacteria at the same time during the same test operation.

Example 3

Experiments demonstrated that a device comprising an analyte detection membrane system and force member, wherein the sample flows vertically through the analyte detection membrane system was able to distinguish between *E. coli* O157:H7 ATCC 43895 and a non-pathogenic *E. coli* strain (*Escherichia coli* ATCC 29425). The device was able to detect *E. coli* O157:H7 ATCC 43895 when combined with a non-pathogenic *E. coli* strain (representative of exposure to multiple microflora). The device demonstrated no cross reactivity to *Escherichia coli* ATCC 29425. The device demonstrated no cross reactivity even when in the presence of a 10 fold increase in concentration of the non-pathogenic *Escherichia coli* ATCC 29425. The device also showed no false negatives when tested against control samples and non-pathogenic *E. coli* ATCC 29425 strains. The devices exhibited a robust control line in the complete absence of a test line and were free of any background signal. The visual signal created when exposed to a sample was distinct and clearly interpretable by the naked eye. The signal developed rapidly after exposure to the bacteria and the signal was discernible within an average of 60 seconds post-exposure. Each test condition evaluated was done using five replicate tests and one control, and the devices produced highly reproducible results without any notable variation between replicates. The EcoliTrac Sentinel Platform was demonstrated to be a robust, sensitive, and discrimination detection system for *E. coli* O157:H7 when in the presence of non-pathogenic microflora.

Experiments demonstrated that a device comprising an analyte detection membrane system and force member, wherein the sample flows vertically through the analyte detection membrane system was successful in demonstrating performance and functionality when the device was exposed to *E. coli* O157:H7 in increasing concentrations of fetal bovine serum protein solution. The device was able to detect *E. coli* O157:H7 when exposed to various concentrations of fetal bovine serum protein solution. Evaluation of the control samples exhibited a robust control line in the complete absence of a test line and was free of any background signal. The device was even able was able to detect *E. coli* O157:H7 when exposed to a 100% Fetal Bovine Serum protein solution concentration. The visual signal created by the use of the device was distinct and clearly interpretable by the naked eye. 6. The signal developed rapidly after exposure to the bacteria and the signal was discernible within an average of 60 seconds post-exposure to the sample. Each test condition evaluated was done using five replicate tests and two controls, and the results were highly reproducible without any notable variation between replicates. The device was demonstrated to be a robust, sensitive, and discriminating detection system for *E. coli* O157:H7 when in the presence of a serum protein solution.

Experiments demonstrated that a device comprising an analyte detection membrane system and force member, wherein the sample flows vertically through the analyte detection membrane system were successful in demonstrating performance and functionality of the device for detecting *E. coli* O157:H7 when exposed to a quaternary ammonium compound. The Invisible Sentinel diagnostic assay was able to detect *E. coli* O157:H7 when exposed to increasing concentrations of a Quaternary Ammonium Compound in Fetal Bovine Serum, including exposure to the manufacturer's recommended dilution for an effective sanitizing and disinfecting solution (1.58%). Evaluation of the control samples exhibited a robust control line in the complete absence of a test line and was free of any background signal. The visual signal created by the system was distinct and clearly interpretable by the naked eye. The signal developed rapidly after exposure to the bacteria and the signal was discernible within an average of 60 seconds post-exposure of the sample. Each test condition evaluated was done using five replicate tests and two controls, and the results proved highly reproducible without any notable variation between replicates. The device was demonstrated to be a robust, sensitive, and discriminating detection system for *E. coli* 0157:H7 when in the presence of a quaternary ammonium compound.

In conclusion, the experiments described above looked at the ability of the device to *E. coli* 0157:H7 in the presence of various environmental contaminants that the device would likely encounter during its service life. The results of these studies (summarized above), demonstrate the unexpected and surprising robustness of the system. Unexpectedly, there was no loss of test performance when exposed to the various environmental contaminants, and the system proved to be a practical, easy to use, and interpretive method for the detection of *E. coli* 0157:H7 with a readout in about a minute, significantly faster than most assays on the market.

Example 4

The specificity of a device comprising an analyte detection membrane system and force member, wherein the sample flows vertically through the analyte detection membrane system for *Salmonella enterica* subsp. *enterica* serovar *Typhimurium* was evaluated. This study challenged the device with clinically relevant species of bacteria responsible for food-borne contamination and resulting illness in the United States in order to assess the specificity of the test for *Salmonella enterica*. An evaluation of the functionality of the test was also conducted during the study assessing the diagnostics ability to function normally in the absence of pathogen exposure. This study demonstrated the following that the device can be used to specifically identify *Salmonella* after exposure to various bacterial species associated with foodborne illness and outbreak events. The platform used to identify *Salmonella* demonstrated no cross reactivity to the following test strains: *Escherichia coli* 0157:H7 ATCC 43895, *Listeria monocytogenes* ATCC 13932, *Vibrio parahaemolyticus* ATCC 17802, and *Staphylococcus aureus* ATCC 10832. The visual signal created by the system was distinct and clearly interpretable by the naked eye. The signal developed rapidly after exposure to the bacteria and the signal was discernible within an average of 60 seconds post-exposure. Evaluations of the control samples and of assays exposed to species other than *Salmonella enterica* ATCC 13311 exhibited a robust control line in the complete absence of a test line and were free of any background signal. Evaluation of the *Salmonella enterica* ATCC 13311 strains exhibited both a robust test line and control line and were free of any background signal. Each bacterial strain evaluated using three replicate tests and one control, and the results proved highly reproducible without any notable variation between replicates. The *Salmonella* device was able to distinguish between *Salmonella enterica* ATCC 13311 and multiple pathogenic bacterial strains associated with foodborne illness (*Escherichia coli* 0157:H7 ATCC 43895, *Listeria monocytogenes* ATCC 13932, *Vibrio parahaemolyticus* ATCC 17802, *Staphylococcus aureus* ATCC 10832). Overall, the *Salmonella* platform was demonstrated to be a robust, sensitive, and discriminating detection system for *Salmonella enterica* ATCC 13311.

As demonstrated in this example, the *Salmonella* platform proved to be a robust, sensitive, reproducible, and easy to interpret assay for the identification of *Salmonella enterica* ATCC 13311.

Example 5

The purpose of this study was to evaluate the specificity of a device comprising an analyte detection membrane system and force member, wherein the sample flows vertically through the analyte detection membrane system for *Campylobacter jejuni* subspecies *jejuni*. This study challenged the assay with clinically relevant species of bacteria responsible for food-borne contamination and resulting illness in the United States in order to assess the specificity of the test for *Campylobacter jejuni*. An evaluation of the functionality of the test was also conducted during the study assessing the diagnostics ability to function normally in the absence of pathogen exposure. This study demonstrated the following that the device was successful in demonstrating functionality and specificity of for *Campylobacter* after exposure to various bacterial species associated with foodborne illness and outbreak events. The *Campylobacter* Platform demonstrated no cross reactivity to the following test strains: *Escherichia coli* 0157:H7 ATCC 43895, *Listeria monocytogenes* ATCC 13932, *Vibrio parahaemolyticus* ATCC 17802, *Staphylococcus aureus* ATCC 10832, and *Salmonella enterica* ATCC 13311. The visual signal created by the system was distinct and interpretable by the naked eye. The signal developed rapidly after exposure to the bacteria and the signal was discernible within an average of 4 minutes post-exposure. Evaluations of the control samples and of assays exposed to species other than *Campylobacter jejuni* ATCC 33560 exhibited a robust control line in the complete absence of a test line and were free of any background signal. Evaluation of the *Campylobacter jejuni* ATCC 33560 strains exhibited both a positive test line and robust control line and were free of any background signal. Each bacterial strain evaluated was done so using three replicate tests, and the results proved highly reproducible without any notable variation between replicates. The negative control for test functionality and media sterility was evaluated using three replicates, and was successful in demonstrating functionality of the test in the absence of pathogen exposure. The *Campylobacter* platform was able to distinguish between multiple pathogenic bacterial strains associated with foodborne illness: *Salmonella enterica* ATCC 13311, *Escherichia coli* 0157:H7 ATCC 43895, *Listeria monocytogenes* ATCC 13932, *Vibrio parahaemolyticus* ATCC 17802, *Staphylococcus aureus* ATCC 10832. Overall, the *Campylobacter* Sentinel Platform was demonstrated to be a discriminating detection system for *Campylobacter jejuni* ATCC 33560. As demonstrated in the experiment described above, the *Campylobacter* Platform proved to be a reproducible assay for the identification of *Campylobacter jejuni*.

Example 6

The specificity and performance of the a multiplex assay and device, such as shown in FIG. 20 was evaluated for its ability to detect *E. coli* O157:H7, *Campylobacter jejuni* subspecies *jejuni*, and *Salmonella enterica* serovar *Typhimurium* from a single sample. A sample that had been contaminated with the bacteria was applied to the device in a volume of about 750 microliters. The device was able to detect the presence of the 3 bacterial species. The device could detect *S. enterica Typhimurium* with high specificity and a limit of detection of approximately 103 cfu/ml as it showed positive results for multiplex assay samples where the strain was present, and negative results in samples where the strain was not added. *E. coli* O157:H7 strain was detected with high specificity and a limit of detection of approximately 103 cfu/ml demonstrating specificity and sensitivity for the strain (negative results were obtained when *E. coli* O157:H7 was not present). The multiplex assay was also able to detect the *C. jejuni* strain in samples where the strain was present with high specificity and a limit of detection of approximately 104 cfu/ml, showing the multiplex assay also effective at identifying this strain. The multiplex device was, therefore, surprisingly successful in detecting multiple species of bacteria at the same time during the same test operation.

The disclosures of each and every patent, patent application, publication, and accession number cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A device for detecting an analyte comprising:
   a housing comprising a first housing member and a second housing member, wherein the housing further comprises:
   an inlet;
   a first force member in contact with a first force actuator outlet;
   a second force member in contact with a second force actuator outlet;
   a movable locking member contacting the first force member and the second force member;
   a first and second analyte detection membrane system comprising in the following order:
   a conjugate pad;
   an optional permeable membrane;
   a test membrane;
   an absorbent member; and
   a first flexible or fixed attachment member attached to the movable locking member and the conjugate pad of the first analyte detection membrane system;
   a second flexible or fixed attachment member attached to the movable locking member and the conjugate pad of the second analyte detection membrane system; and
   a channel system or membrane that transports fluid from the inlet to the first and second analyte detection membrane systems;
   wherein at least a portion of each of the conjugate pad, permeable membrane, test membrane, and absorbent member are substantially parallel to each other;
   wherein the first and second analyte detection systems are capable of being compressed;
   wherein the first force member contacts the absorbent member of the first analyte detection membrane system and when the first force member is engaged applies pressure substantially perpendicular to the first analyte detection membrane system; and
   wherein the second force member contacts the absorbent member of the second analyte detection membrane system and when the second force member is engaged applies pressure substantially perpendicular to the second analyte detection membrane system.

2. The device of claim 1, wherein said movable locking member comprises one or more movable locking member extensions that contacts said first force member and second force member.

3. The device of claim 2, wherein said one or more movable locking member extensions extend outward from the center of said movable locking member.

4. The device of claim 1, wherein said movable locking member comprises a flexible or fixed attachment member extension or a structure contacting the conjugate pad that mediates the conjugate pad's displacement.

5. The device of claim 4, wherein said flexible attachment member extension contacts said flexible attachment member.

6. The device of claim 1, wherein the channel system comprises a capillary channel system or absorbent material that transports fluid.

7. The device of claim 1, wherein the channel system comprises at least two capillaries in contact with the first analyte detection system and at least two capillaries in contact with the second analyte detection system.

8. The device of claim 1, wherein the channel system contacts an edge of the conjugate pad of the first analyte detection system or an edge of the conjugate pad of the second analyte detection system.

9. The device of claim 1, further comprising one or more portals allowing the visualization of the first and second analyte detection systems.

10. The device of claim 1, wherein the force actuator outlet has a circumference that is greater than a circumference of the force member wherein the force member has areas that have different circumferences.

11. The device of claim 1, further comprising a moving member that is accessible through the outer surface of the first or second housing member, wherein the moving member contacts the locking member, wherein movement of the moving member moves the locking member.

12. The device of claim 11, wherein the moving member rotates around a central axis of the device when moved.

13. The device of claim 1, wherein the conjugate pad of the first analyte detection membrane system comprises a first analyte-specific capture reagent and the second analyte membrane system comprises a second analyte-specific capture reagent.

14. The device of claim 13, wherein the analyte recognized by the first analyte-specific capture reagent and second analyte-specific capture reagent is a food-borne pathogen analyte.

15. The device of claim 14 wherein the food-borne pathogen analyte is independently an analyte from an *E. coli* species, a *Listeria* species, a *Campylobacter* species, or a *Salmonella* species.

16. The device of claim 13, wherein the first analyte-specific capture reagent and second analyte-specific capture reagent is independently conjugated to colloidal gold, silver, a functionalized nanoparticle, a fluorescent molecule, radioactive tag, nanocrystal, or a chemiluminescent substrate.

17. A method of detecting an analyte comprising:
   contacting a sample with the channel system of the device of claim 13, wherein a portion of the sample flows to the conjugate pad of the first and second analyte detection membrane systems; and detecting a positive or negative reaction for the analyte, wherein a positive reaction indicates presence of the analyte.

18. A kit comprising the device of claim 1 and one or more of a positive control, a negative control, an instruction booklet, a buffer container, and a sample collector, or any combination thereof.

* * * * *